US012186437B2

(12) United States Patent
Wu et al.

(10) Patent No.: US 12,186,437 B2
(45) Date of Patent: Jan. 7, 2025

(54) SELF-SANITIZING STRUCTURE FOR IMPLEMENTING SANITIZATION PATTERNS THAT NEUTRALIZE INFECTIOUS AGENTS ON THE STRUCTURE'S SURFACES

(71) Applicant: DuPont Electronics, Inc., Wilmington, DE (US)

(72) Inventors: Wei Wu, Hockessin, DE (US); Gregory Scott Blackman, Media, PA (US); Barry D. Olson, Buffalo, NY (US); Timothy S. Wyant, Cheektowaga, NY (US); Fazel Zare Bidoky, Philadelphia, PA (US); Michael R. Moseley, New Castle, DE (US)

(73) Assignee: DUPONT ELECTRONICS, INC., Wilmington, DE (US)

( * ) Notice: Subject to any disclaimer, the term of this patent is extended or adjusted under 35 U.S.C. 154(b) by 225 days.

(21) Appl. No.: 17/061,668

(22) Filed: Oct. 2, 2020

(65) Prior Publication Data
US 2022/0062460 A1    Mar. 3, 2022

Related U.S. Application Data

(63) Continuation of application No. 17/009,938, filed on Sep. 2, 2020.

(51) Int. Cl.
*A61L 2/08* (2006.01)
*A61L 2/26* (2006.01)

(52) U.S. Cl.
CPC ............. *A61L 2/084* (2013.01); *A61L 2/26* (2013.01); *A61L 2202/11* (2013.01)

(58) Field of Classification Search
CPC ......... A61L 2/26; A61L 2/084; A61L 2202/11
See application file for complete search history.

(56) References Cited

U.S. PATENT DOCUMENTS

| 7,223,281 B2 | 5/2007 | Altshuler et al. |
| 7,543,956 B2 | 6/2009 | Piepgras et al. |

(Continued)

FOREIGN PATENT DOCUMENTS

EP    1658784 B1    5/2006

OTHER PUBLICATIONS

Bumah et al., "Optimizing the bactericidal effect of pulsed blue light on Propionibacterium acnes—a correlative fluorescence spectroscopy study." Journal of Photochemistry and Photobiology B: Biology 202 (2020): 111701.

(Continued)

*Primary Examiner* — Sean E Conley
(74) *Attorney, Agent, or Firm* — CANTOR COLBURN LLP

(57) ABSTRACT

Embodiments of the invention are directed to a self-sanitizing structure that includes a body having a contact surface that can be contacted by a person, along with an energy source formed as an array of addressable energy sources. The energy source generates electromagnetic radiation and direct the electromagnetic radiation through the body to the contact surface. A sensor system is coupled to the contact surface, and a controller is coupled to the energy source and the sensor system. The body scatters the electromagnetic radiation and passes it through the body to the contact surface in a manner that maintains the scattered electromagnetic radiation that reaches the contact surface as sanitizing electromagnetic radiation at or above a minimum irradiance level that neutralizes infectious agents. The sensor system generates touch data in response to the contact surface being touched, and the controller uses the touch data to control the addressable energy sources.

19 Claims, 26 Drawing Sheets

(56) References Cited

U.S. PATENT DOCUMENTS

| | | | |
|---|---|---|---|
| 9,229,597 B2 | 1/2016 | Oraw | |
| 9,235,278 B1 | 1/2016 | Cheng et al. | |
| 9,365,724 B2 | 6/2016 | Rose et al. | |
| 9,371,425 B2 | 6/2016 | Rose et al. | |
| 9,388,295 B2 | 7/2016 | Rose et al. | |
| 9,463,126 B2 | 10/2016 | Zerhusen et al. | |
| 9,700,641 B2 | 7/2017 | Hawkins et al. | |
| 10,363,325 B2 | 7/2019 | Hawkins et al. | |
| 10,434,202 B2 | 10/2019 | Hawkins et al. | |
| 10,456,485 B1 | 10/2019 | Hawkins et al. | |
| 10,639,498 B2 | 5/2020 | Enwemeka et al. | |
| 2007/0198004 A1 | 8/2007 | Altshuler et al. | |
| 2012/0019917 A1 | 1/2012 | Riebel et al. | |
| 2014/0304447 A1 | 10/2014 | Fils | |
| 2015/0129781 A1* | 5/2015 | Kretschmann | A61L 2/10 250/492.1 |
| 2015/0258228 A1* | 9/2015 | Cohen | G06F 3/0416 250/492.1 |
| 2016/0303394 A1 | 10/2016 | Hayashi et al. | |
| 2018/0162026 A1 | 6/2018 | Stvartak et al. | |
| 2018/0243458 A1 | 8/2018 | Shatalov et al. | |
| 2018/0280723 A1 | 10/2018 | Enwemeka et al. | |
| 2019/0030196 A1 | 1/2019 | Bilenko et al. | |
| 2019/0143140 A1 | 5/2019 | Enwemeka et al. | |
| 2022/0016282 A1 | 1/2022 | Kim | |
| 2023/0241261 A1 | 8/2023 | Wu et al. | |

OTHER PUBLICATIONS

DuPont, "DuPont Tedlar Wallcoverings." (2017) 2 pages.

Halstead et al., "Antibacterial activity of blue light against nosocomial wound pathogens growing planktonically and as mature biofilms." Applied and environmental microbiology 82.13 (2016): 4006-4016.

Shaer et al. "Interactive capacitive touch music table with embedded microcontrollers." The Journal of Supercomputing 76.11 (2020): 8845-8865.

St. Denis et al., "Killing bacterial spores with blue light: when innate resistance meets the power of light." Photochemistry and photobiology 89.1 (2013): 2-4.

Stibich et al., "The microbiological impact of pulsed xenon ultraviolet disinfection on resistant bacteria, bacterial spore and fungi and viruses." Southern African Journal of Infectious Diseases 31.1 (2016): 12-15.

Tomb, Rachael Margaret. "Antimicrobial 405 nm light for clinical decontamination: investigation of the antiviral efficacy and potential for bacterial tolerance." Diss. University of Strathclyde, 2017, 308 pages.

Zhu et al., "Understanding Radiance (Brightness), Irradiance and Radiant Flux." Energetiq, Technical Note #004-3-25-2011 (2011) pp. 1-4.

* cited by examiner

Characteristics/Properties of the Self-sanitizing Structure 100 for Controlling the Minimum Light Irradiance 116A at the Contact Surface 102 that Neutralizes Infectious Agents

TABLE A – Sanitization Characteristics/Properties
1. Body region 106 composition (volume and/or weight percent) of scattering elements 106B (e.g., particulate elements, pigments, fibers and/or micro-fibers)
2. Size distribution (diameters) of the scattering elements 106B in the body region 106
3. Light and/or Wavelength attenuation/absorption characteristics 106C of the body region 106
4. Thickness (T1) of the upper body 108
5. Power level(s) (continuous wave or pulsed) of the Light Sources 112, 112A
6. Path length between the LED(s) 702, 712 and the contact surface 102
7. Angle of each LED 702, 712 relative to the contact surface 102
8. Internal and external surface roughness 106D of the body region 108

TABLE B – Light Coverage or Footprint Characteristics/Properties
1. Size distribution (diameters) of the scattering elements 106B in the body region 106
2. LED Array 700 density/pitch
3. Optical properties and thickness of the diffuser element 107C and 1102 (e.g., a spunbonded material made from high-density polyethylene fibers) (e.g., Tyvek®)
4. Configuration of the lens elements 107B (e.g., radius, distance to contact surface 102, distance from the lens elements 106C to the contact surface 102)
5. Dispersion of scattering elements 106B within the body region 106
6. Layer compositions and stack-up for the multi-layered sheets 206
7. Fiber/micro-fiber diameter, density, thickness of each fiber-containing layer 206B of the flexible multi-layered sheets 206
8. Optical properties of each layer of the flexible multi-layered sheets 206
9. Roughness of each layer of the flexible multi-layered sheets 206

FIG. 2E

Sanitization Pattern 1524A

| | Time 0 | Time 1 | Time 2 | Time 3 |
|---|---|---|---|---|
| Addressable LED A | ON 2hrs | ON 2 hrs | ON 2 hrs | OFF |
| Addressable LED B | ON 2hrs | ON 2 hrs | ON 2 hrs | OFF |
| Addressable LED C | ON 2hrs | ON 2hrs | ON 2hrs | OFF |
| Addressable LED D | OFF | OFF | OFF | OFF |
| Addressable LED E | OFF | OFF | OFF | OFF |

Sanitization Pattern 1722A

|  | Time 0 | Time 1 | Time 2 | Time 3 |
|---|---|---|---|---|
| LED A | On 2hrs | OFF | OFF | OFF |
| LED B | On 2hrs | OFF | OFF | OFF |
| LED C | On 2hrs | On 2hrs | On 2hrs | OFF |
| LED D | On 2 hrs | On 2hrs | On 2hrs | OFF |
| LED E | OFF | OFF | OFF | OFF |

SELF-SANITIZING STRUCTURE FOR IMPLEMENTING SANITIZATION PATTERNS THAT NEUTRALIZE INFECTIOUS AGENTS ON THE STRUCTURE'S SURFACES

DOMESTIC PRIORITY

This application is a continuation of U.S. application Ser. No. 17/009,938, filed Sep. 2, 2020, the contents of which are incorporated by reference herein in its entirety.

BACKGROUND

The present invention relates in general to a structure having a commonly touched surface. More specifically, the present invention relates to a self-sanitizing structure having integrated (or embedded) sanitizing elements configured to generate and apply a sanitization pattern of electromagnetic radiation that neutralizes infectious agents on a commonly touched surface of the self-sanitizing structure.

Infectious agents (e.g., microbes, protozoa, bacteria, viruses, and the like) can persist on environmental surfaces long enough for the surface to act as a conduit for indirect transfer of the infectious agent(s) from one person to another. Commonly touched environmental surfaces, along with the disease transmission risks associated therewith, are present in virtually every environment that humans encounter in daily life, including, for example, homes, schools, day care centers, elderly residential care facilities, hospitals, grocery stores, office buildings, restaurants, airplanes, and the like.

SUMMARY

Embodiments of the invention are directed to a self-sanitizing structure that includes a body region having a contact surface that can be contacted by a person during an intended use of the self-sanitizing structure. The self-sanitizing structure further includes an energy source that includes an array of individually addressable energy sources, wherein the energy source is configured to generate electromagnetic radiation and direct the electromagnetic radiation through the body region to the contact surface. A sensor system is communicatively coupled to the contact surface, and a controller is communicatively coupled to the energy source and the sensor system. The body region is configured to scatter the electromagnetic radiation and pass the scattered electromagnetic radiation through the body region to the contact surface in a manner that maintains the scattered electromagnetic radiation that reaches the contact surface as sanitizing electromagnetic radiation. The sanitizing electromagnetic radiation is electromagnetic radiation that is at or above a minimum irradiance level that neutralizes infectious agents. The sensor system is configured to generate touch data in response to the contact surface being touched. The controller is configured to use the touch data to control how the energy source generates the electromagnetic radiation by controlling the individually addressable energy sources.

In some embodiments of the invention, the above-described self-sanitizing structure includes the controller being configured to control the individually addressable energy sources by performing controller operations that include generating from the touch data a touch data record having touch-related location data that identifies a location on the contact surface where a touch instance occurred, as well as touch-related time data that identifies a duration of the touch instance on the contact surface.

In some embodiments of the invention, the above-described controller operations include identifying, based at least in part on the touch-related location data, a set of the individually addressable energy sources that will, when instructed to do so, generate at least one instance of the electromagnetic radiation that results in the sanitizing electromagnetic being maintained at the location on the contact surface where the touch instance occurred.

In some embodiments of the invention, the above-described controller operations further include generating a sanitization pattern comprising instructions to the set of the individually addressable energy sources to generate, for a duration, the at least one instance of the electromagnetic radiation that results in the sanitizing electromagnetic being maintained at the location on the contact surface where the touch instance occurred.

In some embodiments of the invention, the above-described self-sanitizing structure includes the duration being sufficient to neutralize infectious agents at the location on the contact surface where the touch instance occurred.

In some embodiments of the invention, the above-described controller operations further including executing the sanitization pattern.

In some embodiments of the invention, the above-described controller operations further include storing in a memory of the controller sanitization compliance data comprising results of executing the sanitization pattern.

In some embodiments of the invention, the above-described controller operations further include generating a sanitization compliance report based at least in part on the sanitization compliance data.

In some embodiments of the invention, the above-described controller operations further include identifying, based at least in part on the touch-related location data, the set of the individually addressable energy sources that will, when instructed to do so, generate the at least one instance of the electromagnetic radiation that results in the sanitizing electromagnetic being maintained at the location on the contact surface where the touch instance occurred includes utilizing a first mapping of the set of individually addressable energy sources to contact surface locations on the contact surface.

In some embodiments of the invention, the above-described self-sanitizing structure includes each of the individually addressable energy sources, when activated, projecting onto the contact surface the sanitizing light, wherein the sanitizing electromagnetic radiation on the contact surface has a sanitizing electromagnetic energy footprint, and wherein the first mapping associates the sanitizing electromagnetic radiation footprint of each of the individually addressable energy sources with one or more of the contact surface locations.

Embodiments of the invention are also directed to methods of fabricating a self-sanitizing structure having the features and functionality of the above-described self-sanitizing structure.

Additional features and advantages are realized through the techniques described herein. Other embodiments and aspects are described in detail herein. For a better understanding, refer to the description and to the drawings.

BRIEF DESCRIPTION OF THE DRAWINGS

The subject matter which is regarded as the present invention is particularly pointed out and distinctly claimed in the claims at the conclusion of the specification. The foregoing and other features and advantages are apparent from the following detailed description taken in conjunction with the accompanying drawings in which:

FIG. 2E depicts tables illustrating characteristics (and/or properties) of a self-sanitizing structure in accordance with embodiments of the invention;

Figure 1:
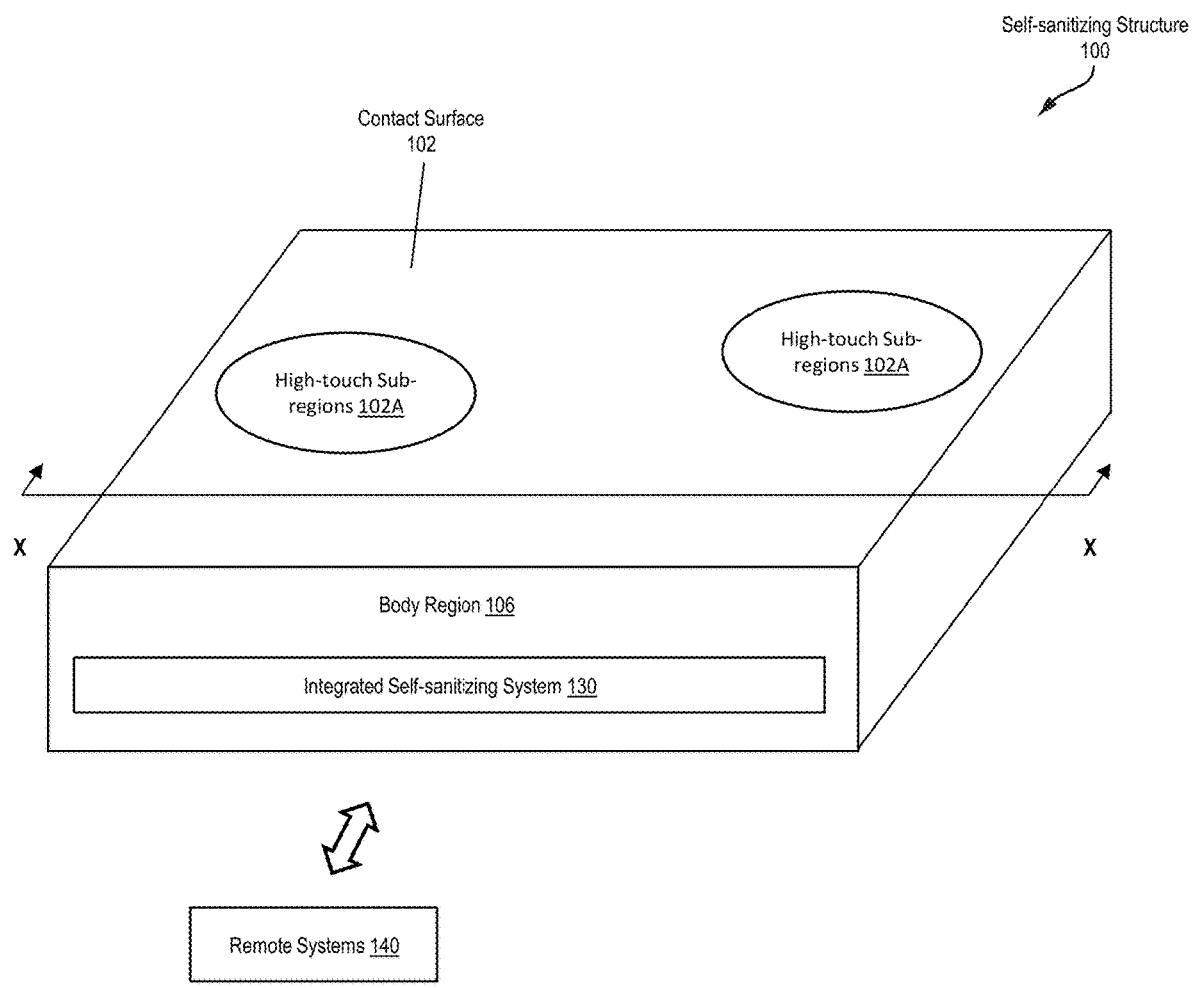
FIG. 1 depicts a block diagram of a self-sanitizing structure in accordance with embodiments of the invention.

In the accompanying figures and following detailed description of the disclosed embodiments, the various elements illustrated in the figures are provided with two, three, or four digit reference numbers. In most instances, the leftmost digit(s) of each reference number corresponds to the figure in which its element is first illustrated.

DETAILED DESCRIPTION

For the sake of brevity, conventional techniques related to making and using aspects of the invention may or may not be described in detail herein. In particular, various aspects of the materials, structures, computing systems, and specific computer programs to implement the various technical features described herein are well known. Accordingly, in the interest of brevity, many conventional implementation details are only mentioned briefly herein or are omitted entirely without providing the well-known system and/or process details.

Turning now to an overview of technologies that are more specifically relevant to aspects of the invention, a known approach to combatting the spread of infectious agents is to frequently sanitize environmental surfaces that are commonly touched by humans. Known surface sanitization methods include exposing the surface to, for example, chemical disinfectants and/or ultraviolet (UV) light. In addition to UV light, it has also been proposed that blue and/or purple light above certain irradiance levels and applied for a sufficient length of time can neutralize infectious agents. However, known surface sanitization methods have shortcomings. For example, the processes used to apply chemical disinfectants and/or light (UV or blue/purple) to a surface are labor intensive; are susceptible to human error in the application of the sanitization method; must be tightly controlled to prevent or minimize harm to the humans; and can damage various types of surfaces, including surfaces that are routinely used in healthcare facilities. For example, fabric surfaces on chairs, sofas, and the like cannot be cleaned with bleach-based disinfectants. UV light also has destructive effect over time on plastics and vinyl and causes the coloring in paints and fabrics to fade. Additionally, using known sanitization methods, it can be difficult to distinguish surfaces that have been touched from surfaces have not been touched, and it can also be difficult to ensure that all of the commonly touched regions of an environmental surface have been sanitized. In the case of chemical disinfectants (e.g., bleach), the method used to apply the disinfectant must be sufficiently rigorous to ensure that disinfectant is applied to all regions of the surface, and the chemical agent must be in contact with the surface for a certain period of time. In the case of the light exposure sanitization, the method used to apply light to the surface must ensure that the light irradiance at the surface is high enough to affect infectious agents; and must ensure that the line of sight from the light source to the surface is clear because portions of the target surface where the line of sight is blocked or shadowed will not be exposed to light and will not be disinfected.

Further, known methods of sanitizing commonly touched environmental surfaces can require that the intended function of the surface is interrupted in order to apply the sanitization method. In addition to being disruptive, interrupting the intended function of the surface can also limit how frequently the sanitization method can be applied, as well as the duration of a given sanitization application. For example, a conference room in an office building is used to host a 3 day seminar. The conference room has a large conference table, and the attendees are seated around the conference table during the seminar. Each seminar attendee receives a large binder of presentation materials, and, ideally, the seminar hosts would like to allow the attendees to leave their presentation materials and notes on the conference table so the attendees don't have to carry these bulky items back and forth each day. The seminar hosts would also like to sanitize the conference table surface each evening as part of its procedures for reducing the likelihood of spreading infectious diseases. Using known methods of sanitizing surfaces, the seminar hosts would be required to interrupt the intended function of the conference table surface each evening by removing all items from the conference table surface, applying the sanitization method (e.g., chemical disinfectant and/or UV light exposure), and returning all removed items to the conference table surface in their same locations.

Turning now to an overview of aspects of the invention, embodiments of the invention address the above-described shortcomings of known approaches to surface sanitization by providing a self-sanitizing structure having a novel, covert self-sanitizing system. The self-sanitizing system is covert in that it is integrated within a body region of the self-sanitizing structure in a manner that enables the self-sanitizing structure to sanitize its commonly touched surfaces without interfering with the intended functions of the commonly touched surfaces. The integrated self-sanitizing system includes a light source configured and arranged to transmit light through the body region to the commonly touched surface. Because light from the light source passes through the commonly touched surface, the commonly touched surface is referred to herein as a light exit surface of the self-sanitizing structure.

In accordance with aspects of the invention, selected characteristics or properties of the self-sanitizing structure are configured and arranged to scatter/disperse the light passing through the body region such that an irradiance level of the light that reaches the exit surface is maintained at or above a minimum irradiance level that will neutralize infectious agents. As used herein, the term "neutralize" refers to an interaction with an infectious agent that renders the infectious agent no longer infectious or pathogenic. Light that is maintained at or above a minimum irradiance level that will neutralize infectious agents is referred to herein as "sanitizing light." In some embodiments of the invention, the light transmitted by the light source is a continuous wave. In some embodiments of the invention, the light transmitted by the light source is a series of pulses having a controlled pulse width, frequency and/or duty cycle. In some embodiments of the invention, the minimum irradiance level that will neutralize infectious agents can be about 0.5 mW/cm$^2$. In some embodiments of the invention, the minimum irradiance level that will neutralize infectious agents can be about 1 mW/cm$^2$. The minimum light irradiance level that will neutralize infectious agents can be determined experimentally using known simulation tools (including image analysis) to model the self-sanitizing structure and the integrated self-sanitizing system.

In accordance with aspects of the invention, the selected characteristics/properties of the self-sanitizing structure are configured and arranged in a manner that maintains light that passes from the light source through the body region to the exit surface at or above a minimum irradiance level that will neutralize infectious agents with no unintended non-sanitized regions of the exit surface. As used herein, the terms "non-sanitized region" refer to surface regions where light irradiance is below a minimum irradiance level that will neutralize infectious agents. In embodiments of the invention, the characteristics/properties of the self-sanitizing structure that are configured and arranged to achieve and maintain sanitizing light with no non-sanitized regions at the body region's exit surface are referred to herein as sanitization characteristics or sanitization properties.

In embodiments of the invention, the sanitization characteristics/properties of the self-sanitizing structure can be set or otherwise determined in a manner that enables the self-sanitizing structure to scatter light that passes from the light sources through the body region and the exit surface in a manner that maintains sanitizing light (i.e., light that is at or above a minimum irradiance level that will neutralize infectious agents) at the exit surface. In some embodiments of the invention, the sanitization characteristics/properties of the self-sanitizing structure can include any combination of the presence of spaced-apart scattering elements in the body region; a size distribution (or diameter-size distribution) of the spaced-apart scattering elements in a matrix material of the body region; spacing between the spaced-apart scattering elements in the matrix material of the body region; a refractive index of the matrix material of the body region; a difference between the refractive index or indices of the spaced-apart scattering elements and the refractive index of the matrix material of the upper body region; a percentage of the body region that is the spaced-apart scattering elements; a percentage of the body region that is the matrix material; a refractive index or indices of the matrix material of the body region. In some embodiments of the invention, the size of each of the spaced-apart scattering elements, as well as the difference between the refractive index or indices of the spaced-apart scattering elements and the refractive index of the matrix material of the upper body region, are sufficient to scatter the electromagnetic radiation; and the spacing between the spaced-apart scattering elements in the body region is sufficient to enable the scattered electromagnetic radiation to pass through the body region to the contact surface. In embodiments of the invention, the scattering elements having sufficient size to scatter light is from about 50 nanometers in diameter to about 50 micrometers in diameter, assuming there is a sufficient index of refraction mismatch between the scattering elements and the surrounding matrix material of the body region. In accordance with aspects of the invention, the matrix material can be implemented as a homogeneous and monolithic material in which the scattering elements and any additional filler materials are embedded to form a composite. The matrix material provides a medium for binding and holding the scattering elements and any additional filler elements together into a solid. In some embodiments of the invention, the matrix material can be a polymer matrix material. In some embodiments of the invention, the polymer matrix material can be a polymethyl methacrylate (PMMA) material.

In some embodiments of the invention, the sanitization characteristics/properties of the self-sanitizing structure can further include any combination of the light and/or wavelength attenuation and/or absorption characteristics of the various materials that form the body region; a topography (or roughness) of the contact/exit surface; an internal topography (or roughness) of the body region; the light absorption level of the elements that form the body region for light at the desired light wavelength; the power levels applied to the light source; a distance from the light source to the contact/exit surface; and/or whether the light source is configured to generate light a series of pulses having a controlled pulse width, frequency and/or duty cycle. In some embodiments of the invention, the coverage area or footprint of the sanitizing light on the contact/exit surface can be controlled by any combination of a distance from the light source to the contact/exit surface; lens elements; diffuser elements; the topography of the contact/exit surface; the internal topography of the body region; the size of the light source; the number of light sources; and/or a placement pattern of the light sources.

In some embodiments of the invention, the body region of the self-sanitizing structure can be a substantially nonflexible or substantially rigid material. As used herein, the terms "rigid material," "rigid body," "rigid structure," and equivalents thereof refer to a solid material in which deformation is zero (0) or so small it can be neglected and does not meaningfully change the structural integrity of the material. The distance between any two given points in or on a rigid material remains substantially constant in time regardless of external forces exerted on it. In some embodiments of the invention, the body region of the self-sanitizing structure can be a substantially flexible and relatively thin (e.g., about 0.05 mm to about 0.8 mm) multi-layered structure or sheet. As used herein, the terms "flexible material," "flexible body," "flexible structure," and equivalents thereof refer to a material characterized by the ability to bend or compress easily without cracking under the material's normal use conditions. In some embodiments of the invention, the body region can include a combination of substantially rigid portions and substantially flexible portions. In some embodiments of the invention, the substantially rigid body region can take a variety of forms, including but not limited to a substantially rigid structure such as a table, a tray, a wall, a door panel, or any other substantially rigid structures having at least one commonly touched or highly touched surface. In some embodiments of the invention, the substantially flexible body region can be a multi-layered sheet. In some embodiments of the invention, the substantially flexible body region can be configured and arranged to include components that enable the substantially flexible body region to function as a covering for an underlying material. For example, in some embodiments of the invention, the substantially flexible body region can be configured and arranged to function as a wall covering. The self-sanitizing structure's features and functions described herein apply to both substantially rigid and substantially flexible implementations of the body region unless such features/functions are specifically limited to a substantially rigid body region and/or a substantially flexible body region.

In embodiments of the invention where the body region is a substantially rigid material, the scattering elements can be particulate elements added to a matrix material of the body region during fabrication thereof. In embodiments of the invention where the body region is a substantially flexible multi-layered structure, the scattering elements can be implemented as a layer of fibrous elements; one or more layers of matrix material can form one or more flexible substrate layers that are secured to the layer of fibrous elements; the layer of fibrous elements can also, in some embodiments of the invention, include a matrix material; and the fibrous elements can be implemented as a combination of fiber elements and micro-fiber elements.

Because aspects of the invention relate to controlling the irradiance level of light that passes through the body region and reaches the commonly touched surface, a brief overview of terms and concepts related to radiometry and irradiance will now be provided. Evaluation of the performance of a radiation source involves the field of radiometry, which is the measurement of quantities associated with radiation. Radiometry terms and units are different from photometry terms and units. Radiometry is the science of measuring radiation energy in any portion of the electromagnetic spectrum. In practice, the term is usually limited to the measurement of ultraviolet (UV), visible (VIS), and infrared (IR) radiation using optical instruments. Photometry, on the other hand, is the science of measuring visible radiation in units that are weighted according to the sensitivity of the human eye. It is a quantitative science based on a statistical model of the human visual perception of light (eye sensitivity curve) under carefully controlled conditions.

For radiance, the SI unit is watts per square meter per steradian [$W/m^2$-sr]. Because many radiation sources used in laboratories have an emitting area in the square millimeters range, the unit of milliwatts per square millimeter per steradian [mW/mm$^2$-sr] is often used for radiance. The radiance (R) of the source emitting area (A) equals the radiation power (P), which is emitted from A and propagates in solid angle Ω, which is divided by the area A and the solid angle Ω such that R=P/(A×Ω).

Irradiance is the radiometry term for the power per unit area of electromagnetic radiation incident on a surface. The SI unit for irradiance is watts per square meter [W/m$^2$], or milliwatts per square millimeter [mW/mm$^2$]. Irradiance is a useful measure for applications where power must be delivered to large areas. For example, delivering light to a classroom or a football field is primarily a question of delivering a certain number of watts per square meter.

In known approaches to sanitizing a surface using light exposure, sanitizing light is transmitted to its target surface through a non-solid medium (e.g., air). Examples are shown in published U.S. patent application no. 20180243458A1, U.S. Pat. No. 7,223,281, and published U.S. patent application no. 20190143140A1. Such approaches do not disclose or suggest transmitting sanitizing light through a solid-medium (e.g., a rigid or flexible structure), nor do they disclose or suggest controlling characteristics/properties of the structure such that light passing through one or more predetermined regions of the structure's exit surface is maintained at or above a minimum irradiance level that neutralizes infectious agents with no non-sanitized regions in the predetermined region(s).

U.S. Pat. No. 7,543,956 (the '956 patent) disclose a method of securing electronic components (e.g., LED-based light sources and associated control circuitry) within molded or continuously cast surface materials during fabrication of the surface material. The '956 patent discloses that the molded or continuously cast surface material can be a material sold under the tradename Corian®. The '956 patent further discloses four (4) functions performed by its LEDs, which are described therein as "delineating areas on a surface, indicating temperature, e.g., by having a countertop glow red when heated by a hot object, providing warnings, and/or aiding sanitation as in the use of embedded ultraviolet lighting units for the purpose of killing pathogens on the surface of a counter."

Of the four (4) functions described above, for the first three (3) functions, the '956 patent teaches the use of various elements (e.g., diffusion and/or diffracting layers, lenses, shaped light guides and/or other means for directing light) to control how the '956 patent's LED light is perceived by a human looking at the molded or continuously cast surface materials. Thus, the first three (3) functions of the '956 patent address a photometry problem and not a radiometry problem. As previously noted herein, radiometry is the science of measuring radiation energy in any portion of the electromagnetic spectrum photometry, and photometry is the science of measuring visible radiation according to the sensitivity of the human eye. For example, the '956 patent teaches including a diffusion layer to provide "a uniformly lighted appearance at viewing surface 308 of material 302." However, controlling how uniformly the LED light generated in the '956 patent is perceived by a human does not teach or require maintaining the light irradiance level at the viewing surface 308 above a predetermined minimum, and also does not teach or require that light passing through one or more predetermined regions of the viewing surface 308 is maintained at or above a minimum irradiance level that neutralizes infectious agents with no non-sanitized regions in the predetermined region(s).

An initial distinction between the self-sanitizing structure disclosed herein and what is taught by the '956 patent is that the primary variables that determine how light appears to the human eye are the background contrast and radiance of the light. Applying this to the '956 patent, the primary variable that determine how light appears to the human eye are the background contrast provided by the viewing surface 308, as well as the radiance of the LED light. In contrast to irradiance, which is a variable controlled by a self-sanitizing structure in accordance with aspects of the invention, radiance is a measure of the rate at which light energy is emitted from the viewing surface 308 in a particular direction. Hence, the light control techniques described in the '956 patent manage variables that are different from the variables managed by the light control techniques implemented in connection with a self-sanitizing structure in accordance with aspects of the invention.

An additional distinction between a self-sanitizing structure in accordance with aspects of the invention and what is taught by the '956 patent is that, because the human eye cannot detect features below certain dimensions, and because the goal of the '956 patent is a uniform human perception of LED light at the viewing surface 308, the '956 patent does not teach or suggest ensuring that the viewing surface 308 has uniform light irradiance. In other words, once the size of non-sanitized regions (i.e., regions with no or low light irradiance) on the viewing surface 308 of the '956 patent are below what a human eye can perceive (i.e., below the visual resolution of the human eye), light at the viewing surface 308 will be perceived uniformly by a human even though the irradiance level of light at the viewing surface 308 is in fact not uniform. This is analogous to the way discrete pixels and subpixels on a display are blended by the human eye into an illusion of a single, clear picture. Hence, the recited goal in the '956 patent of "a uniformly lighted appearance at viewing surface 308" does not teach or require maintaining the light irradiance level at the viewing surface 308 above a predetermined minimum, and also does not teach or require that light passing through one or more predetermined regions of the viewing surface 308 is maintained at or above a minimum irradiance level that neutralizes infectious agents with no non-sanitized regions in the predetermined region(s).

With respect to the fourth (4$^{th}$) LED function described in the '956 patent ("aiding sanitation as in the use of embedded ultraviolet lighting units for the purpose of killing pathogens on the surface of a counter"), the '956 patent does not disclose or suggest what role, if any, the counter itself plays in achieving sanitization at the surface of the counter; does not disclose or suggest maintaining the light irradiance level at the viewing surface 308 above a predetermined minimum; and does not disclose or suggest that light passing through one or more predetermined regions of the viewing surface 308 is maintained at or above a minimum irradiance level required in order to neutralizes infectious agents with no non-sanitized regions in the predetermined region(s).

Continuing with the overview of aspects of the invention, in some embodiments of the invention, the sanitizing light is blue and/or purple light, and the light/wavelength attenuation and/or absorption characteristics of the body region make the body region semitransparent to blue and/or purple light. Exposure to blue/purple light that is above the minimum irradiance that neutralizes infectious agents has much less severe impact on human health than exposure to UV light, depending on the irradiance level and duration of the blue/purple light exposure.

As previously noted herein, in some embodiments of the invention, the coverage area or footprint of the sanitizing light on the contact/exit surface can be controlled by the placement and configuration (or placement pattern) of the light sources of the self-sanitizing structure. In some aspects of the invention, the light source can be implemented as a single light source. In some aspects of the invention, the light source can be implemented as multiple discrete light sources. In aspects of the invention where the light source is implemented as multiple discrete light sources, the discrete light sources can be configured in an array pattern, and multiple light source arrays and array patterns can be provided. In aspects of the invention where the light source is implemented as an array of multiple discrete light sources, the discrete light sources can be addressable, and a processor can be programmed to selectively activate and deactivate the addressable discrete light sources to selectively target portions of the exit surface for sanitization. In some aspects of the invention, a sensor system (e.g., pressure/force sensors, capacitive sensors, and the like) can be used to identify the selected regions of the exit surface as commonly-touched regions. In some embodiments of the invention, the light source arrays can be configured and arranged such that a footprint of the sanitizing light that passes through the body region and reaches the contact/exit surface covers substantially all of the structure's exit surface.

In some embodiments of the invention, the self-sanitizing structure can be configured to implement the previously-described sensor system as touch-based sensor elements configured to capture "touch data" (e.g., time, location, and the like) when a user touches the contact/exit surface. In aspects of the invention, the previously-described highly-touched surface regions can be identified using the touch-based sensor elements. In some aspects of the invention, the touch-based sensor elements can be implemented as force sensors. In some aspects of the invention, the touch-based sensor elements can be implemented as substantially translucent capacitive-touch sensors configured and arranged to detect and record the touch data as capacitance changes that result from a user touching the contact/exit surface. In embodiments of the invention, the capacitive-touch sensors can be translucent and positioned between the light source(s) and the structure's exit surface. In some embodiments of the invention, the sensor elements can be implemented as a combination of force sensors and capacitive-touch sensors. In aspects of the invention, the touch data generated by the sensor elements can be logged in memory then accessed and used by a processor to control the discrete light sources based on the touch data. In some aspects of the invention, the processor is configured to, based on the touch data, only activate the discrete light sources (or light arrays) that direct sanitizing light to the portions of the contact/exit surface that are above the sensor elements that have been activated over a predetermined period of time, or that have been activated since a prior sanitizing operation.

Accordingly, a self-sanitizing structure in accordance with embodiments of the invention provides technical effects that are an improvement over known methods of sanitizing commonly touched environmental surfaces. For example, the sanitization functions performed in accordance with embodiments of the invention are not labor intensive; do not damage environmental surfaces; are not susceptible to human error in the application thereof; do not require precise controls in order to prevent harm to the humans; provide computer-implemented controls of when and for how long sanitization functions are performed; provide computer-implemented controls of what portion(s) of the environmental surface receive treatment; and provide computer-implemented recording of data related to various aspects of when and where surfaces have been touched and treated, which enables the creation of reports that track compliance with government and non-government sanitization guidelines.

Further, a self-sanitizing structure in accordance with embodiments of the invention does not require that intended functions of the contact/exit surface are interrupted in order to apply the surface sanitization methods of the self-sanitizing structure. Referring again to the previously described example in which a conference room with a conference table is being used to host a three (3) day seminar, where the conference table has been implemented as a self-sanitizing structure in accordance with embodiments of the invention, the conference table is configured and arranged to sanitize its main surface from within or below the conference table's main support surface. Accordingly, the self-sanitizing conference table performs its self-sanitizing operations without interrupting the intended function of the main support surface of the conference table. More specifically, a self-sanitizing conference table in accordance with embodiments of the invention can be used to sanitize the conference table's main support surface without requiring the removal of all items from the conference table's main support surface. Hence, a self-sanitizing conference table in accordance with embodiments of the invention does not interrupt the intended function(s) of the surface being sanitized.

Turning now to a more detailed description of aspects of the invention, FIG. 1 depicts a simplified diagram illustrating a self-sanitizing structure 100 having a contact surface 102, a body region 106, and an integrated self-sanitizing system 130, configured and arranged as shown. The self-sanitizing structure 100 can be communicatively coupled (wired or wirelessly) to remote systems 140 according to embodiments of the invention. In embodiments of the invention, the remote systems 140 include various processor systems and/or power systems communicatively coupled to the self-sanitizing structure 100. In some embodiments of the invention, some or all of the functionality of the remote systems 140 can be incorporated within the self-sanitizing structure 100, and more specifically can be incorporated within the integrated self-sanitizing system 130.

In some embodiments of the invention, the remote systems 140 can include a cloud computing system in wired or wireless electronic communication with one or all of the components of the self-sanitizing structure 100. The cloud computing system can supplement, support or replace some or all of the electronic and/or processor functionality of the self-sanitizing structure 100. Additionally, some or all of the functionality of the components of the self-sanitizing structure 100 can be implemented as a node of the cloud computing system.

In some embodiments of the invention, the body region 106 and the self-sanitizing system 130 can be substantially nonflexible or substantially rigid materials. In some embodiments of the invention, the body region 106 and the self-sanitizing system 130 can be substantially flexible and relatively thin structures or sheets. In some embodiments of the invention, the body region 106 and the self-sanitizing system 130 can include a combination of substantially rigid materials and substantially flexible portions. The features and functions of the various implementations of the self-sanitizing structure 100 described herein apply to both substantially rigid and substantially flexible implementations of the body region 106 and the self-sanitizing system 130 unless specifically limited to either a substantially rigid implementation and/or a substantially flexible implementation.

In aspects of the invention, the contact surface 102 is configured and arranged such that it can be touched by humans when the self-sanitizing structure 100 is being used to perform its intended function(s) (e.g., functioning as a bedtable or a flexible wall covering). In some aspects of the invention, high-touch sub-regions 102A can optionally be identified as sections of the contact surface 102 that are exposed to human touch at a higher level/rate than other parts of the contact surface 102. For example, where the structure 100 is implemented as a conference table, high-touch sub-regions 102A can be regions on the perimeter of the table's main support surface where humans are most likely to touch the main support surface when seated at the conference table. In some aspects of the invention, the high-touch sub-regions 102A can be identified and targeted to receive sanitizing light by using a local sensor system 126 (shown in FIGS. 3 and 4) and a local processor 120 (shown in FIG. 2A) of the integrated self-sanitizing system 130. Additional details of the local sensor system 126 and the local processor 120 are provided subsequently herein. Because the contact surface 102 is commonly touched by humans, infectious agents (e.g., microbes, protozoa, bacteria, viruses, and the like) can persist on the contact surface 102 long enough for the contact surface 102 to act as conduits for indirect transfer of the infectious agent from one person to another.

In accordance with aspects of the invention, the integrated self-sanitizing system 130 is covert in that it is integrated with the self-sanitizing structure 100 in a manner that enables the self-sanitizing structure 100 to sanitize the contact surface 102 without interfering with the intended function of the self-sanitizing structure 100. In embodiments of the invention, the self-sanitizing structure 100 and the integrated self-sanitizing system 130 include light sources 112, 112A (shown in FIGS. 2A-2C) that transmits light 116 (shown in FIGS. 3 and 4) through the body region 106 to the contact surface 102. In some embodiments of the invention, the light 116 is transmitted as a continuous wave. In some embodiments of the invention, the light 116 is transmitted as a series of pulses having a controlled pulse width, frequency and/or duty cycle. Because the light 116 exits the self-sanitizing structure 100 through the contact surface 102, the contact surface 102 is also referred to as an exit surface. In accordance with aspects of the invention, sanitization characteristics and/or properties of the self-sanitizing structure 100 are configured and arranged to control the light 116 that passes through the body region 106 and the exit surface 102 in a manner that maintains irradiance of the light 116 that reaches the exit surface 102 at or above a minimum irradiance level that will neutralize infectious agents on the exit surface 102.

As previously noted herein, the terms "sanitizing light" refer to light that is maintained at or above a minimum irradiance level required to neutralize infectious agents. As also previously noted herein, the terms "sanitization characteristics" or "sanitization properties" refer to characteristics/properties of the self-sanitization structure 100 that have been controlled in a manner that maintains light that passes through the exit surface 102 at or above a minimum irradiance level that will neutralize infectious agents with no non-sanitized regions 310 (shown in FIG. 5C) on the contact/exit surface 102. As previously noted herein, the terms "non-sanitized region" refer to regions of the contact/exit surface 102 where light irradiance is below a minimum irradiance level that will neutralize infectious agents.

The diagrammatic representation of the self-sanitizing structure 100 is simplified in that the self-sanitizing structure 100, the body region 106, the commonly touched contact/exit surface 102, and the high-touch sub-regions 102A collectively represent a wide variety of structures that have one or more commonly touched and/or highly touched surfaces, and that can be configured to include the integrated self-sanitizing system 130 in accordance with embodiments of the invention. Non-limiting examples of how the body region 106 of the self-sanitizing structure 100 can be implemented include but are not limited to a fixed or portable over-bed table; a so-called swinging traffic door that has no door handle but is opened by pushing against the door panel; a so-called "smart wall" suitable for use in a variety of building structures including, for example, a home or a conference room of an office building; a substantially flexible body region formed as a multi-layered flexible sheet attached as a covering to another structure such as a wall or a door handle or an arm rest of a chair; commonly touched surfaces of an airplane cabin; service counters and tables in a restaurant; prescription counters and checkout stations at grocery stores and pharmacies; any and all surfaces in a medical care facility including bed rails, bathroom counters, bathroom walls, sink and wash stations, showers, water flow and lighting controls, switch plates, door handles, instruments, the inside of magnetic resonance image (MRI) instruments, and phlebotomist stations; hotel surfaces including bedside tables, doorways, door handles, bathroom fixtures, toilet seats, shower stalls; remote controls or any personal electronic device such as a smart phone or a tablet; surfaces in sports facilities including stadium seating and bathrooms; and/or personal protection garments such as gloves, facemasks, automobile steering wheels, dashboards, shift sticks, and door handles.

FIGS. 2A-19 depict various features and functionality of the self-sanitizing structure 100 shown in FIG. 1. In accordance with aspects of the invention, although some of the features and functionality of the self-sanitizing structures shown in FIGS. 2A-19 are described separately from one another, unless otherwise stated herein, any feature or function of any self-sanitizing structure (e.g., self-sanitizing structures 100A-100J, 1500, and 1700) described and illustrated herein can be combined with any other feature or function of the self-sanitizing structures described and illustrated herein. For example, the flexible fibrous element layer(s) 206B (shown in FIG. 2C) can be utilized as the scattering elements 106B (shown in FIG. 2B) of a substantially nonflexible or substantially rigid implementation of the body region 106 of the self-sanitizing structure 100. As another example, although various examples of the scattering elements 106B are described separately herein, the example scattering elements 106B are not mutually exclusive and can be combined.

Figure 2A:
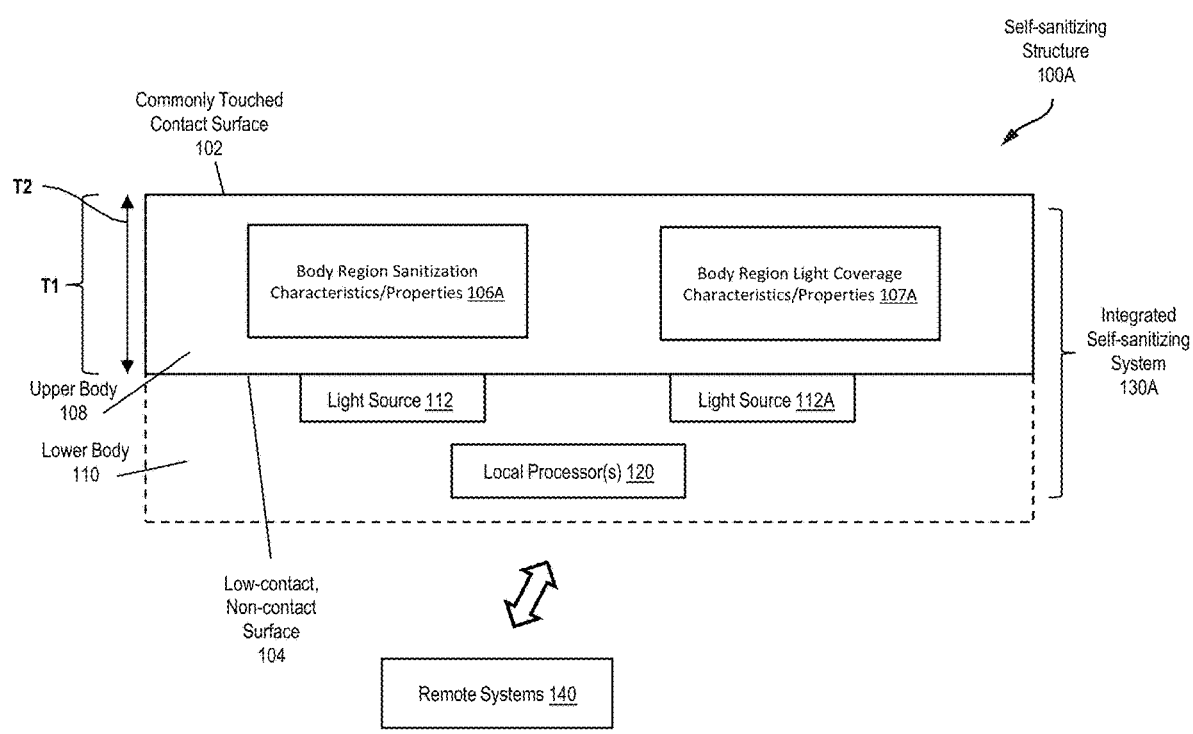
FIG. 2A depicts an example cross-sectional view of the self-sanitizing structure shown in FIG. 1, which is taken along line X-X and depicts additional details of the structure in accordance with embodiments of the invention.

FIG. 2A depicts a self-sanitizing structure 100A, which is a cross-sectional view of the self-sanitizing structure 100 taken along line X-X shown in FIG. 1. In accordance with aspects of the invention, the self-sanitizing structure 100A includes all of the features and functionality of the self-sanitizing structure 100 and adds details of how certain features and functionality of the self-sanitizing structure 100 can be implemented. The self-sanitizing structure 100A includes an upper body 108, a lower body 110, and an integrated self-sanitizing system 130A. In accordance with aspects of the invention, the body region 106 (shown in FIG. 1) can be implemented to include the upper body 108 and the lower body 110; and the integrated self-sanitizing system 130 (shown in FIG. 1) can be implemented as the integrated self-sanitizing system 130A. The use of a dotted line to define the lower body 110 in FIG. 2A indicates that, in some embodiments of the invention, the lower body 110 can be omitted, and the structures (e.g., the light sources 112, 112A and the local processor(s) 120) depicted in the lower body 110 can be attached to a low-contact, non-contact surface 104 of the upper body 108.

In embodiments of the invention, the upper body 108 includes the commonly touched contact/exit surface 102 and, optionally, the high-touch sub-regions 102A (shown in FIG. 1). In embodiments of the invention, the upper body 108 can further include the low-contact, no-contact surface 104, configured and arranged as shown. In some aspects of the invention, the self-sanitizing structure 100A can include elements configured and arranged to substantially protect the surface 104 from being contacted by humans. In some aspects of the invention, the upper body 108 and the lower body 110 can include elements configured and arranged to substantially limit the amount of contact that humans can make with the surface 104. The upper body 108 and the lower body 110 can be mechanically secured to protect the integrated self-sanitizing system 130A. In some embodiments of the invention, the upper body 108 and the lower body 110 can include disassembly elements configured to allow the upper body 108 and the lower body 110 to be disassembled so the integrated self-sanitizing structure 130A can be tested and/or repaired. In some embodiments of the invention, the integrated self-sanitizing system 130A is embedded within the upper body 108 and the lower body 110; hermetically sealed within the upper body 108 and the lower body 110; and/or seamed between the upper body 108 and the lower body 110. In some embodiments of the invention, the light sources 112, 112A, local processor 120, and other elements of the integrated self-sanitizing system 130A can be formed on one or more substrates that are laminated or adhered to the low-contact, non-contact surface 104 between the upper body 108 and the lower body 110; and/or seamed between the upper body 108 and the lower body 110.

In embodiments of the invention, the integrated self-sanitizing system 130A includes a local processor 120, light sources 112, 112A, the sanitization characteristics/properties 106A, and light coverage (or light footprint) characteristics/properties 107A. In embodiments of the invention, the sanitization characteristics/properties 106A are the sanitization characteristics/properties of the portion of the body region 106 (shown in FIG. 1) that is between the light sources 112, 112A and the contact surface 102. In the integrated self-sanitizing system 130A, the light sources 112, 112A are within the lower body 110 and substantially positioned at an interface between the upper body 108 and the lower body 110. Accordingly, the sanitization characteristics/properties 106A are the sanitization characteristics/properties of the upper body 108. In embodiments of the invention, the light coverage characteristics/properties 107A are the properties of the body region 106 that shape the footprint of the sanitizing light 116 (shown in FIGS. 3 and 4) that reaches the contact/exit surface 102. In some embodiments of the invention, the light coverage characteristics/properties 107A can be controlled by any combination of a distance T2 from the light sources 112, 112A to the contact/exit surface 102; lens elements 107B (shown in FIG. 2B); diffuser elements 107C (shown in FIG. 2B); the topography (or roughness) of the contact/exit surface 102; the internal topography (or roughness) of the body region 106 (shown in FIG. 1); the size of the light sources 112, 112A; the number of light sources 112, 112A; and/or a placement pattern of the light sources 112, 112A. In embodiments of the invention, there can be some overlap between the body region sanitization characteristics/properties 106A and the body region light coverage characteristics/properties 107A.

For ease of illustration, only two (2) light sources 112, 112A are depicted. However, in embodiments of the invention, any number of the light sources 112, 112A can be provided. In some aspects of the invention, the light sources 112, 112A can be implemented as a single light source. In some aspects of the invention, each of the light sources 112, 112A can be implemented as a set of multiple discrete light sources. In aspects of the invention where each of the light sources 112, 112A is implemented as a set of multiple discrete light sources, the set of discrete light sources can be configured in an array pattern, and multiple light source arrays and array patterns (e.g., LED array 700 shown in FIG. 7) can be provided. In aspects of the invention where each of the light source 112, 112A is implemented as an array of multiple discrete light sources, the discrete light sources can be addressable, and the local processor 120 can be programmed to selectively activate and deactivate the addressable discrete light sources to selectively target portions of the contact/exit surface 102 for sanitization.

Figure 15A:
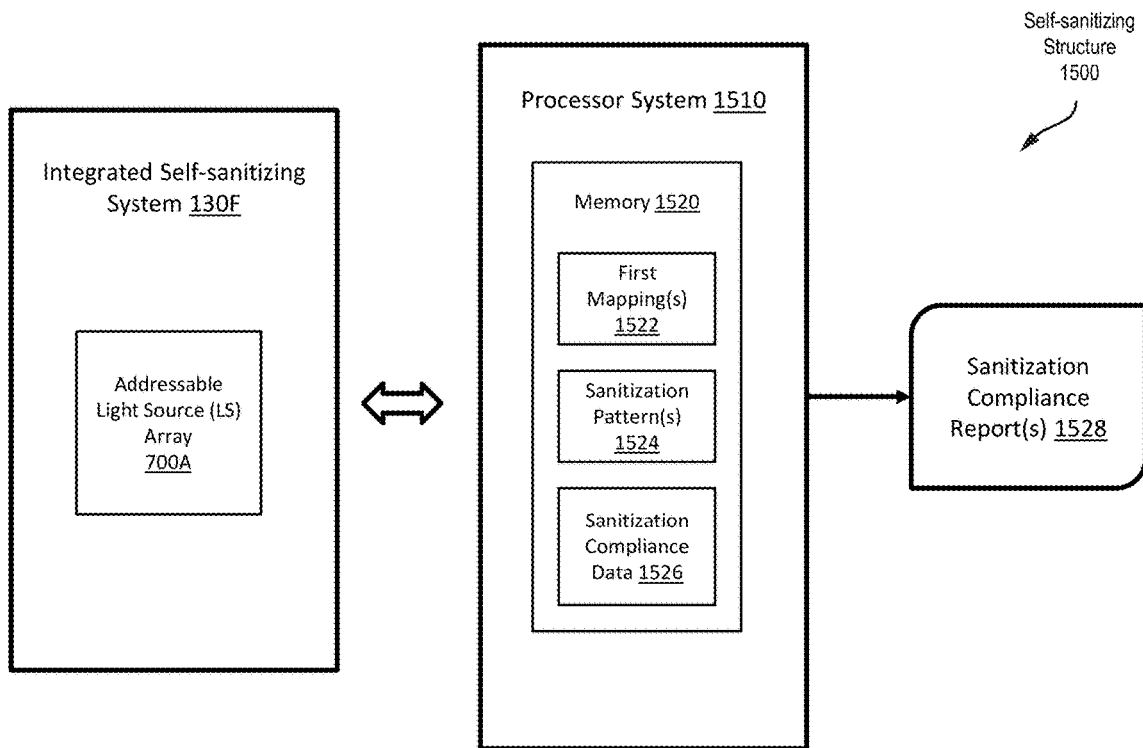
FIG. 15A depicts a block diagram illustrating portions of a self-sanitizing structure in accordance with embodiments of the invention.
Figure 15B:
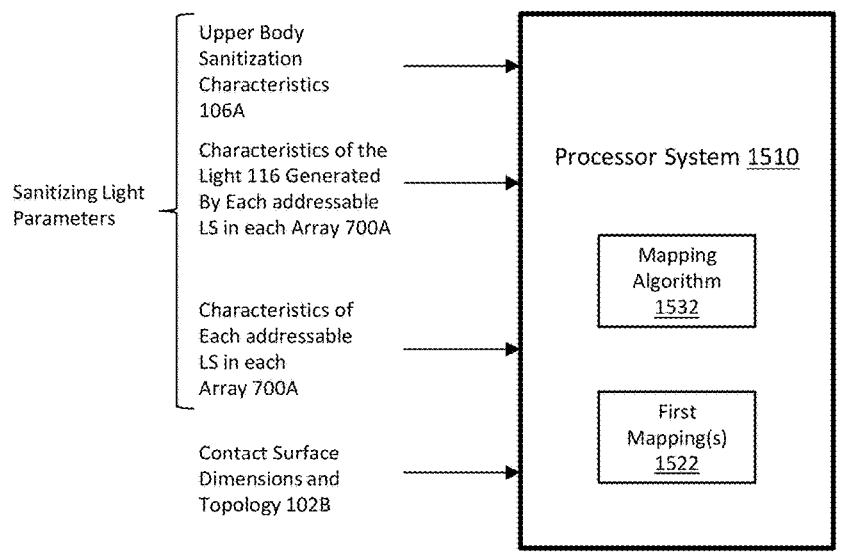
FIG. 15B depicts example inputs and outputs of a processor configured to execute aspects of the present invention.
Figure 15C:
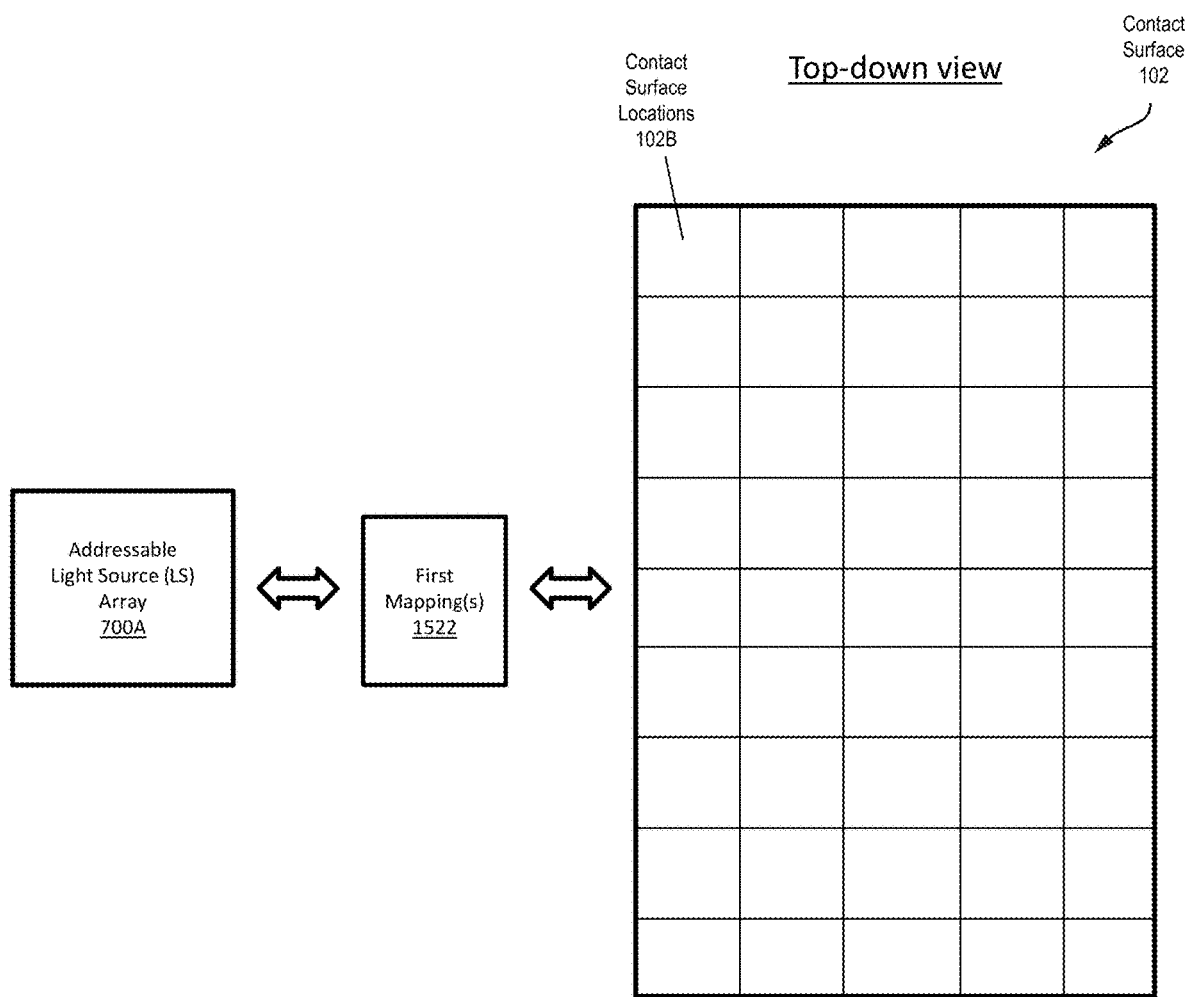
FIG. 15C depicts an example of how a first mapping can be implemented in accordance with embodiments of the invention.
Figures 15D, 15E:
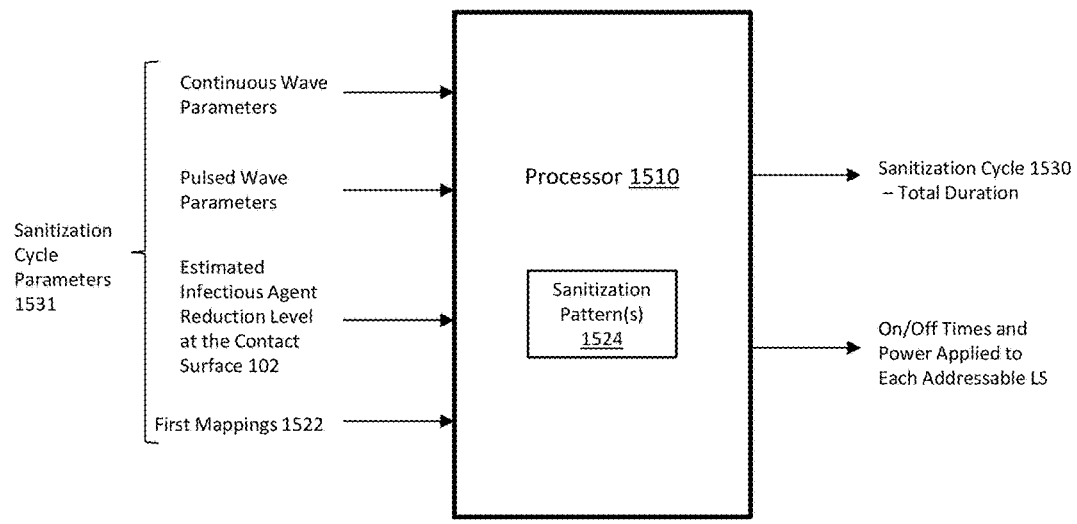
FIG. 15D depicts example inputs and outputs of a processor configured to execute aspects of the present invention.
FIG. 15E depicts a sanitization pattern in accordance with aspects of the present invention.
Figure 17A:
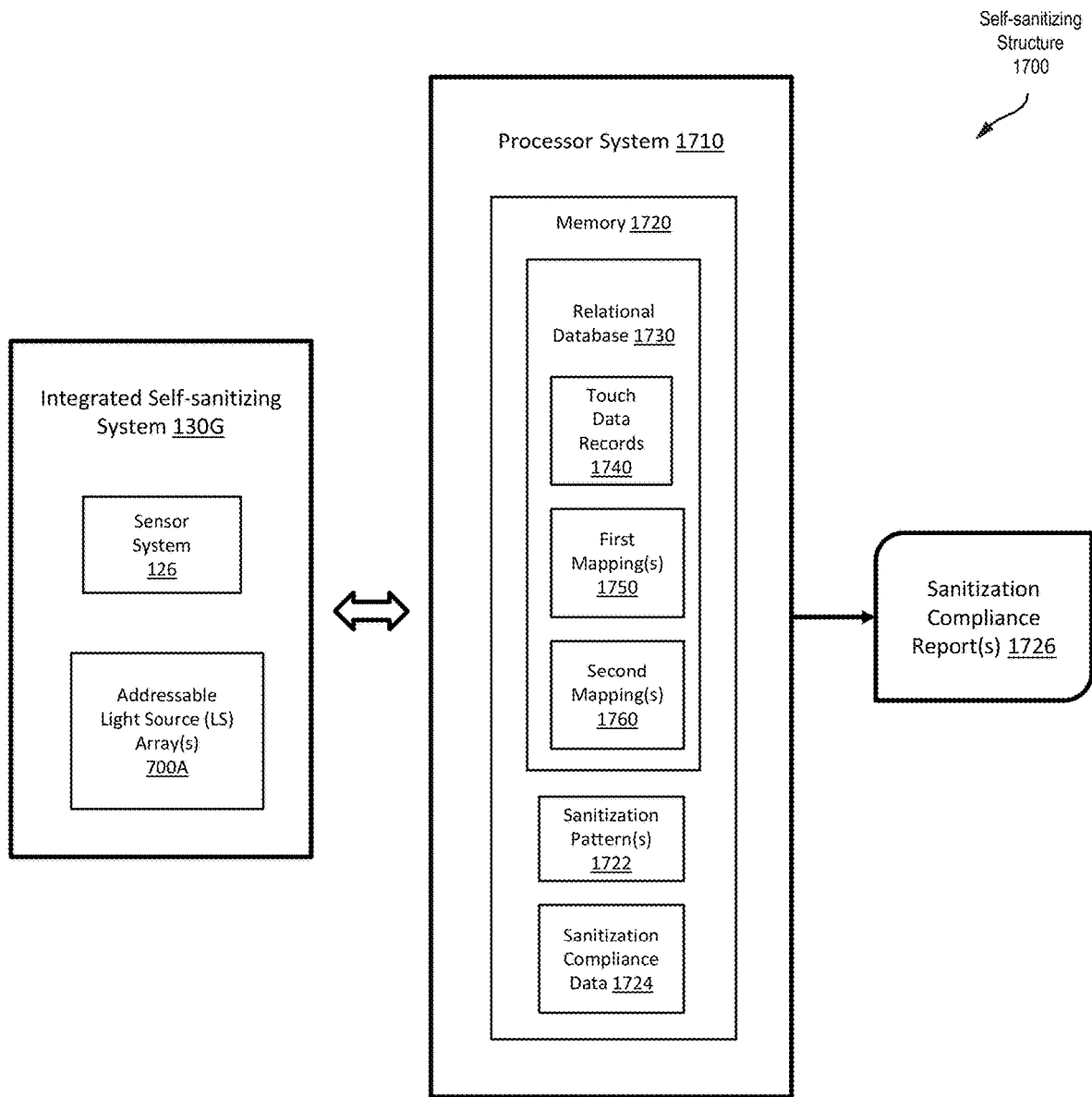
FIG. 17A depicts a block diagram illustrating portions of a self-sanitizing structure in accordance with embodiments of the invention.
Figure 17B:
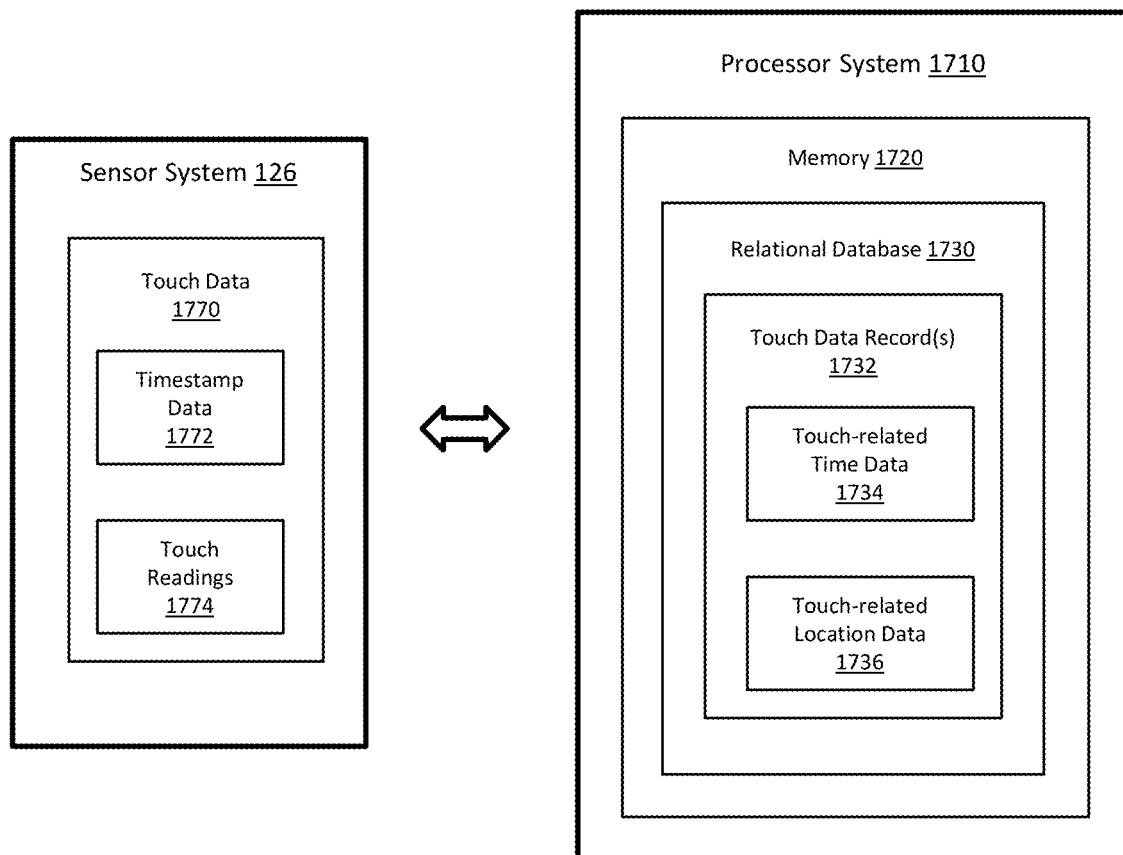
FIG. 17B depicts a block diagram illustrating portions of a self-sanitizing structure in accordance with embodiments of the invention.
Figure 17C:
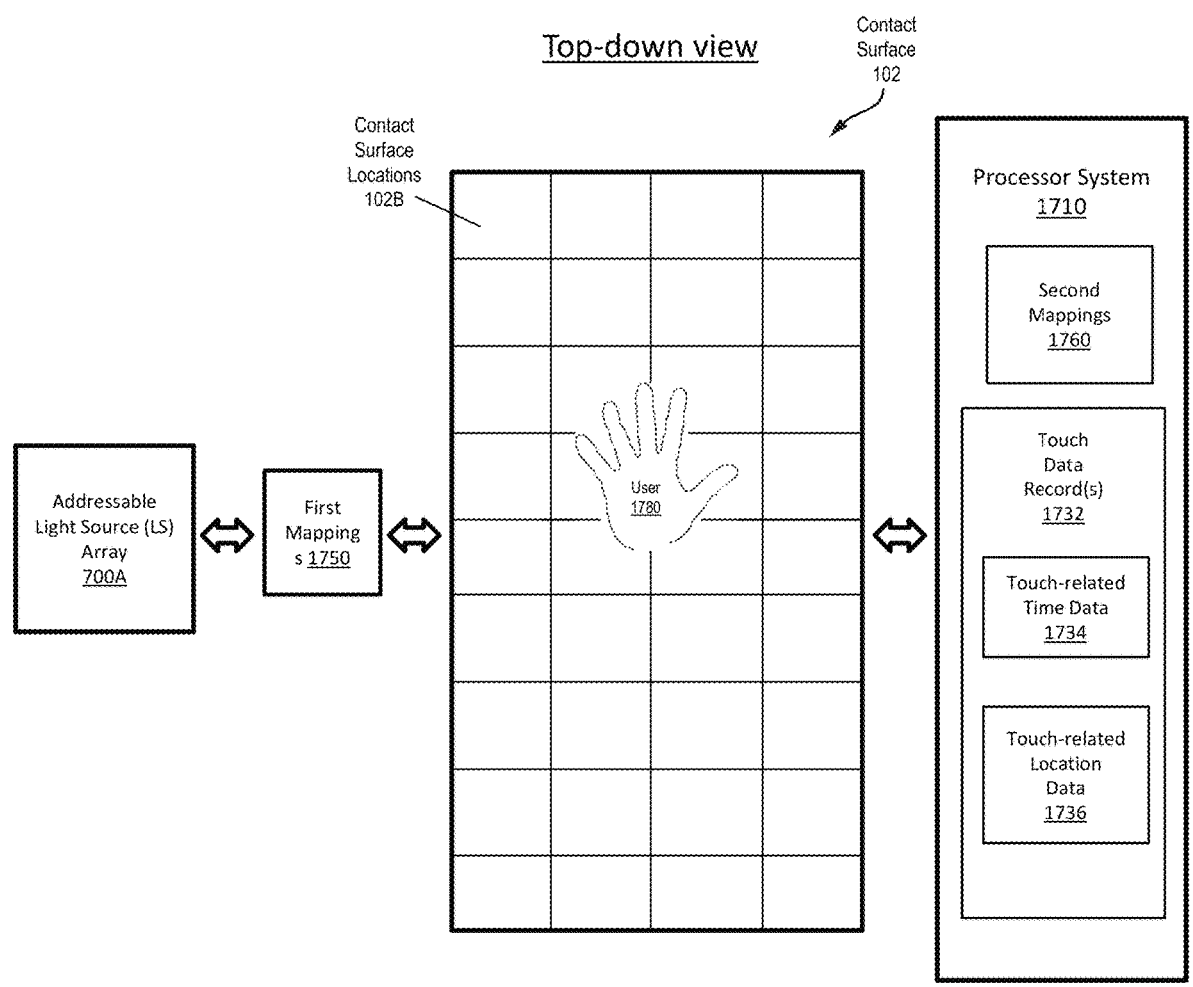
FIG. 17C depicts a block diagram illustrating individual addressable light sources (LSs) of an LS array mapped to locations on a contact surface of a self-sanitizing structure in accordance with embodiments of the invention.
Figures 17D, 17E:
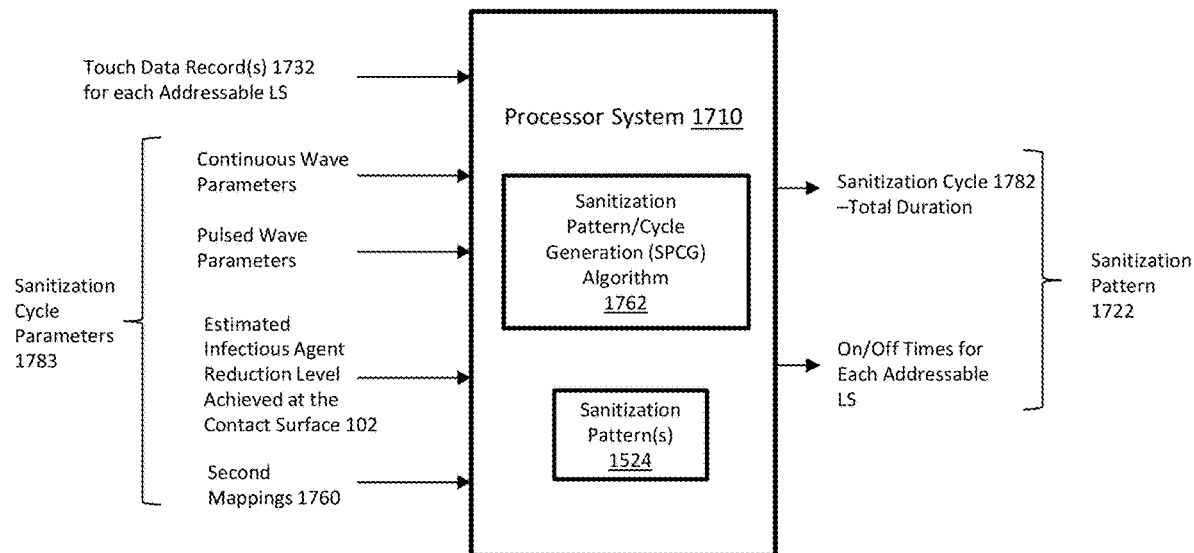
FIG. 17D depicts example inputs and outputs of a processor configured to generate a sanitization pattern in accordance with aspects of the invention.
FIG. 17E depicts a sanitization pattern in accordance with aspects of the invention.

In accordance with aspects of the invention, the integrated self-sanitizing system 130A initiates and controls the execution of a sanitization cycle (e.g., sanitization cycles 1530, 1782 shown in FIGS. 15D and 17D). In aspects of the invention a sanitization cycle can be initiated by the processor 120 controlling the light sources 112, 112A such that they generate light that is scattered and dispersed by the sanitization characteristics/properties 106A of the upper body 108 in a manner that generates sanitizing light at the contact/exit surface 102. As previously noted herein, sanitizing light is light having a wavelength and irradiance level that is above a minimum level that will neutralize infectious agents. In embodiments of the invention, the processor 120 can control the light sources 112, 112A such that the light they generate can be continuous wave light or pulsed light having a controlled pulse width, frequency and/or duty cycle. In some embodiments of the invention, the light sources 112, 112A are configured and arranged to generate blue and/or purple light within a wavelength range from about 380 nm to about 500 nm, and the minimum irradiance level of blue/purple light used to neutralize infectious agents can be about 0.5 mW/cm$^2$. In some embodiments of the invention, the minimum irradiance level of blue/purple light used to neutralize infectious agents can be about 1 mW/cm$^2$.

In accordance with aspects of the invention, the processor 120 is configured to continue the sanitization cycle (e.g., sanitization cycles 1530, 1782 shown in FIGS. 15D and 17D) for a sanitation cycle duration, which is a period of time that is estimated (e.g., by the processor 120) to achieve a desired infectious agent reduction level on the contact surface 102. For example, the desired infectious agent reduction level on the contact surface 102 can be selected to meet the guidelines set forth by the United States Environmental Protection Agency (EPA) for disinfectants, which is an infectious agent reduction level of about 99.9999% (a 6-log reduction). In embodiments of the invention, the processor 120 is configured to determine the sanitization cycle duration based on a variety of sanitization cycle parameters (e.g., sanitization cycle parameters 1531, 1783 shown in FIGS. 15D and 17D). In some embodiments of the invention, the sanitization cycle parameters can include an estimate of the infectious agent reduction level achieved at the contact surface 102; whether the light sources 112, 112A transmit continuous wave or pulsed light; and/or characteristics of the continuous wave or pulsed light generated by the light sources 112, 112A. In embodiments of the invention, the estimated infectious agent reduction level achieved at the contact surface 102 can be determined based at least in part on any combination of a thickness T1 of the upper body 108; a distance T2 from each of the light sources 112, 112A to the contact surface 102; characteristics of the light 116 (shown in FIGS. 3-5C) generated by the light sources 112, 112A; whether the light sources 112, 112A transmit continuous wave or pulsed light; characteristics of the continuous wave or pulsed light generated by the light sources 112, 112A; characteristics of the light sources 112, 112A; and/or the body region sanitization characteristics/properties 106A.

In some embodiments of the invention, some of the sanitization cycle parameters can be selected by a user of the integrated self-sanitizing system 130A. For example, the processor 120 can be configured to allow the user to select power levels applied to the light sources 112, 112A, which influences where the irradiance level of the light 116 falls between a minimum light irradiance level 116A and an upper-end irradiance level 116B (shown in FIG. 5A), which is a characteristic of the light sources 112, 112A and the light 116. In some embodiments of the invention, the processor 120 can be configured to allow the user to select a desired infectious agent reduction level and/or the characteristics of the continuous wave or pulsed light. In some embodiments of the invention, a variety of sanitization cycle parameters and resulting sanitization cycles can be predetermined and presented to a user in a menu; and the user can select the sanitization cycle duration from the sanitization cycle duration options presented in the menu. Additional details of how a sanitization cycle can be controlled in accordance with aspects of the invention are depicted in FIGS. 15A-18 and described in greater detail subsequently herein.

Figure 2B:
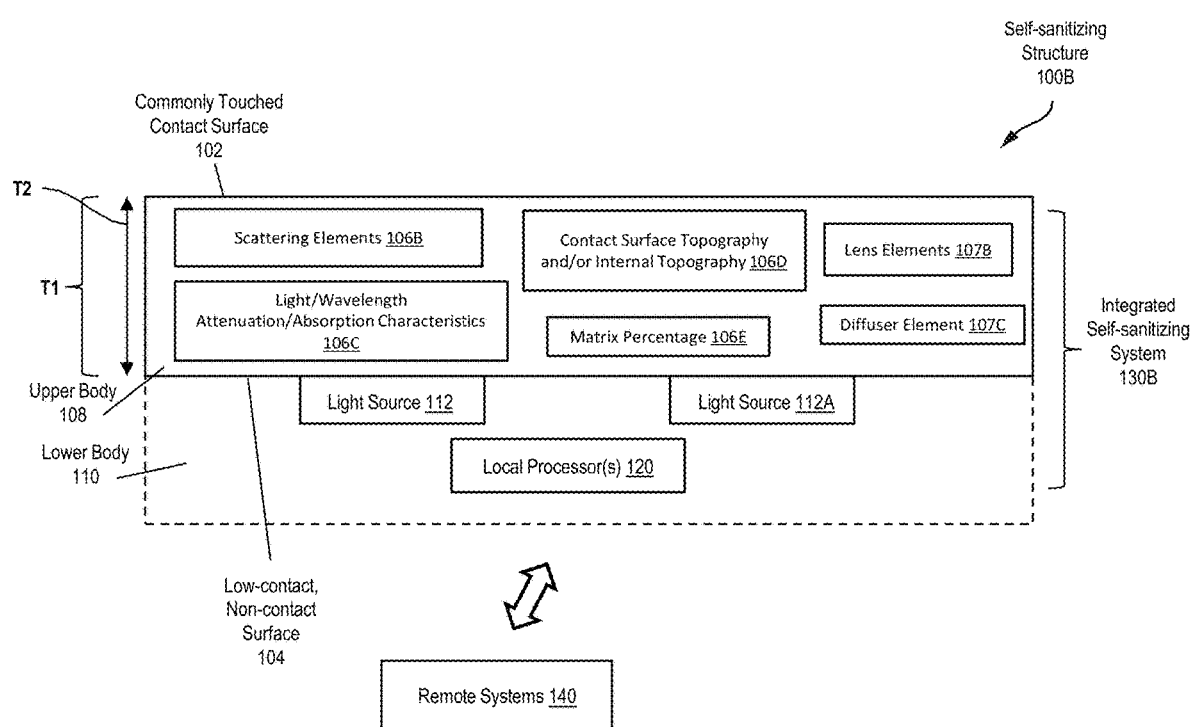
FIG. 2B depicts another example cross-sectional view of the self-sanitizing structure shown in FIG. 1, which is taken along line X-X and depicts additional details of the structure in accordance with embodiments of the invention.

FIG. 2B depicts a self-sanitizing structure 100B, which is a cross-sectional view of the self-sanitizing structure 100 taken along line X-X of FIG. 1. In accordance with aspects of the invention, the self-sanitizing structure 100B includes all of the features and functionality of the self-sanitizing structure 100A (shown in FIG. 2A) and adds details of how certain features and functionality of the self-sanitizing structure 100A can be implemented. The self-sanitizing structure 100B includes an integrated self-sanitizing system 130B that is substantially the same as the integrated self-sanitizing system 130A (shown in FIG. 2A) except the integrated self-sanitizing system 130B includes details of how the body region sanitization characteristics/properties 106A (shown in FIG. 2A) and the body region light coverage (or light footprint) characteristics/properties 107A (shown in FIG. 2A) can be implemented. More specifically, the body region sanitization characteristics/properties 106A are implemented as scattering elements 106B that can be, optionally, combined with one or more of light/wavelength attenuation/ absorption characteristics/properties 106C; contact surface topography (or roughness) and/or internal topography (or roughness) 106D; and a percentage of the body region 106 or the upper body 108 that is matrix material (i.e., matrix percentage 106G). As used herein, the notation "light/ wavelength" is used to refer to a range of relevant light properties, including but not limited to the light's wavelength. Additionally, the body region light coverage characteristics/properties 107A can be implemented as lens elements 107B and/or diffuser elements 107C. FIG. 2E depicts tables A and B illustrating examples of the sanitization characteristics/properties 106A and the light coverage/footprint characteristics/properties 107A that can be utilized in accordance with embodiments of the invention.

In some embodiments of the invention, the sanitization characteristics/properties 106A (shown in FIG. 2A) of the self-sanitizing structure 100B can include any combination of the presence of spaced-apart scattering elements 106B in the upper body 108; a size distribution (or diameter-size distribution) of the spaced-apart scattering elements 106B in a matrix material of the upper body 108; spacing between the spaced-apart scattering elements 106B in the matrix material of the upper body 108; a refractive index of the matrix material of the upper body 108; a difference between the refractive index or indices of the spaced-apart scattering elements 106B and the refractive index of the matrix material of the upper body 108; a percentage of the upper body 108 that is the spaced-apart scattering elements 106B; a percentage of the upper body 108 that is the matrix material; a refractive index or indices of the matrix material of the upper body 108. In some embodiments of the invention, the size of each of the spaced-apart scattering elements 106B, as well as the difference between the refractive index or indices of the spaced-apart scattering elements 106B and the refractive index of the matrix material of the upper body 108, are sufficient to scatter the electromagnetic radiation; and the spacing between the spaced-apart scattering elements 106B in the upper body 108 is sufficient to enable the scattered electromagnetic radiation to pass through the upper body 108 to the contact surface 102. In embodiments of the invention, the scattering elements 106B have sufficient size to scatter light, which is from about 50 nanometers in diameter to about 50 micrometers in diameter, assuming there is a sufficient index of refraction mismatch between the scattering elements 106B and the surrounding matrix material of the upper body 108. In accordance with aspects of the invention, the matrix material can be implemented as a homogeneous and monolithic material in which the scattering elements 106B and any additional filler materials are embedded to form a composite. The matrix material provides a medium for binding and holding the scattering elements 106B and any additional filler elements together into a solid (which can be rigid or flexible). In some embodiments of the invention, the matrix material can be a substantially rigid/flexible polymer matrix material. In some embodiments of the invention, the substantially rigid/flexible polymer matrix material can be a substantially rigid/ flexible PMMA material. In some embodiments of the invention, suitable materials for the matrix material of the upper body 108 include the matrix materials used in various grades and colors of solid surface materials sold under the tradename Corian® (including but not limited to Glacier Ice Corian®), as well as the matrix materials used in various grades and colors of multi-layered flexible material sold under the tradename Tedlar® Wallcoverings.

In embodiments of the invention, the scattering elements 106B have a size distribution sufficient to scatter light, which is from about 50 nanometers in diameter to about 50 micrometers in diameter, assuming there is a sufficient index of refraction mismatch between the scattering elements 106B and a surrounding matrix material of the upper body 108. In some embodiments of the invention, the scattering elements 106B used in the upper body region 108 can be pigments, examples of which include aluminum trihydrate, titanium dioxide, and zinc oxide. In some embodiments of the invention, the scattering elements 106B are photosensitizing pigments configured and arranged to enhance sanitization by either color shifting the light 116 or creating reactive oxygen species on the contact surface 102. In some embodiments of the invention, the scattering elements 106B are dyes, examples of which include methylene blue and rose Bengal. In some embodiments of the invention, the scattering elements 106B are fibrous elements 208 (shown in FIG. 2D), which can be implemented as fibers 210, micro-fibers 212, and/or a combination of the fibers 210 and the micro-fibers 212 (all of which are shown in FIG. 2D).

Figure 2C:
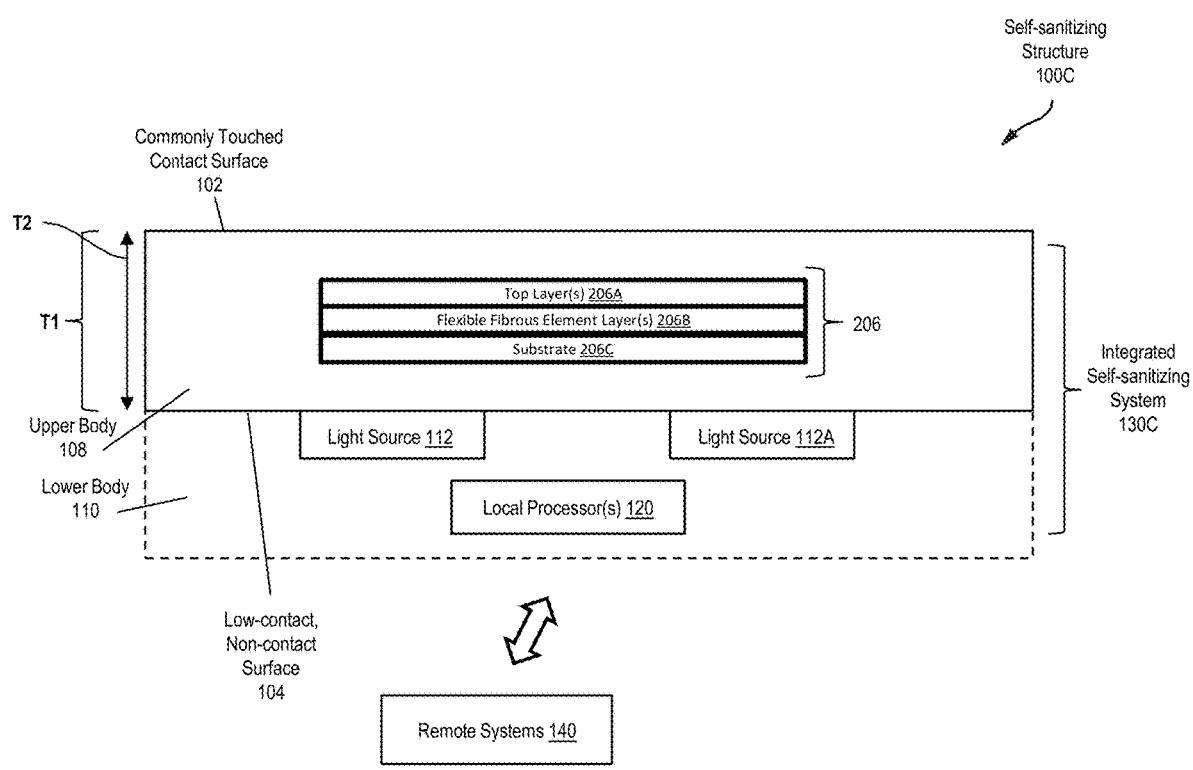
FIG. 2C depicts another example cross-sectional view of the self-sanitizing structure shown in FIG. 1, which is taken along line X-X and depicts additional details of the structure in accordance with embodiments of the invention.

FIG. 2C depicts a self-sanitizing structure 100C, which is a cross-sectional view of the self-sanitizing structure 100 taken along line X-X of FIG. 1. In accordance with aspects of the invention, the self-sanitizing structure 100C includes all of the features and functionality of the self-sanitizing structure 100B (shown in FIG. 2B) and adds details of how certain features and functionality of the self-sanitizing structure 100B can be implemented. More specifically, the self-sanitizing structure 100C includes an integrated self-sanitizing system 130C that is substantially the same as the integrated self-sanitizing system 130B (shown in FIG. 2B) except the upper body 108 is configured to include or be entirely formed as one or more multi-layered structures or sheets 206. In accordance with aspects of the invention, the flexible multi-layered structures 206 include flexible fibrous element layers 206B formed between a substrate 206C and a top layer 206A. In accordance with aspects of the invention, the scattering elements 106B (shown in FIG. 2B) can be implemented as the flexible fibrous element layer(s) 206B. In accordance with embodiments of the invention, the top layer 206A and the substrate 206C can each be a substantially flexible material or a substantially rigid material. In embodiments of the invention a matrix material can be provided in one, some or all of the layers 206A, 206B, 206C.

In embodiments of the invention, the top layer 206A and the substrate 206C are configured to perform multiple functions. One set of functions relates to the self-sanitizing feature of the self-sanitizing structure 100C and include stabilizing and protecting the flexible fibrous element layer(s) 206B, as well as allowing light from the light sources 112, 112A to pass through both the substrate 206C and the top layers 206A. Another set of functions includes assisting with the non-self-sanitizing functionality of the self-sanitizing structure 100C. As previously, described herein, the self-sanitizing structures 100, 100A, 100B, 100C can be configured to perform a variety of non-self-sanitizing functions, including being used as a substantially flexible covering for an underlying rigid or flexible structure. For example, in some embodiments of the invention, the upper body 108 can be configured and arranged to function as a substantially flexible wall covering over a substantially rigid wall. Where the self-sanitizing structure 100C is used as a substantially flexible covering for an underlying rigid or flexible structure, the light sources 112, 112A and local processor 120 of the integrated self-sanitizing system 130C can be formed from flexible materials as well and secured against the low-contact, non-contact surface 104.

Figure 2D:
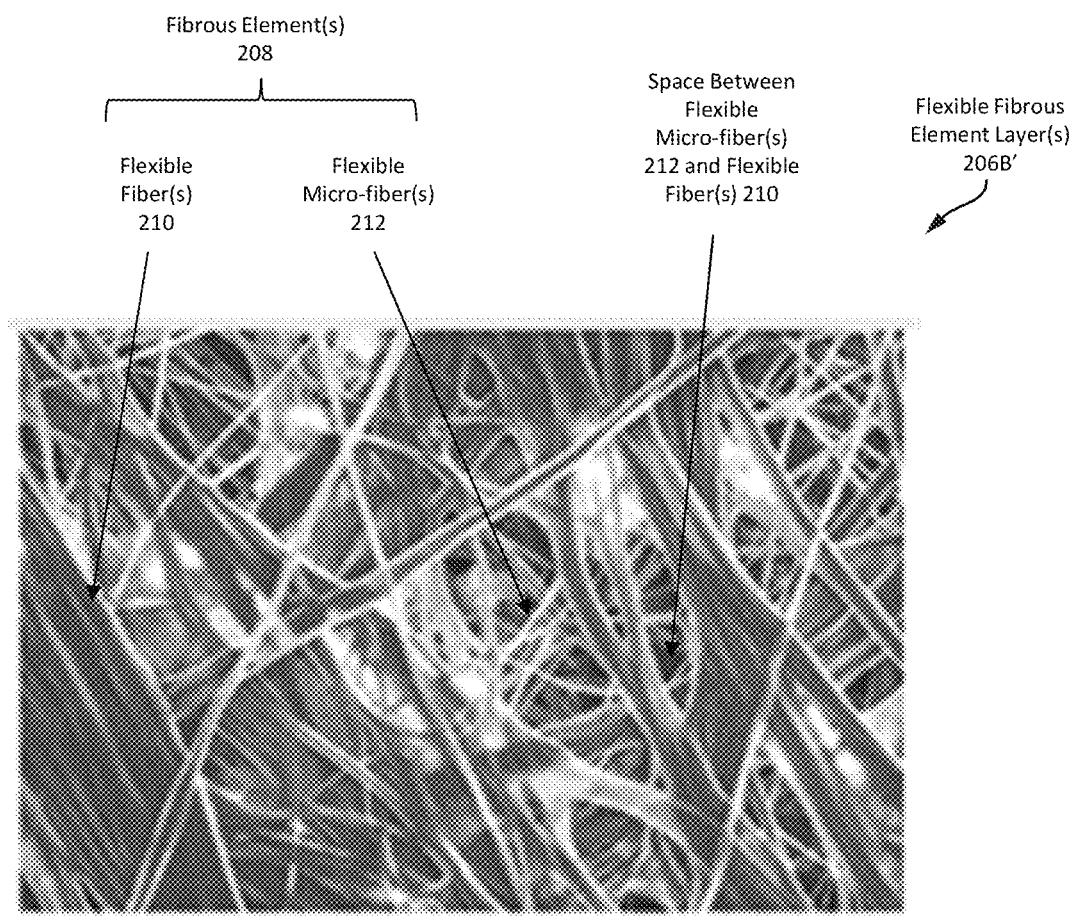
FIG. 2D depicts a scanning microscope image showing fibrous elements that include fibers and micro-fibers capable of being utilized in a self-sanitizing structure in accordance with embodiments of the invention.

FIG. 2D depicts a scanning microscope image of a flexible fibrous element layer 206B', which is an example of how the flexible fibrous element layer(s) 206B (shown in FIG. 2C) can be implemented. The flexible fibrous element layer 206B' is configured to include fibrous elements 208, which can include flexible fibers 210, flexible micro-fibers 212, or a combination of flexible fibers 210 and flexible micro-fibers 212 in accordance with embodiments of the invention. The flexible micro-fibers 212 can be synthetic fibers that are each smaller than naturally occurring fibers such as cotton, wool, and/or silk. In embodiments of the invention, the flexible micro-fibers 212 can have a diameter less than about 10 micrometers, and the flexible fibers 210 can have a diameter greater than about 10 micrometers. In embodiments of the invention, providing both the flexible fibers 210 and the flexible micro-fibers 212 scatter the light 116 (shown in FIGS. 3 and 4) and strikes a balance between scattering the light 116 and providing enough space for the scattered light 116 to pass through the flexible layer(s) 206B'. In some embodiments of the invention, only the flexible fibers 210 can be provided. In some embodiments of the invention, only the flexible micro-fibers 212 can be provided. In some embodiments of the invention, a combination of the flexible fibers 210 and the flexible micro-fibers 212 can be provided. A suitable material that can be configured to include the features and functionality of the flexible fibrous element layer 206B' described herein is a commercially available flexible material sold under the tradename Tyvek®.

Figure 3:
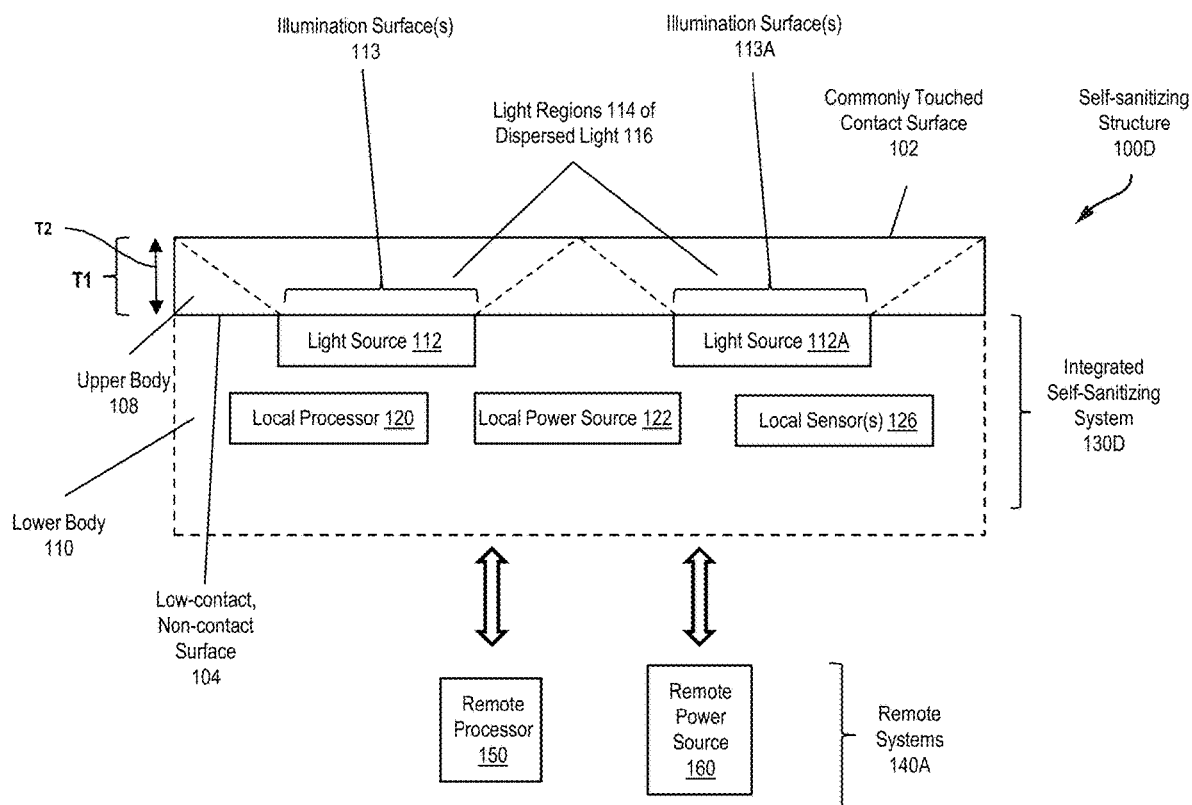
FIG. 3 depicts another example cross-sectional view of the self-sanitizing structure shown in FIG. 1, which is taken along line X-X and depicts additional details of the structure in accordance with embodiments of the invention.

FIG. 3 depicts a self-sanitizing structure 100D, which is a cross-sectional view of the structure 100 taken along line X-X of FIG. 1. In accordance with aspects of the invention, the self-sanitizing structure 100D includes all of the features and functionality of the self-sanitizing structures 100, 100A, 100B 100C (shown in FIGS. 2A-2D) and adds details of how certain features and functionality of the self-sanitizing structures 100, 100A, 100B, 100C can be implemented. More specifically, the self-sanitizing structure 100D includes an integrated self-sanitizing system 130D that is substantially the same as the integrated self-sanitizing system 130C (shown in FIG. 2C) except the lower body 110 is configured to include a local power source 122 and local sensors 126. The self-sanitizing structure 100D also includes additional details about the light sources 112, 112A; the light 116 generated by the light sources 112, 112A; and how the remote systems 140 (shown in FIG. 2C) can be implemented as remote systems 140A having a remote processor 150 and/or a remote power source 160.

In embodiments of the invention, the functionality provided by the local processor 120 and the local power source 122 can be provided by the remote systems 140A having the remote processor 150 and the remote power source 160, which are configured and arranged to be external to the self-sanitizing structure 100D. In embodiments of the invention, the remote processor 150 and the remote power source 160 are in wired or wireless communication with the light sources 112, 112A. In some embodiments of the invention, the remote systems 140A can include a cloud computing system in wired or wireless electronic communication with one or all of the components of the self-sanitizing structure 100D. The cloud computing system can supplement, support or replace some or all of the electronic and/or processor functionality of the self-sanitizing structure 100D. Additionally, some or all of the functionality of the components of the self-sanitizing structure 100D can be implemented as a node of the cloud computing system.

In embodiments of the invention where the light sources 112, 112A are configured to generate blue and/or or purple light, the light sources can be red/green/blue (RGB), red/green/blue/white (RGBW), or white LEDs, which enables multiple wavelengths or colors to be programmed. The wavelengths of light generated by the LEDs can, in some embodiments of the invention, be converted to shorter wavelength blue or purple light via suitable fluorescent pigments added to the body region 106 (shown in FIG. 1) of the self-sanitizing structure 100D.

In embodiments of the invention, the local power source 122 is configured and arranged to provide power to any electrical component of the integrated self-sanitizing system 130D. In embodiments of the invention, the electrical components of the integrated self-sanitizing systems 130D include but are not limited to the light sources 112, 112A, the local processor 120, and/or the local sensors 126. The local power source 122 can be any known type of local power source, including but not limited to rechargeable batteries and/or energy harvesting circuitry configured to derive or transduce energy from external sources (e.g., solar power, thermal energy, wind energy, salinity gradients, wireless power, and/or kinetic energy, which is also known as ambient energy).

In some embodiments of the invention, both the local power source 122 and the remote power source 160 are provided, and the power requirements of the integrated self-sanitizing system 130D are shared between the local power source 122 and the remote power source 160. In some embodiments of the invention, the power requirements of the integrated self-sanitizing system 130D are shared between the local power source 122 and the remote power source 160 such that the power requirements provided by the local power source 122 are minimized. In some embodiments of the invention, the local power source 122 can be recharged by the remote power source 160 and/or by on-board power elements of the remote processor 150.

In embodiments of the invention, the local processor 120 is configured and arranged to provide the various control operations applied to the light sources 112, 112A, the local sensors 126, and/or the local power source 122. In embodiments of the invention, the local processor 120 can be implemented as a computer system 1900 (shown in FIG. 19). In some embodiments of the invention, the local processor 120 can be implemented as one or more miniaturized computers having sufficiently small size that they can be integrated into a wide variety of implementations of the self-sanitizing structure 100D.

In some embodiments of the invention, both the local processor 120 and the remote processor 150 are provided, and computer processing functionality of the integrated self-sanitizing system 130D is shared between the local processor 120 and the remote processor 150. In some embodiments of the invention, computer processing functionality of the integrated self-sanitizing system 130D is allocated between the local processor 120 and the remote processor 150 such that relatively low power (e.g., below a power threshold) computer processing functionality is provided by the local processor 120 (sometimes referred to as edge computing), and relatively high power (e.g., above the power threshold) computer functionality is provided by the remote processor 150 (sometimes referred to as cloud computing), thereby minimizing the energy/power draw of the local processor 120. The local processor 120 and the remote processor 150 can also work independently or in tandem to implement the features and functionality of a processor 1510 (shown in FIGS. 15A, 15B and 15D) and a processor 1710 (shown in FIGS. 17A-17D). Details of the features and functionality of the processors 1510, 1710 are described subsequently herein in connection the descriptions of the aspects of the invention depicted in FIGS. 15A, 15B, 15D, and 17A-17D. In embodiments of the invention, each of the processors 120, 150, 1510, 1710 described herein can be configured to include the features and functionality of the computer system 1900 (shown in FIG. 19).

Figure 6A:
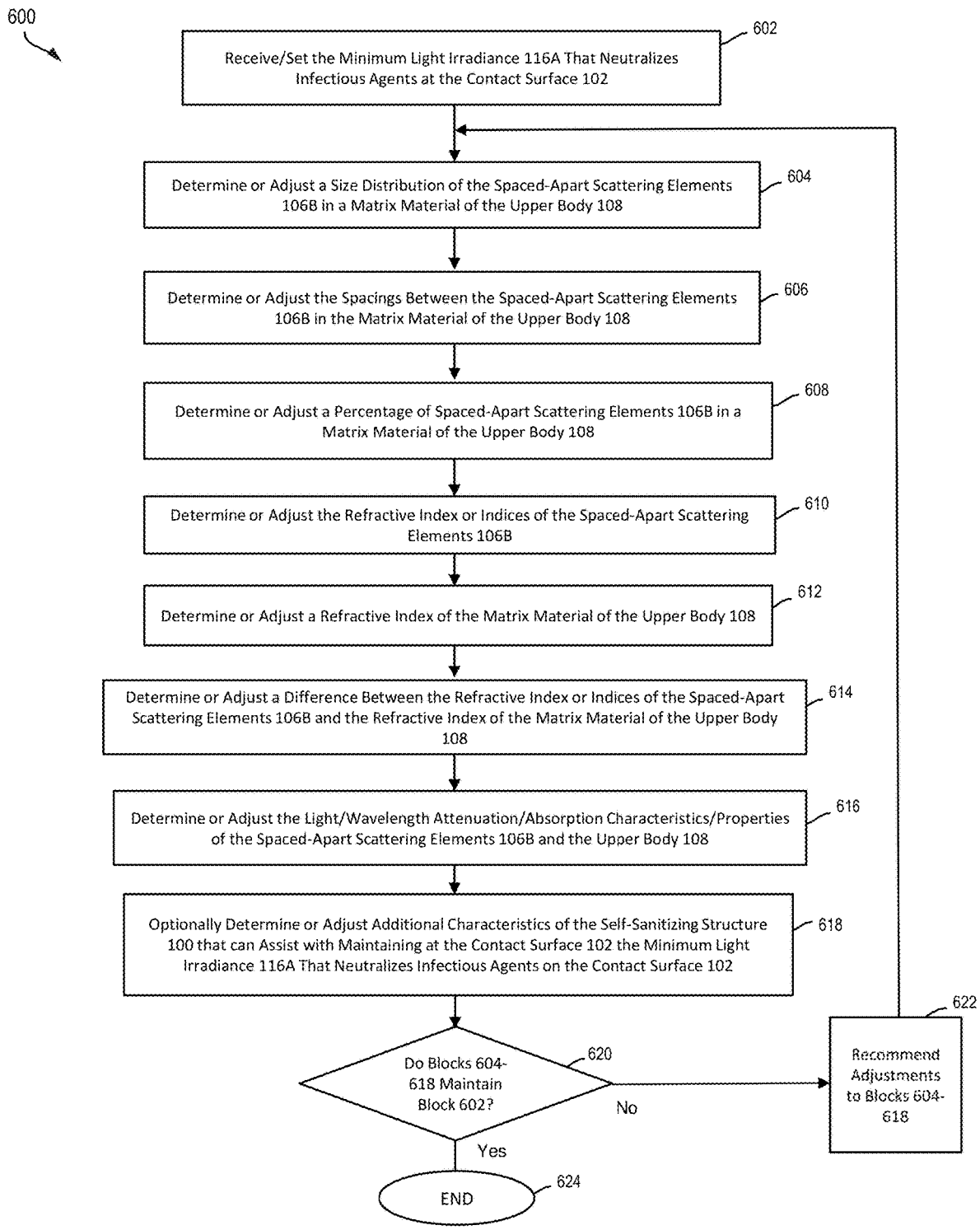
FIG. 6A depicts a flow diagram illustrating a methodology in accordance with embodiments of the invention.
Figure 6B:
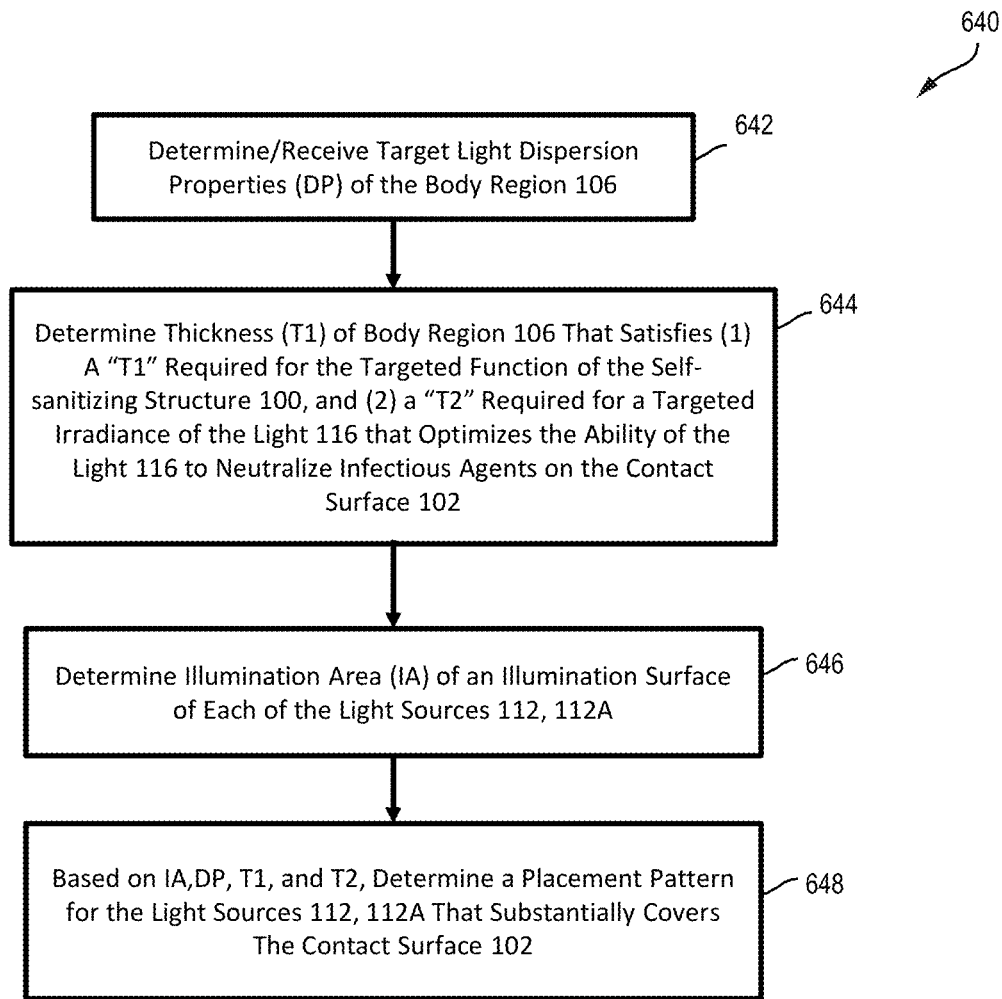
FIG. 6B depicts a flow diagram illustrating a methodology in accordance with embodiments of the invention.

In some embodiments of the invention, the remote processor 150 can also be utilized to implement computer-based processes for designing or otherwise developing the features and functionality of the self-sanitizing system 130D of the integrated self-sanitizing system 130D, including but not limited to the computer-implemented methods 600, 640 shown in FIGS. 6A and 6B. The details of the computer-implemented methods 600, 640 are provided subsequently herein in connection with the descriptions of FIGS. 6A and 6B.

Figure 13:
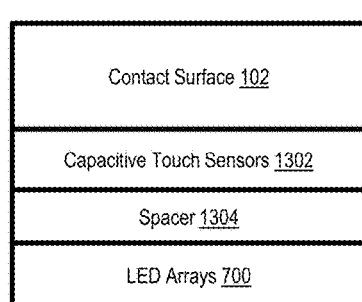
FIG. 13 depicts a block diagram illustrating how the local sensors shown in FIG. 12 can be implemented as capacitive touch sensors in accordance with embodiments of the invention.
Figure 14:
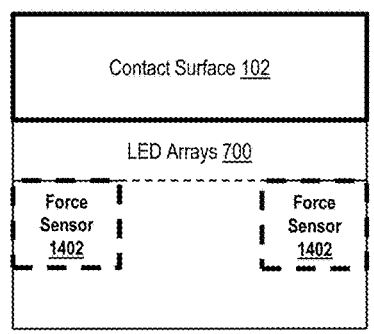
FIG. 14 depicts a block diagram illustrating how the local sensors shown in FIGS. 5 and 6 can be implemented as force sensors in accordance with embodiments of the invention.

In embodiments of the invention, the local sensors 126 can be implemented as any component that can detect contact between a person and the contact surface 102. In some aspects of the invention, the local sensors 126 can be implemented as force sensors. In some aspects of the invention, the force sensors can be implemented as individually addressable force sensors configured to capture both a touch event and a location of the touch event on the contact surface 102. In some aspects of the invention, the local sensors 126 can be implemented as substantially translucent capacitive-touch sensors configured and arranged to detect and record capacitance changes that result from a person touching the contact surface 102. In some embodiments of the invention, the local sensors can be implemented as capacitive-touch sensors printed on a substrate (e.g., metal foil) using a conductive ink. In some aspects of the invention, the capacitive-touch sensors can be implemented as individually addressable capacitive-touch sensors configured to capture both a touch event and a location of the touch event on the contact surface 102. Additional details of how the local sensors 126 can be implemented as capacitive sensors 1302 and/or force sensors 1402 are depicted in FIGS. 13 and 14 and described in greater detail subsequently herein.

In embodiments of the invention, the local sensors 126 are in wired or wireless communication with one or both of the processors 120, 150 to provide sensor feedback for use in various computer processor functions performed by the processors 120, 150. In some embodiments of the invention, the local sensors 126 are configured and arranged to detect an instance of a person touching the contact surface 102, and to capture touch data 1770 (shown in FIG. 17B) that identifies details related to the instance of a person touching the contact surface 102. In embodiments of the invention, an instance of a person touching the contact surface 102 can be defined as uninterrupted contact between a person and the contact surface 102. For example, a person resting their right forearm on the contact surface 102, removing their right forearm from the contact surface 102, and placing their left forearm on the contact surface 102 would be detected as two (2) separate touching instances or touch readings. In embodiments of the invention, the touch data 1770 includes touch readings 1774 (shown in FIG. 17B) and associated timestamp data 1772 (shown in FIG. 17B) that are transmitted to the processor 1710 (shown in FIG. 17B) where they are further analyzed to generate touch-related time data 1734 (shown in FIG. 17B) and touch-related location data 1736 (shown in FIG. 17B) that are stored as touch data records 1730 (shown in FIG. 17B). Additional details of how the local sensors 126 works with the processor 1710 to control features and functions of any of the self-sanitizing systems described herein are illustrated in FIGS. 17A-17E and described subsequently herein.

As shown in FIG. 3, in embodiments of the invention, the sanitization characteristics/properties 106A (shown in FIG. 2A) of the upper body 108 disperse/scatter the light 116 that passes through the upper body 108, thereby generating the light regions 114. In some aspects of the invention, the dispersion/scattering pattern (i.e., the shape, contour, and area of the light regions 114) generated by the sanitization characteristics/properties 106A can be controlled/tuned by controlling/tuning parameters of the scattering elements 106B (shown in FIG. 2B) of the sanitization characteristics/ properties 106A. In embodiments of the invention, the parameters of the scattering elements 106B include spacing between the scattering elements 106B and a size of each of the scattering elements 106B. In embodiments of the invention, the size of each of the scattering elements 106B is sufficient to scatter the light 116; and the spacing between the scattering elements 106B is sufficient to enable the scattered light 116 to pass through the upper body 108 to the contact surface 102.

The shape, contour, and area of the light regions 114 can be further controlled and tuned by controlling the placement and configuration of the light sources 112, 112A. In some aspects of the invention, the light sources 112, 112A are each multiple discrete light sources configured and arranged according to an array pattern that, in accordance with aspects of the invention, positions the discrete light sources with respect to one another such that the light regions 114 pass light 116 through desired regions of the contact surface 102, thereby targeting the neutralization of infection agents to selected regions of the contact surface 102. The array pattern can be set based on a variety of factors including the thickness (T1) of the upper body 108; the sanitization characteristics 106A (shown in FIG. 2A) of the upper body 108; the contour and area of the illumination surfaces 113, 113A; the anticipated power levels at which the light sources 112, 112A will be operated; and the distance from the illuminations surfaces 113, 113A to the contact surface 102. In the self-sanitizing structure 100D shown in FIG. 3, the distance (T2) from the illumination surfaces 113, 113A to the contact surface 102 is substantially the same as the thickness (T1) of the upper body 108. In some embodiments of the invention, the light sources 112, 112A can be implemented as miniaturized LED elements printed on a thin substrate (e.g., polyethylene terephthalate (PET), polyimide (PI), or paper). In embodiments of the invention where the self-sanitizing structure 100B is implemented as a multi-layered flexible sheet, the above-described printed LEDs can be directly laminated on the flexible sheet using a roll-to-roll (R2R) process. In embodiments of the invention where the self-sanitizing structure 100B is implemented as a multi-layered flexible sheet, the above-described printed LEDs can be directly laminated between adjacent layers of the multiple layers that form the flexible sheet using a roll-to-roll (R2R) process. Wired or other connectors can be positioned at edges of the self-sanitizing structure 100B for providing power remotely in a controlled way.

In embodiments of the invention, the self-sanitizing system 130D includes features and functionality that enable the self-sanitizing system 130D to set and/or tune the dispersion (or scattering) characteristics/properties, the wavelength, and the irradiance of the light 116 that passes through the upper body region 106 to reach the contact surface 102. In embodiments of the invention, dynamic techniques and static techniques are used to set and/or tune the dispersion/scattering characteristics/properties, the wavelength, and the irradiance of the light 116 that passes through the upper body region 106 to reach the contact surface 102. In embodiments of the invention, irradiance and wavelength of the light 116 can be dynamically set and/or tuned by dynamically controlling the light sources 112, 112A using the processors 120, 150. In embodiments of the invention dispersion/scattering characteristics/properties of the light 116 can be set and/or tuned by statically controlling sanitization characteristics/properties 106A (shown in FIG. 2A) of the self-sanitization structure 100D.

Figure 4:
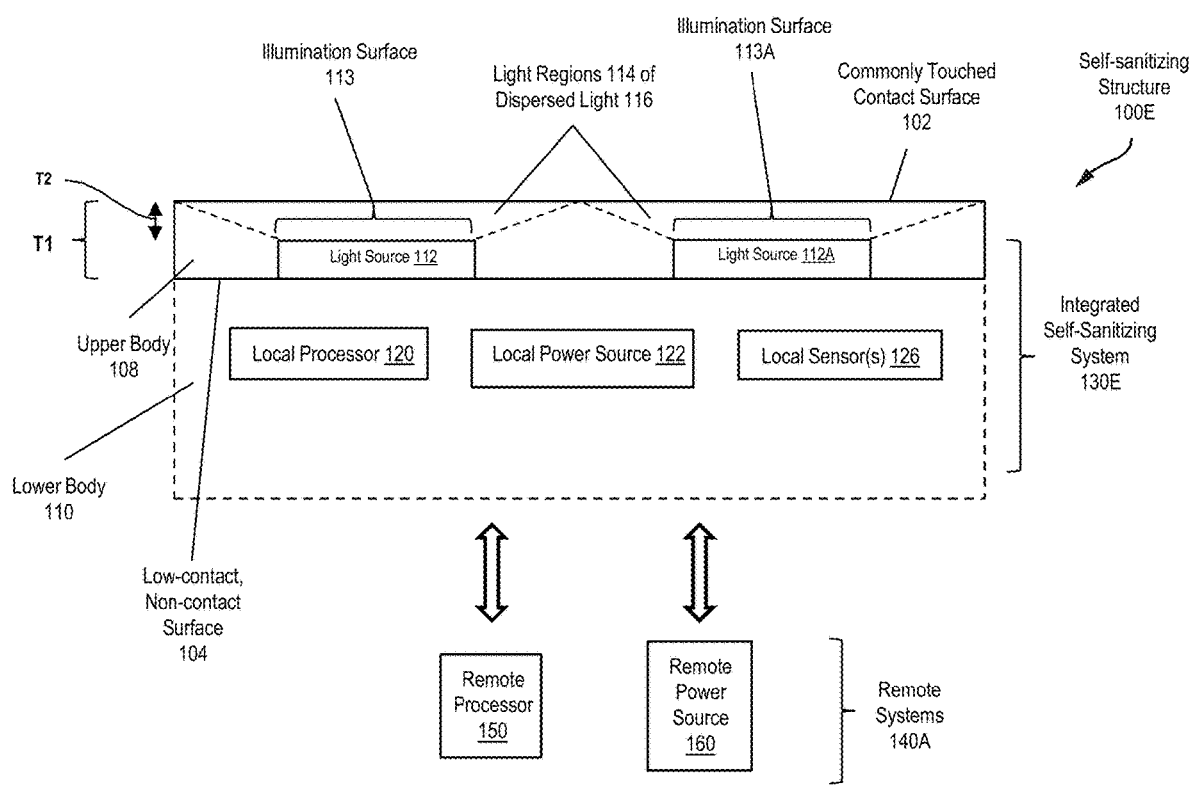
FIG. 4 depicts another example cross-sectional view of the self-sanitizing structure shown in FIG. 1, which is taken along line X-X and depicts additional details of the structure in accordance with embodiments of the invention.

FIG. 4 depicts a self-sanitizing structure 100E, which is a cross-sectional view of the structure 100 taken along line X-X of FIG. 1. In accordance with aspects of the invention, the self-sanitizing structure 100E includes all of the features and functionality of the self-sanitizing structures 100, 100A, 100B 100C, 100D (shown in FIGS. 2A-2D and 3) and adds details of how certain features and functionality of the self-sanitizing structures 100, 100A, 100B, 100C, 100D can be implemented. More specifically, the self-sanitizing structure 100E includes an integrated self-sanitizing system 130E that is substantially the same as the integrated self-sanitizing system 130D (shown in FIG. 3) except that the integrated self-sanitizing system 130E positions its light sources 112, 112A within the upper body 108, and with the further exception that the thickness (T1) of the upper body 108 is not the same as the distance (T2) from the illumination surfaces 113, 113A to the contact surface 102. Otherwise, all of the functionality described in connection with the integrated self-sanitizing structure 100D applies as well to the integrated self-sanitizing structure 100E.

Figure 5A:
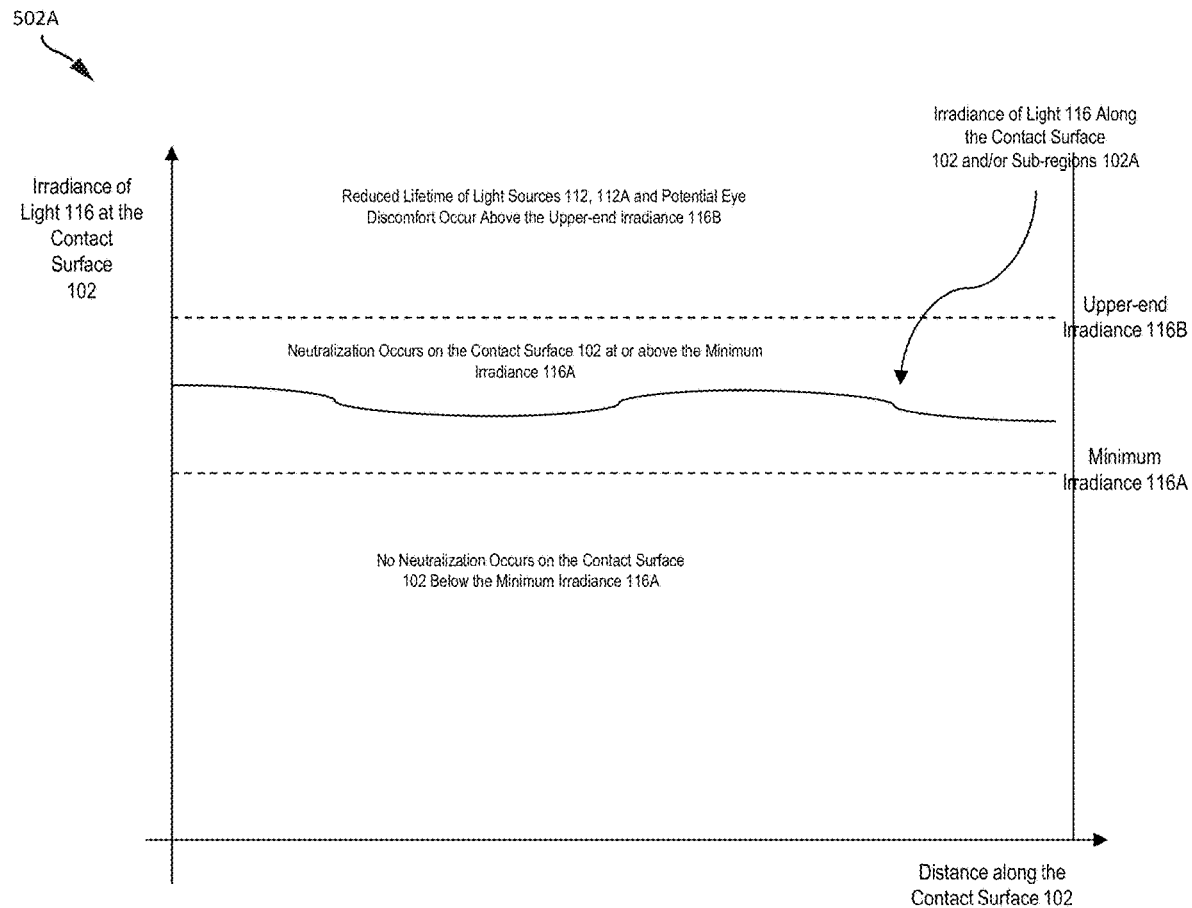
FIG. 5A depicts a plot of the light irradiance maintained along a contact surface and/or a high-touch sub-region of a self-sanitizing structure in accordance with embodiments of the invention.

FIG. 5A depicts a plot 502A of the light irradiance that can be maintained at the contact surface 102 versus a horizontal distance along the contact surface 102 in accordance with aspects of the invention. More specifically, the curve shown in the plot 502A is an example of the irradiance level of light 116 (shown in FIGS. 3 and 4) that can be generated and maintained at the contact surface 102 using the features and functionality of any one of the self-sanitizing structures 100, 100A, 100B, 100C, 100D, 100E (shown in FIGS. 1, 2A-2D, 3 and 4) in accordance with embodiments of the invention. In the descriptions of the plots 502A, 502B, 502C shown in FIGS. 5A-5C, reference will be made to the self-sanitizing structure 100 for ease of description. However, the descriptions of the plots 502A, 502B, 502C shown in FIGS. 5A-5C apply to any one of the self-sanitizing structures 100, 100A, 100B, 100C, 100D, 100E. In the example, shown in FIG. 5A, the sanitization characteristics/properties 106B of the self-sanitizing structure 100 have been controlled to maintain the irradiance of the light 116 (shown in FIGS. 3 and 4) at and along the contact surface 102 between a minimum light irradiance 116A and an upper-end light irradiance 116B. When the light 116 is between the minimum light irradiance 116A and the upper-end light irradiance 116B, the light 116 neutralizes infectious agents on the contact surface 102. When the light 116 is above the minimum light irradiance 116A and above the upper-end light irradiance 116B, the light 116 neutralizes infectious agents on the contact surface 102 but, because of increased power applied to the light sources 112, 112A, has the potential to reduce the lifetime of the light sources 112, 112A and increase the temperature of the body region 106. Additionally, when the light 116 is above the minimum light irradiance 116A and above the upper-end light irradiance 116B, the light 116 can cause eye discomfort after a sufficient duration of exposure to the light 116. If the light 116 falls below the minimum light irradiance 116A, the light 116 has insufficient irradiance to neutralize infectious agents on the contact surface 102.

Figure 5B:
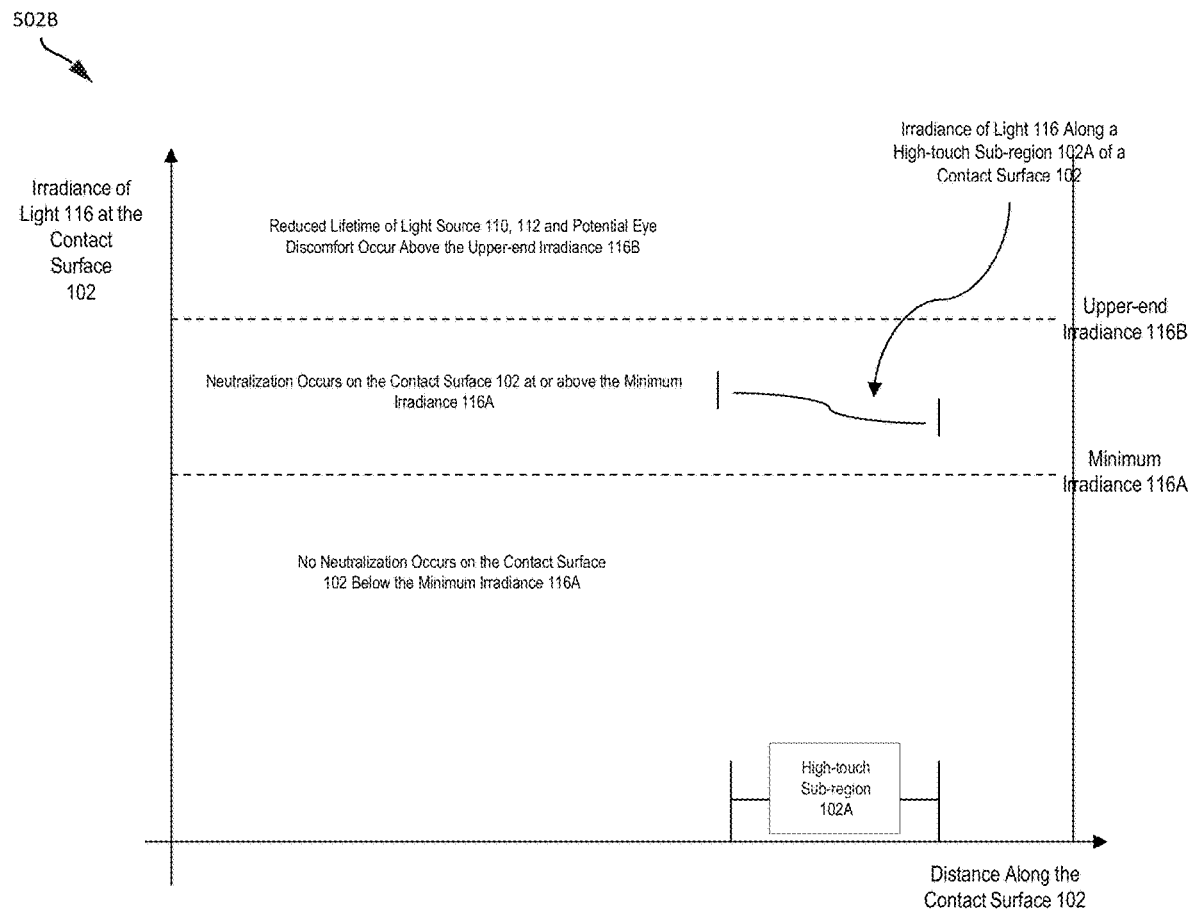
FIG. 5B depicts a plot of the light irradiance maintained along a high-touch sub-region of a self-sanitizing structure in accordance with embodiments of the invention.

FIG. 5B depicts a plot 502B that is substantially the same as the plot 502A (shown in FIG. 5A). However, the curve in the plot 502B shows the behavior of the light 116 that is targeted, in accordance with aspects of the invention, to the high-touch sub-regions 102A of the contact surface 102.

Figure 5C:
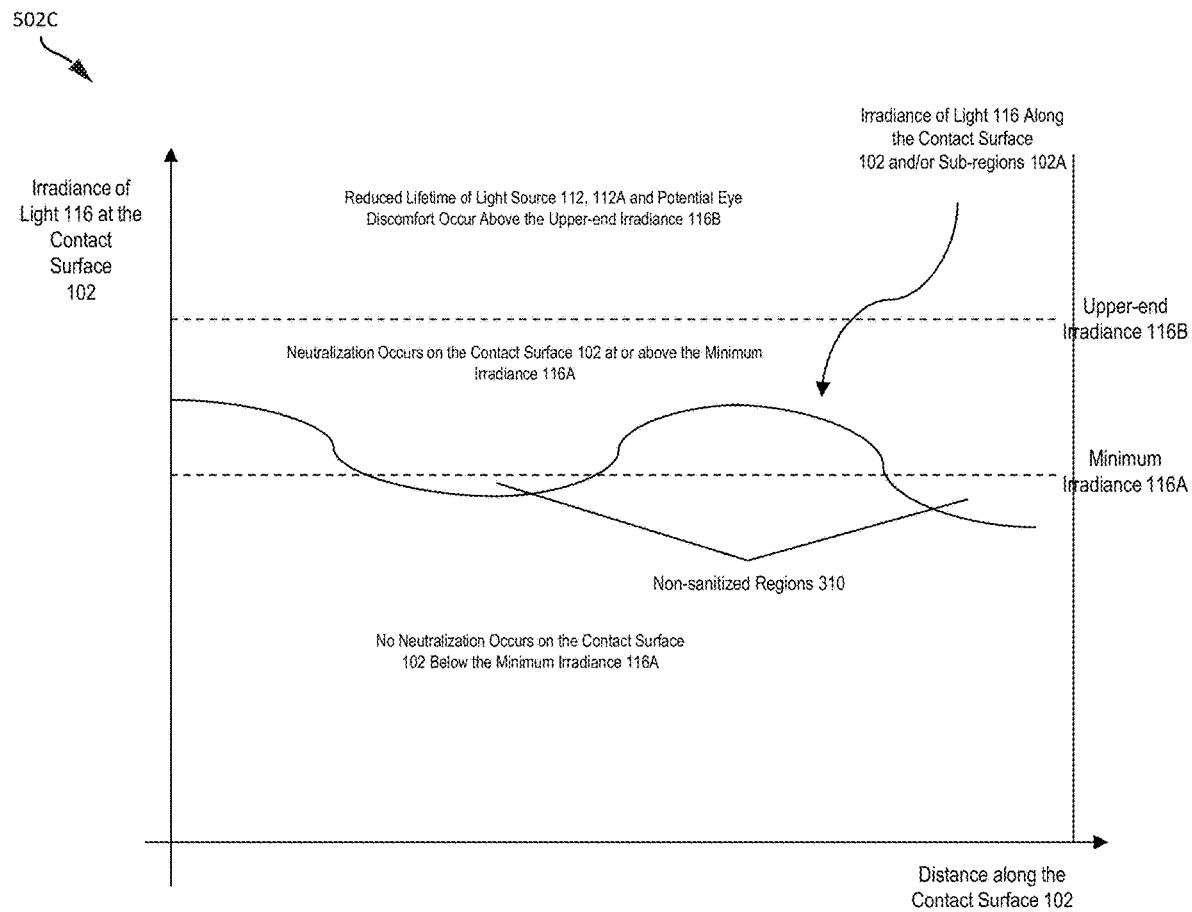
FIG. 5C depicts a plot of the light irradiance along a structure's surface in an example where sanitization characteristics (or properties) of the structure have not been controlled in accordance with embodiments of the invention.

FIG. 5C depicts a plot 502C that is substantially the same as the plot 502A shown in FIG. 5A, however the curve in the plot 502C shows the behavior of the light 116 that is not being controlled to maintain the light 116 along the contact surface 102 above the minimum light irradiance 116A. In the plot 502C, the light 116 at the contact surface 102 fluctuates above and below the minimum light irradiance 116A at different points along the contact surface 102. Accordingly, some regions of the contact surface 102 have non-sanitized regions 310. In the non-sanitized regions 310, the irradiance level of the light 116 is below the minimum light irradiance 116A, so the light 116 has insufficient irradiance to neutralize infectious agents on the contact surface 102. Accordingly, the non-sanitized regions 310 of the contact surface 102 are not sanitized and could act as a site for further microbial contamination.

FIG. 6A depicts a flow diagram illustrating a computer-implemented method 600 of determining parameters of any one of the self-sanitizing structures 100, 100A, 100B, 100C, 100D, 100E (shown in FIGS. 1, 2A-2C, 3 and 4) in accordance with embodiments of the invention. In embodiments of the invention, the method 600 can be performed by a computer system (e.g., the remote processor 150 having the functionality of the computer system 1900 shown in FIG. 19) programmed to execute the various functional features depicted in the method 600. In embodiments of the invention, the operations of the method 600 can be executed using known computer analysis techniques that do not require specialized computer functionality. In embodiments of the invention, the method 600 can be implemented to include any combination of the operations depicted at blocks 604-618.

The computer-implemented method 600 begins at block 602 by setting and/or receiving a minimum light irradiance 116A to be maintained at the contact surface 102 such that the light 116 neutralizes infectious agents at the contact surface 102. At block 604, the method 600 determines or adjusts a size distribution of the spaced-apart scattering elements 106B in the matrix material of the upper body 108. At block 606, the method 600 determines or adjusts the spacings between the spaced-apart scattering elements 106B in the matrix material of the upper body 108. At block 608, the method 600 determines or adjusts a percentage of the spaced-apart scattering elements 106B that are in the matrix material of the upper body 108. At block 610, the method 600 determines or adjusts the refractive index or indices of the spaced-apart scattering elements 106B in the matrix material of the upper body 108. At block 612, the method 600 determines or adjusts a refractive index of the matrix material of the upper body 108. At block 614, the method 600 determines or adjusts a difference between the reference index or indices of the spaced-apart scattering elements 106B and the refractive index of the matrix material of the upper body 108. At block 616, the method 600 determines or adjusts the light and/or wavelength attenuation and/or absorption characteristics/properties 106E of the spaced-apart scattering elements 106B and the matrix material of the upper body 108. In accordance with aspects of the invention, the light and/or wavelength absorption characteristics 106E of the entire upper body 108 (including the scattering elements 106B and the matrix material) are evaluated to ensure that the light/wavelength absorption of the upper body 108 is sufficiently low to not require that higher power levels are applied to the light sources 112, 112A to offset the absorption. At block 618, the method 600 optionally determines or adjusts additional sanitization characteristics/properties 106A of the self-sanitizing structure 100, including, one or more of the lens elements 106C; contact surface topography and/or internal topography 106D; diffuser elements 106F; and a PMMA percentage 106G. FIG. 2E depicts tables A and B illustrating examples of the sanitization characteristics/properties 106A and the light coverage or light footprint characteristics/properties 107A of the self-sanitizing structures 100, 100A 100B, 100C, 100D, 100E that can be utilized in block 618 the method 600 in accordance with embodiments of the invention.

Continuing with FIG. 6A, at decision block 620, the method 600 determines whether or not the determinations and/or adjustments at blocks 604-618 maintain and/or achieve block 602 (i.e., the minimum light irradiance 116A at the contact surface 102 that neutralizes infectious agents). In embodiments of the invention, the determinations at decision block 620 can be implemented by using the remote processor 150 (shown in FIGS. 3 and 4) and a trained machine learning algorithm to generate a model of any of the self-sanitizing structures 100, 100A 100B, 100C, 100D, 100E wherein the model is configured to reflect the determinations and/or adjustments set at blocks 602-618. The remote processor 150 can apply the model to a simulation algorithm to determine whether or not the determinations and/or adjustments at blocks 604-618 maintain and/or achieve block 602 (i.e., the minimum light irradiance 116A (shown in FIGS. 5A-5C) at the contact surface 102 that neutralizes infectious agents). If the result of the inquiry at decision block 620 is yes, the method 600 proceeds to block 624 and ends. If the result of the inquiry at decision block 620 is no, the method 600 proceeds to block 622; analyzes the determinations made at decision block 620; makes recommendations for adjustments to the determinations made at blocks 604-618 in a last (or in prior) iterations of the method 600; and returns to block 604 for a next iteration of the method 600.

FIG. 6B depicts a flow diagram illustrating a computer-implemented method 640 of determining a placement pattern for the light sources 112, 112A (shown in FIGS. 3 and 4) in accordance with embodiments of the invention. In embodiments of the invention, the placement pattern determined using the method 640 is one of the light coverage or light footprint characteristics/properties 107A (shown in FIG. 2A). In embodiments of the invention, the method 640 can be performed by a computer system (e.g., the remote processor 150 having the functionality of the computer system 1900 shown in FIG. 19) programmed to execute the various functional features depicted in the method 640. In embodiments of the invention, the operations of the method 640 can be executed using known computer analysis techniques that do not require specialized computer functionality.

FIG. 6B depicts a flow diagram illustrating a methodology 640 in accordance with embodiments of the invention. In embodiments of the invention, image analysis techniques can be utilized to make the determinations defined at blocks 642-648. The method 640 begins at block 642 by determining and/or receiving target light dispersion properties (DP) of the body region 106. At block 644, the method 640 determines a thickness (T1) of the body region that satisfies a T1 that is required by the non-self-sanitizing functions of the self-sanitizing structure 100; and that satisfies a thickness T2 that is required for a targeted irradiance of the light 116 that optimizes the ability of the light 116 to remove infectious agents from the contact surface 102. At block 646, the method 640 determines an illuminations area (IA) of the illumination surfaces 113, 113A of the light sources 112, 112A. At block 648, the method 640 determines, based on IA, DP, T1, and T2, a placement pattern for the light sources 112, 112A that generates light regions 114 of light 116 that substantially covers the contact surface 102. In some embodiments of the invention, block 648 can be configured to determine, based on IA, DP, T1, and T2, a placement pattern for the light sources 112, 112A that generates light regions 114 of light 116 that substantially covers one or more predetermined portions of the contact surface 102.

Figure 7:
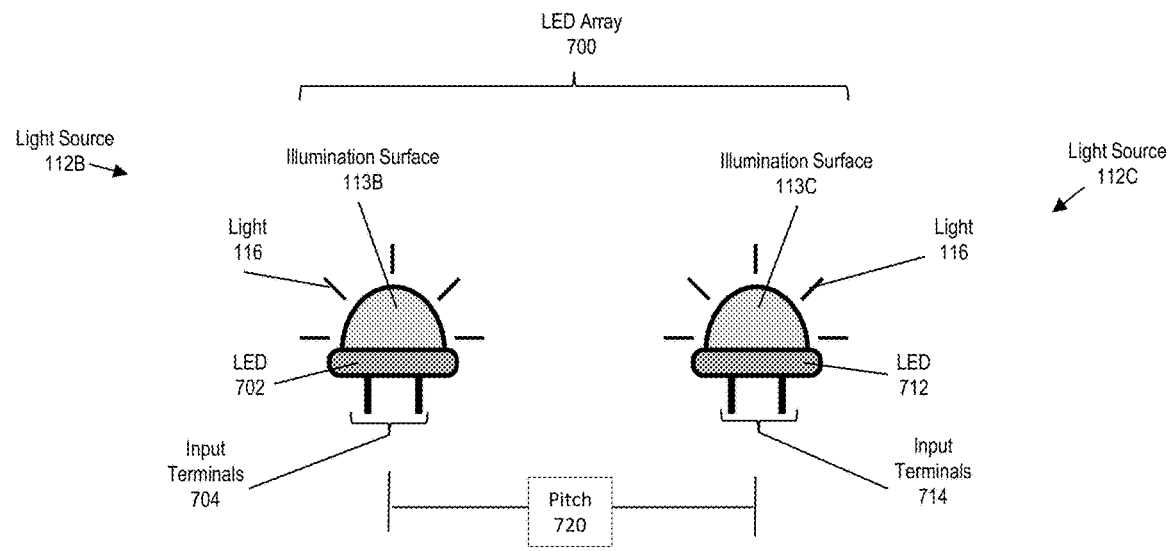
FIG. 7 depicts a block diagram illustrating how a light source of a self-sanitizing structure can be implemented as an LED array in accordance with embodiments of the invention.

FIG. 7 depicts a block diagram illustrating details of how the light sources 112, 112A (shown in FIGS. 3 and 4) can be implemented as an LED array 700 having an LED pitch 720 in accordance with embodiments of the invention. Although two (2) LED light sources 112B, 112C are shown, any number of LEDs can be included in the array 200. Each LED light source 112B, 112C includes an LED element 702, 712, input terminal 704, 714, and an illumination surface or optical lens 113B, 113C, configured and arranged as shown. In some embodiments of the invention, the transmission path of the light 116, prior to the scattering operations in accordance with aspects of the invention, can be influenced by the shape of the illumination surface (or optical lens) 113B, 113C. The array 700 can be packaged using any suitable array packaging technique, including providing various connectors for coupling external devices (e.g., the processors 120, 150, 1510, 1710 described herein) to the input terminals, along with encapsulation structures (substrates and the like) to protect the array 700.

Figure 8:
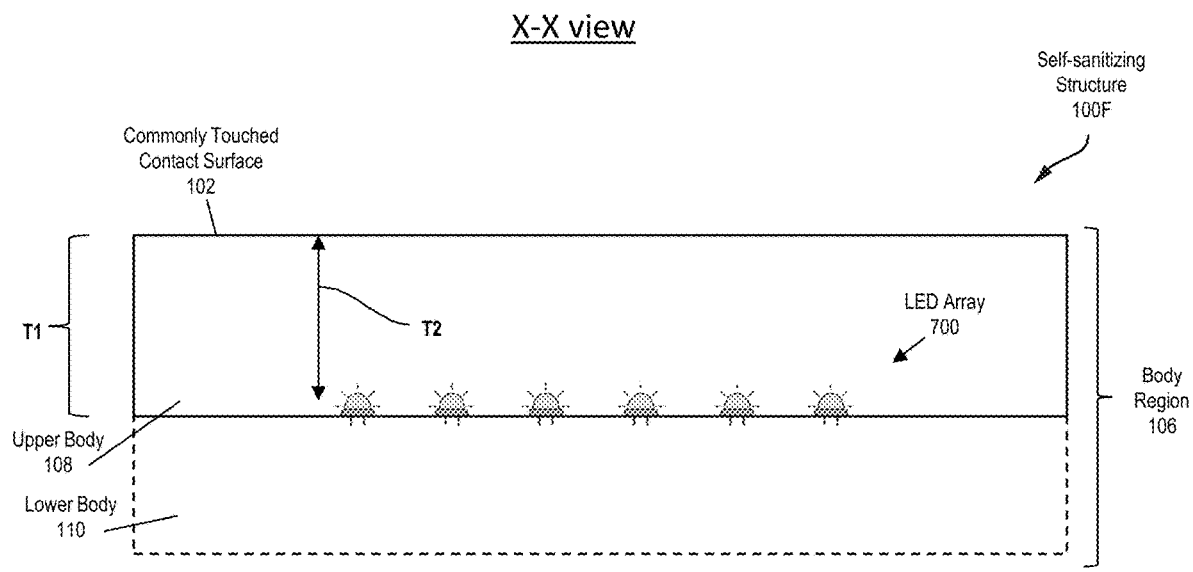
FIG. 8 depicts a cross-sectional view of the self-sanitizing structure shown in FIG. 1, which is taken along line X-X and depicts additional details of how a light source of the self-sanitizing structure can be implemented as an array of LEDs in accordance with embodiments of the invention.

FIG. 8 depicts a self-sanitizing structure 100F, which is a cross-sectional view of the self-sanitizing structure 100 taken along line X-X of FIG. 1. In accordance with aspects of the invention, the self-sanitizing structure 100F includes all of the features and functionality of the self-sanitizing structure 100E (shown in FIG. 4) and adds details of how the LED array 700 can be integrated within the body 106 of the self-sanitizing structure 100F in accordance with embodiments of the invention.

Figure 9:
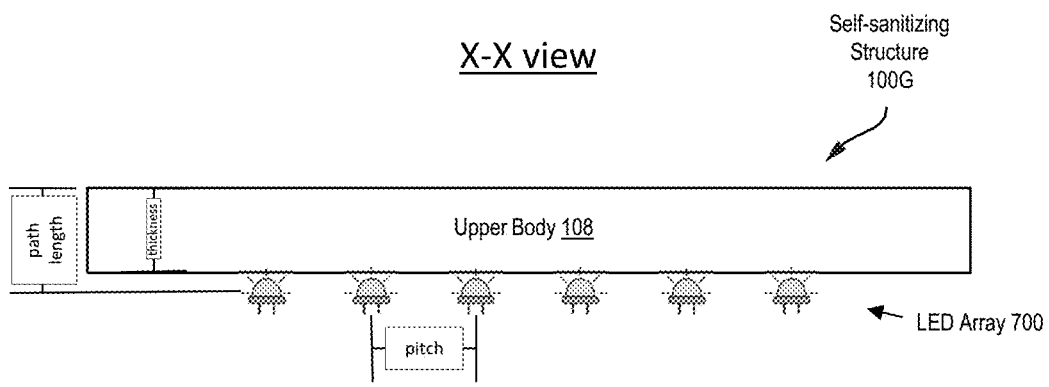
FIG. 9 depicts a cross-sectional view of a portion of the self-sanitizing structure shown in FIG. 1, which is taken along line X-X and depicts additional details of how a light source of the self-sanitizing structure can be implemented as an array of LEDs in accordance with embodiments of the invention.

FIG. 9 depicts a self-sanitizing structure 100G, which is a cross-sectional view of the self-sanitizing structure 100 taken along line X-X of FIG. 1. In accordance with aspects of the invention, the self-sanitizing structure 100G includes all of the features and functionality of the self-sanitizing structure 100F (shown in FIG. 8) and adds details of how the LED array 700 can be positioned under and secured to the upper body region 106 in accordance with embodiments of the invention.

Figure 10:
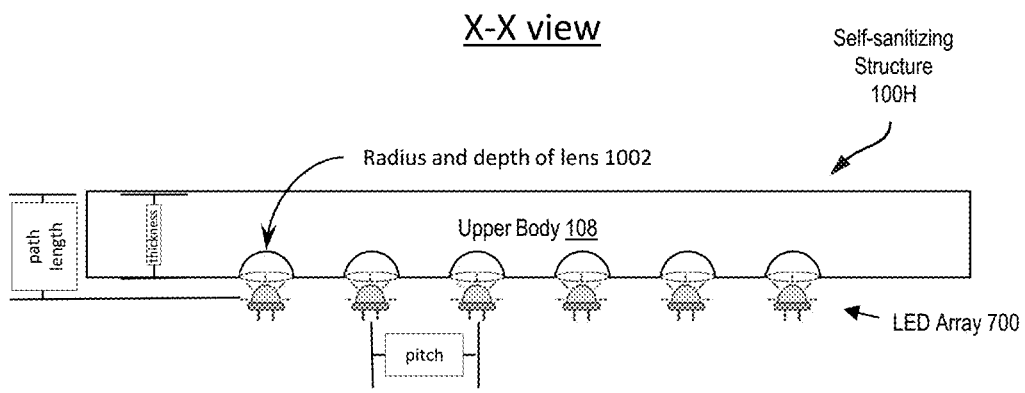
FIG. 10 depicts a cross-sectional view of a portion of the self-sanitizing structure shown in FIG. 1, which is taken along line X-X and depicts additional details of how a light source of the self-sanitizing structure can be implemented as an array of LEDs, along with additional details of how lensing elements of the self-sanitizing structure can be implemented.

FIG. 10 depicts a self-sanitizing structure 100H, which is a cross-sectional view of the self-sanitizing structure 100 taken along line X-X of FIG. 1. In accordance with aspects of the invention, the self-sanitizing structure 100H includes all of the features and functionality of the self-sanitizing structure 100G (shown in FIG. 9) and adds details of how lensing elements 1002 can be formed above the LED array 700 and integrated within a bottom surface of the upper body 108 in accordance with embodiments of the invention. In some embodiments of the invention, the radius and depth dimensions of the lensing elements 1002 are configured to selectively focus and/or disperse/scatter the light 116 that moves through the lensing elements 1002 and the upper body 108, thereby enabling further control and tuning of the shape, contour, and area of the light regions 114 in accordance with embodiments of the invention. In some embodiments of the invention, the lensing elements 1002 are more complex including but not limited to non-symmetric shapes and/or Fresnel configurations.

Figure 11:
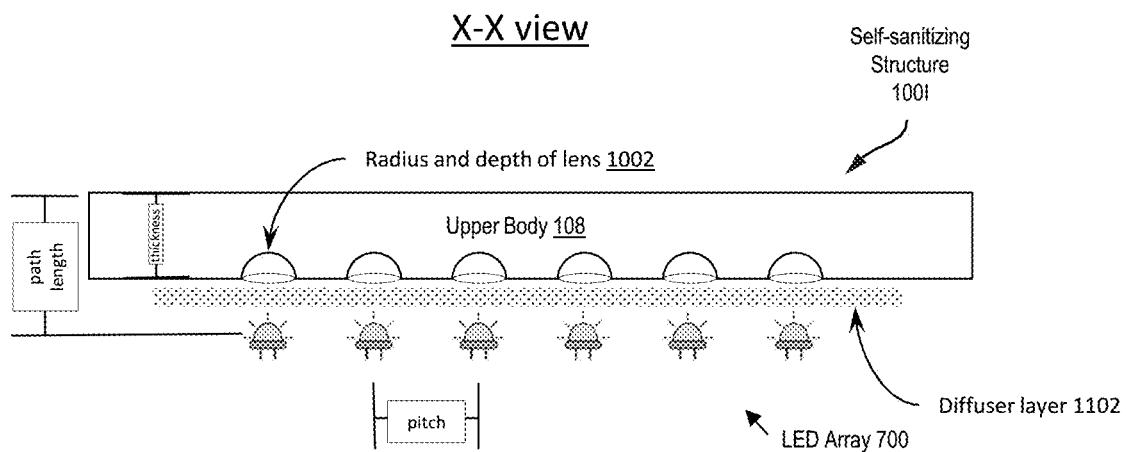
FIG. 11 depicts a cross-sectional view of a portion of the self-sanitizing structure shown in FIG. 1, which is taken along line X-X and depicts additional details of how an LED array, lensing elements, and a diffuser layer can be incorporated the self-sanitizing structure in accordance with embodiments of the invention.

FIG. 11 depicts a self-sanitizing structure 100I, which is a cross-sectional view of the self-sanitizing structure 100 taken along line X-X of FIG. 1. In accordance with aspects of the invention, the self-sanitizing structure 100I includes all of the features and functionality of the self-sanitizing structure 100G (shown in FIG. 10) and adds details of how a diffuser layer 1102 can be positioned between the LED array 700 and the lensing elements 1002 to enable further control and tuning of the shape, contour, and area of the light regions 114 in accordance with embodiments of the invention.

Figure 12:
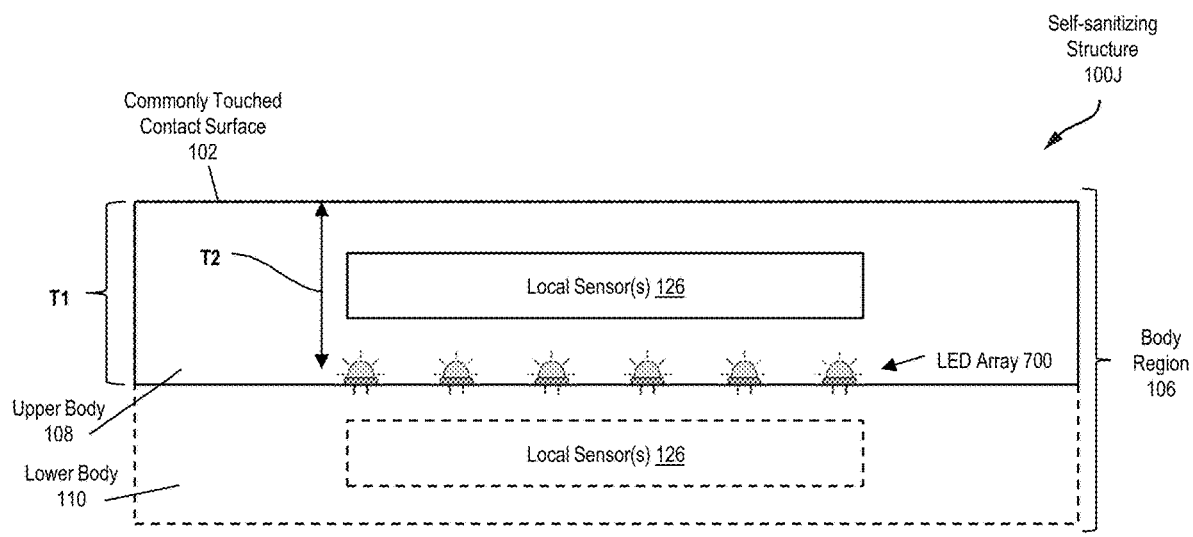
FIG. 12 depicts a cross-sectional view of the self-sanitizing structure shown in FIG. 1, which is taken along line X-X and depicts additional details of how an LED array and local sensor elements can be implemented in accordance with embodiments of the invention.

FIG. 12 depicts a self-sanitizing structure 100J, which is a cross-sectional view of the self-sanitizing structure 100 taken along line X-X of FIG. 1. In accordance with aspects of the invention, the self-sanitizing structure 100J includes all of the features and functionality of the self-sanitizing structure 100I (shown in FIG. 11) and adds details of how the local sensors 126 can be positioned between the LED array 700 and the contact surface 102 in accordance with embodiments of the invention. In some embodiments of the invention, the local sensors 126 can be positioned beneath the LED array 700 such that the LED array 700 is between the local sensors 126 and the contact surface 102 in accordance with embodiments of the invention. In some embodiments of the invention, the local sensors 126 can be integrated with the LED array 700 such that the LED array 700 and the local sensors 126 are substantially co-planar in accordance with aspects of the invention.

FIG. 13 depicts a block diagram illustrating how the local sensors 126 (shown in FIG. 12) can be implemented in the upper body 108A as translucent capacitive touch sensors 1302 in accordance with embodiments of the invention. A spacer 1304 is positioned between the LED array 700 and the translucent capacitive touch sensors 1302 to separate and isolate the electrical effects from the light surface potentials of the LED arrays 700. The capacitive touch sensors 1302 can be configured to include processing circuitry configured and arranged to detect capacitive changes at the sensor 1302 when a person reduces or otherwise alters electric fields generated by the capacitors of the capacitive touch sensors 1302 at a sufficient level to induce a detectable capacitive change at the sensor 1302. In accordance with aspects of the invention, when the user contacts the contact surface 102, a capacitive coupling path (represented by the capacitor of the capacitive sensor 1302) is created between the user and the capacitive touch sensor 1302. In accordance with aspects of the invention, the processing circuitry includes analog-to-digital conversion (ADC) circuitry configured and arranged to detect the capacitance (or capacitive coupling) generated by the touch event, along with a location of the touch event, and initiate an operation of a connected computing device (e.g., any of the processors 120, 150, 1510, 1710 described herein) in response thereto.

FIG. 14 depicts a block diagram illustrating how the local sensors 126 (shown in FIG. 12) can be implemented as force sensors 1402 in accordance with embodiments of the invention. In some embodiments of the invention, the force sensors 1402 can be implemented as a layer of piezoelectric and/or piezoresistive transducer material configured and arranged to generate a resistive and/or electrical output based at least in part on a mechanical input (pressure, force, or acceleration for example) applied to the contact surface 102. When force is applied to the force sensors 1402 through the contact surface 1402, the output (e.g., electrical) of the force sensor 1402 is proportional to the force applied. In embodiments of the invention, the force sensors 1402 can be provided with sufficient computing functionality to identify a location on the contact surface 102 where the mechanical input was applied, as well as analyze characteristics of the resistive and/or electrical output (e.g., the amount of force/pressure; the area of the contact surface 102 where the force/pressure was applied; and the like) to identify that the mechanical input was the result of a human touching the contact surface 102. In some embodiments of the invention, the computing functionality used to identify that the mechanical input was the result of a human touching the contact surface 102 can be implemented as machine learning algorithms configured to apply the outputs of the force sensors 1402 to a vector model of a human touching the contact surface 102 to classify when the outputs from the force sensors 1402 result from a human touching the contact surface 102. In some embodiments of the invention, the computing functionality used to identify that the mechanical input was the result of a human touching the contact surface 102 can be implemented as the local processor 120 and/or the remote processor 150 (shown in FIGS. 3 and 4).

FIGS. 15A-18 depict how self-sanitizing structures 1500, 1700 (shown in FIGS. 15A and 17A) can be configured to execute sanitization cycles 1530, 1722 (shown in FIGS. 15C and 17D) and sanitization patterns 1524, 1524A, 1722, 1722A (shown in FIGS. 15C, 15D, 17D, 17E) according to aspects of the invention. In embodiments of the invention, the features and functionality of the self-sanitizing structures 1500, 1700 can be implemented in any of the self-sanitizing structures described herein (e.g., self-sanitizing structures 100 and 100A-100J shown in FIGS. 1, 2A-2C, 3, 4, and 8-12). More specifically, the features and functionality of the integrated self-sanitizing systems 130F, 130G (shown in FIGS. 15A and 17A) can be implemented in any of the self-sanitizing systems self-sanitizing systems 130 and 130A-130E (shown in FIGS. 1, 2A-2C, 3 and 4); and the features and functionality of the processor systems 1510, 1710 can be incorporated into the processors 120, 150 (shown in FIGS. 2A-2D, 3 and 4).

FIG. 15A depicts the integrated self-sanitizing system 130F and the processor system 1510 of the self-sanitizing structure 1500 according to aspects of the invention. The integrated self-sanitizing system 130F includes addressable light source (LS) arrays 700A. In some embodiments of the invention, each of the addressable LS arrays 700A can be implemented as the addressable LED array 700 (shown in FIG. 7), wherein each LS of each array 700A is an LED (e.g., LED 702 or LED 712 shown in FIG. 7). In some embodiments of the invention, each LS of each array 700A can be implemented as a so-called "printed" LED, wherein each individually addressable LED is formed by printing microscopic vertical LEDs over a flexible or rigid substrate. Each LS in the arrays 700A is individually addressable or controllable by the processor system 1510. The term "addressable" is used herein to refer to a device having a unique "location" within an array or network of devices such that control signals can be sent to that specific device. In embodiments of the invention, the processor system 1510 can address control signals to one or more specific LS in any one of the addressable LS arrays 700A. Such control signals are referred to herein as individual LS control signals. In embodiments of the invention, the individual LS control signals can control a variety of LS control functions, including but not limited to turning the LS on/off; setting the amount of power applied to the LS; controlling whether the light generated by the LS is a continuous light wave or a pulsed light wave; where the light generated by the LS is pulsed, controlling the pulse width, frequency and/or duty cycle of the pulses; and the wavelength of the light generated by the LS; controlling the light output intensity levels.

Figure 16:
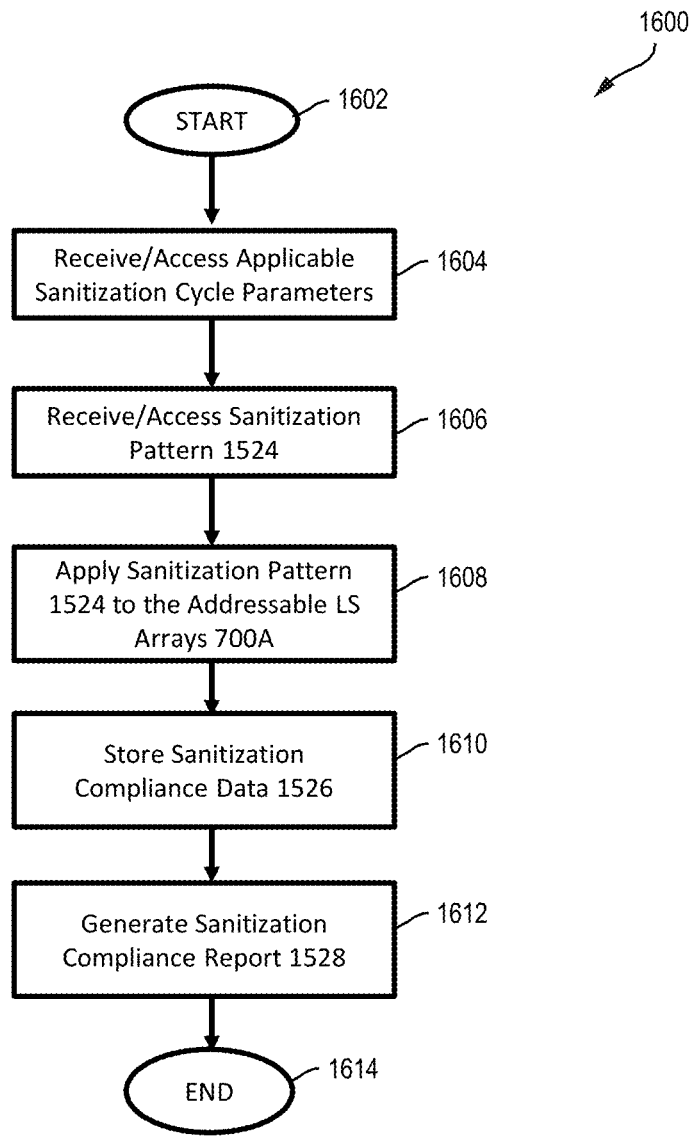
FIG. 16 depicts a flow diagram illustrating a methodology in accordance with embodiments of the invention.

The processor system 1510 is configured to include a memory 1520 having stored therein first mappings 1522, sanitization patterns 1524, and sanitization compliance data 1526. In some embodiments of the invention, the first mappings 1522 are a mapping of each individually addressable LS of each array 700A to a contact surface location 102B (shown in FIG. 15C) that receives sanitizing light that originated from that individually addressable LS provides sanitizing light. In some embodiments of the invention, and based on various design choices for the self-sanitizing structure 1500, the sanitizing light that reaches a contact surface location 102B can originate from more than one individually addressable LS. In some embodiments of the invention, the first mappings 1522 are generated by the processor system 1510. Additional details of how the first mappings 1522 can be generated are depicted in FIGS. 15B and 15C and described subsequently herein. The sanitization patterns 1524 are, in effect, a set of instructions that cause the processor system 1510 to apply the LS control signals to the addressable LS arrays 700A that are necessary to execute a sanitization cycle 1530 (shown in FIG. 15D). In embodiments of the invention, the sanitization cycle 1530 is a period of time (e.g., 1 hour, 2.5 hours, 3 hours and 10 minutes, and the like) during which the processor system 1510 controls the addressable LS arrays 700A to generate electromagnetic radiation that is scattered/dispersed through the body region 106 (shown in FIG. 1) of the self-sanitizing structure 100 to neutralize infectious agents on the touch surface 102. Additional details of how the sanitization patterns 1524 can be generated and used in accordance with aspects of the invention are depicted in FIGS. 15D, 15E, and 16 and described subsequently herein. The sanitization compliance data 1526 is data about various aspects of the sanitization patterns 1524 and sanitization cycles 1530 that have been completed. For example, the sanitization compliance data 1526 can include a start time, and end time, a duration, and an estimated infectious agent reduction level for a given sanitization pattern (e.g., sanitization pattern 1524A shown in FIG. 15E). In embodiments of the invention, the processor system 1510 uses the sanitization compliance data 1526 to generate sanitization compliance reports 1528. For example, in a hospital embodiment, it may be necessary to demonstrate that certain surfaces have been cleaned to a level that complies with government guidelines. The EPA performance standard for non-food contact sanitizers requires an infectious agent reduction level of about 99.9% (a 3-log reduction), and for disinfectants requires an infectious agent reduction level of about 99.9999% (a 6-log reduction). The processor system 1510 can be configured and to generate a sanitization compliance report 1528 designed to include sufficient supporting information to demonstrate that the integrated self-sanitizing system 130F has been used to comply with either of the previously-described EPA performance standards.

FIGS. 15B and 15C depict additional details of how the processor system 1510 can be configured to generate the first mappings 1522. The following descriptions of how the processor system 1524 can be configured to generate the first mappings 1522 refers to both the diagram depicted in FIG. 15B and the diagram depicted in FIG. 15C. As shown in FIG. 15B, the processor system 1510 includes one or more mapping algorithms 1532. The fundamental "mapping" function(s) of the mapping algorithm(s) 1532 are to identify a first type of data and a second type of data then associate the first and second types of data with one another according to a standard. In embodiments of the invention, the first type of data is data identifying each addressable LS in the arrays 700A; the second type of data is each of the contact surface locations 102B; and the "standard" is whether the addressable LS provides or contributes to providing sanitizing light to the contact surface location 102B. In some embodiments of the invention, the fundamental "mapping" function(s) of the mapping algorithm 1532 can be executed by an artisan having ordinary skill in the relevant arts using utilize known computer analysis techniques that do not require specialized computer functionality.

In some embodiments of the invention, the mapping algorithm 1532 can be configured and arranged to perform its fundamental "mapping" function(s) as follows. As shown in FIG. 15B, the mapping algorithm 1532 can be configured and arranged to receive and analyze the dimensions and topography (or roughness) of the contact surface 102 in order to divide the contact surface 102 into contact surface locations 102B each having of a predetermined or selected size, as well as a unique location on the contact surface 102. For example, the size of each contact surface location 102B can be a one (1) inch by one (1) inch square. In embodiments of the invention, both the size and the location of each contact surface location 102B is included in the data representing the contact surface locations 102B.

The mapping algorithm 1532 can be further configured and arranged to receive various sanitizing light parameters. As previously noted herein, the terms sanitizing light are used to reference the light (e.g., light 116 shown in FIGS. 3 and 4) that is generated by each addressable LS of the arrays 700A and scattered/dispersed/passed by the body region 106 (e.g., upper body 106A shown in FIG. 2A) in a controlled manner such that the light that reaches the contact surface 102 is maintained at an irradiance level above a minimum irradiance level that will neutralize infectious agents on the contact surface 102. Accordingly, the terms "sanitizing light parameters" refer to the various characteristics of the various elements that are used to generate and maintain sanitizing light at the contact surface 102 in accordance with aspects of the invention. In embodiments of the invention, the sanitizing light parameters of each addressable LS parameters include but are not limited to characteristics of the light 116 generated by each addressable LS in each array 700A; characteristics each addressable LS in each array 700A; and the upper body sanitization characteristics 106A. Examples of the characteristics/elements of the self-sanitizing structure 1500 that are used to generate and maintain sanitizing light at the contact surface 102 in accordance with aspects of the invention have been previously described herein, so in the interest of brevity they will not be repeated here. In embodiments of the invention, the mapping algorithm 1532 is configured and arranged to evaluate the sanitizing parameters to determine, for each addressable LS of the arrays 700A, a region of the contact surface where that addressable LS provides or contributes to providing sanitizing light.

At this stage of the operation of the mapping algorithm 1532, the fundamental "mapping" function(s) of the mapping algorithm 1532 can be performed, which, as previously-described, is to identify a first type of data and a second type of data then associate the first and second types of data with one another according to a standard. In the currently-described embodiments of the invention, the first type of data is data identifying both the size and the location of each contact surface location 102B; the second type of data is data representing, for each addressable LS of the arrays 700A, a region of the contact surface where that addressable LS provides or contributes to providing sanitizing light; and the "standard" is, for each contact surface location 102B, the addressable LS s that provides or contributes to providing sanitizing light to a region of the contact surface 102 that overlaps with the contact surface location 102B.

The previously-described associations identified by any of the previously-described mapping algorithm(s) 1532 are embodied in the first mappings 1522, which can be stored in a relational database of the processor system 1510. In general, a database is a means of storing information in such a way that information can be retrieved from it, and a relational database presents information in tables with rows and columns. A table is referred to as a relation in the sense that it is a collection of objects of the same type (rows). Data in a table can be related according to common keys or concepts, and the ability to retrieve related data from a table is the basis for the term relational database. A database management system (DBMS) of the processor system 1510 controls the way data in the memory 1520 is stored, maintained, and retrieved. A relational database management system (RDBMS) of the processor system 1510 performs the tasks of determining the way data and other information (e.g., the previously-described first type of data; second type of data; and the association of the first and second types of data with one another according to a standard) are stored, maintained and retrieved from the relational database of the processor system 1510.

FIG. 15D depicts additional details of how the processor system 1510 can be configured to execute the sanitization pattern(s) 1524 in accordance with aspects of the invention. As previously—described herein, the sanitization patterns 1524 are, in effect, a set of instructions that cause the processor system 1510 to control operating parameters of the addressable LS arrays 700A by, for example, applying the LS control signals to the addressable LS arrays 700A that are necessary to execute the sanitization cycle 1530 that achieves the estimated infectious agent reduction level at the contact surface 102. The operating parameters include the on/off status of each individually addressable LS in the arrays 700A, along with the power applied to each individually addressable LS in the arrays 700A. The processor system 1510 is configured to execute the sanitization pattern 1524 based at least in part on various sanitization cycle parameters, which can include the first mappings 1522; an estimate of the infections agent reduction level achieved at the contact surface 102; and/or whether the light generated by each LS of the array 700A is continuous wave or pulsed wave. In some embodiments of the invention, the estimated infectious agent reduction level at the contact surface 102 can be based on computer simulations of the self-sanitizing structure 1500; and/or actual infection agent reduction level measurements taken from example implementations of the self-sanitizing structure 1500. Although the sanitization cycle parameters are shown as inputs to the processor system 1510, in some embodiments of the invention, the sanitization cycle parameters are stored in parts of the processor system 1510 and accessed by the processor system 1510. The computer instructions of the sanitization patterns 1524 can be executed by the processor system 1510 to control activation/deactivation of each individually addressable LS in the arrays 700A; power levels applied to each individually addressable LS in the LS arrays 700A; and how long each individually addressable LS in the arrays 700A remains activated or deactivated. The previously-described sanitization compliance data 1526 (shown in FIG. 15A) stored in the memory 1520 of the processor system 1510 includes details of each sanitization pattern 1524 implemented by the processor system 1510 and the integrated self-sanitizing system 130F. The processor system 1510 is further configured to generate the previously-described sanitization compliance report(s) 1528, which, in embodiments of the invention, presents details of the sanitization compliance data 1526 and how the sanitization compliance data 1526 demonstrates compliance with a set of predetermined sanitization compliance standards.

FIG. 16 depicts a computer-implemented method 1600 that can be implemented by the processor system 1510 (as shown in FIG. 15D) in accordance with aspects of the invention. The following descriptions of the method 1600 make reference to the method 1600 shown in FIG. 16, as well as aspects of the processor system 1510 shown in FIGS. 15A, 15B and 15C that implement the method 1600. In embodiments of the invention, the operations of the method 1600 can be executed using known computer analysis techniques that do not require specialized computer functionality.

As shown in FIG. 16, the method 1600 starts at block 1602 then moves to block 1604 where the processor system 1510 receives/accesses applicable sanitization cycle parameters (e.g., sanitization cycle parameters 1531 shown in FIG. 15D), which can include applicable user/operator selections, if any. In some embodiments of the invention, various aspects of how the sanitization patterns 1524 are executed by the processor system 1510 are predetermined. In some embodiments of the invention, various aspects of how the sanitization patterns 1524 are executed by the processor system 1510 can be optionally selected by a user/operator of the integrated self-sanitizing system 130F including, for example, the selection of one of the sanitization patterns 1524 stored in the memory 1520. As previously-described herein, each of the sanitization patterns 1524 can include computer instructions executed by the processor system 1510 to set the operating parameters of the addressable LS arrays 700A (shown in FIG. 15A) during a sanitization cycle 1530. Also as previously noted herein, in embodiments of the invention, the sanitization cycle 1530 is a period of time (e.g., 1 hour; 2.5 hours; 3 hours and 10 minutes; and the like) during which the processor system 1510 controls the addressable LS arrays 700A to generate electromagnetic radiation that is scattered/dispersed through the body region 106 (shown in FIG. 1) of the self-sanitizing structure 100 to neutralize infectious agents on the touch surface 102. In some embodiments of the invention, the electromagnetic radiation can be a continuous wave of electromagnetic radiation. In some embodiments of the invention, the electromagnetic radiation can be a series of electromagnetic radiation pulses having a controlled pulse width, frequency and/or duty cycle. In some embodiments of the invention, multiple types of the sanitization patterns 1524 are stored in the processor system 1510 and the specific one of the sanitization patterns 1524 that will be executed by the processor system 1510 can be selected by the user/operator.

In some embodiments of the invention, a first type of the sanitization patterns 1524 can target sanitizing the entire contact surface 102 (shown in FIG. 15C). Accordingly, the first type of the sanitization patterns 1524 can include computer instructions configured to execute a sanitization cycle 1530 by controlling the activation/deactivation of each individually addressable LS in the LS arrays 700A; controlling power levels applied to each individually addressable LS in the LS arrays 700A; and controlling how long each individually addressable LS in the LS arrays 700A remains activated or deactivated. In general, there is an inverse relationship between the power levels applied to each individually addressable LS in the LS arrays 700A and a duration of the overall sanitization cycle 1530. For example, a higher power level applied to each individually addressable LS in the LS arrays 700A can achieve a desired infectious agent reduction level at the contact surface 102 in less time than a lower power level can achieve the same infectious agent reduction level.

In some embodiments of the invention, a second type of the sanitization patterns 1524 can target sanitizing a subset of the contact surface 102 (shown in FIG. 15C) by being configured to utilize the first mappings 1522 to control only the individually addressable LS of the LS arrays 700A that provide sanitizing light to the subset of the contact surface 102. For example, where the self-sanitizing structure 100 (shown in FIG. 1) is a large conference table, the subset of the contact surface 102 can be along a perimeter of the conference table's main support surface where users of the conference table are most likely to sit. Accordingly, the second type of the sanitization patterns 1524 can include computer instructions configured to execute the sanitization cycle 1530 by controlling the activation/deactivation of each individually addressable LS in the LS arrays 700A; controlling power levels applied to each individually addressable LS in the LS arrays 700A; and controlling how long each individually addressable LS in the LS arrays 700A remains activated or deactivated.

In some embodiments of the invention, the combination of sanitization cycle parameters that will achieve a desired infectious agent reduction level can be incorporated within the sanitization cycle parameters or can be selected by a user/operator. For example, the guidelines set forth by the EPA for disinfectants requires an infectious agent reduction level of about 99.9999% (a 6-log reduction). Accordingly, in some embodiments of the invention, the processor system 1510 can present a user with options for different infectious agent reduction levels. Upon receiving the user-selected sanitization pattern (e.g., the above-described first type of the sanitization patterns 1524; or the above-described second type of the sanitization patterns 1524) and the user-selected infectious agent reduction level, the processor system 1510 can present the user with additional options for achieving the user-selected infectious agent reduction level, including, for example, LS power levels; a duration of the sanitization cycle 1530; and whether the sanitizing light generated by each individually addressable LS in the arrays 700A is continuous wave or pulsed wave.

Upon receiving the user selections for the additional options, the processor system 1510 accesses one of the sanitation patterns 1524 at block 1606 then executes the accessed one of the sanitization patterns 1524 at block 1608 based on the user-selected options, if any. FIG. 15E depicts a sanitization pattern 1524A, which is an example of how the previously-described second type of the sanitization patterns 1524 can be executed at block 1608. In the example sanitization pattern 1524A, each individually addressable LS is implemented as an LED, and the processor system 1510 uses the first mappings 1522 to determine that LEDs A, B, and C provide sanitizing light to the subset of the contact surface 102; and to determine that LEDs D and E provide sanitizing light to the portion of the contact surface 102 that will not be sanitized. The sanitization pattern 1524A is based on achieving an infectious agent reduction level that complies with the EPA infectious agent reduction level standard of about 99.9999% (a 6-log reduction) for disinfectants. Additionally, the user/operator prioritizes sanitization cycles 1530 that preserve the useful life of LEDs A, B, C in order to provide a user-selected LED power input that keeps the sanitizing light at the contact surface 102 closer to the minimum light irradiance level 116A than the maximum light irradiance level 116B (shown in FIGS. 5A-5C). In some embodiments of the invention, the user-selected LED power input that keeps the sanitizing light at the contact surface 102 closer to the minimum light irradiance level 116A than the maximum light irradiance level 116B can be from about 0% to about 50% over the minimum light irradiance level 116A. Accordingly the sanitization cycle 1530 implemented by the sanitization pattern 1524A has a total duration of 6 hours. The sanitization cycle 1530 is divided into four (4) intervals of two (2) hours each. At Time 0, individually addressable LEDs A, B, C are ON, and individually addressable LEDs D, E are OFF. At Time 1, individually addressable LEDs A, B, C are ON, and individually addressable LEDs D, E are OFF. At Time 2, individually addressable LEDs A, B, C are ON, and individually addressable LEDs D, E are OFF. At Time 3, individually addressable LEDs A, B, C are OFF, and individually addressable LEDs D, E are also OFF. In some embodiments of the invention, any number of intervals can be provided having any desired duration.

Returning to the method 1600, at block 1610, upon completion of the sanitization cycle 1530 by the accessed type of the sanitization patterns 1524 (e.g., sanitization pattern 1524A), the processor system 1510 stores sanitization compliance data 1526 that records details of the how the sanitization cycle 1530 of the accessed type of the sanitization patterns 1524 was implemented. In embodiments of the invention, the sanitization compliance data 1526 can include, for example, the type of sanitization pattern used (e.g., the above-described first type of the sanitization patterns 1524; or the above-described second type of the sanitization patterns 1524); a start time of the sanitization cycle 1530; an end time of the sanitization cycle 1530; a duration of the sanitization cycle 1530; power levels applied to each individually addressable LS in the LS arrays 700A; an estimate of the infectious agent reduction level achieved at the contact surface 102 by the sanitization cycle 1530; and/or calculations and text explanations to support the accuracy of the estimate of the infectious agent reduction level at the contact surface 102 during the sanitization cycle 1530. At block 1612, the processor system 1510 can, optionally, generate a sanitization compliance report 1528 based on the sanitization compliance data 1526. In embodiments of the invention, the processor system 1510 can be configured to generate the sanitization compliance report 1528 in a variety of formats, including text, graphs, diagrams, charts, and the like. In embodiments of the invention, the sanitization compliance report 1528 can include any number of different sanitization cycles 1530. In some embodiments of the invention, the processor system 1510 can be configured to automatically generate a sanitization compliance report 1528 covering any number of sanitization cycles 1530 and transmit the sanitization compliance report 1528 to a remote computer, which can be a remote computer of an entity that tracks and monitors compliance with standards (e.g., EPA standards for infectious agent reduction levels for disinfectants). At block 1614, the method 1600 ends.

FIG. 17A depicts the integrated self-sanitizing system 130G and the processor system 1710 of the self-sanitizing structure 1700 according to aspects of the invention. The self-sanitizing structure 1700 is identical to the self-sanitizing structure 1500 (shown in FIG. 15A) except the integrated self-sanitizing system 130G includes the sensor system 126; and the processor system 1710 includes touch data records 1740 and second mappings 1760. Although different reference numbers are used in for certain elements in FIGS. 17A-17D, unless specifically stated otherwise, the processor system 1710 includes the features and functionality of the processor system 1510; the first mappings 1750 includes the features and functionality of the first mappings 1522; and the sanitization pattern(s) 1722 include the features and functionality of the sanitization pattern(s) 1524; the sanitization compliance data 1724 includes the features and functionality of the sanitation compliance data 1526; and the sanitation compliance report(s) 1726 include the features and functionality of the sanitization compliance report(s) 1528. In the interest of brevity, the features and functionality that the self-sanitizing structure 1700 has in common with the self-sanitizing structure 1500 are not repeated, and only the features and functionality of the self-sanitizing structure 1700 that are not present in the self-sanitizing structure 1500 will be described.

The integrated self-sanitizing system 130G includes addressable light source (LS) arrays 700A. In some embodiments of the invention, each of the addressable LS arrays 700A can be implemented as the addressable LED array 700 (shown in FIG. 7), wherein each LS of each array 700A is an LED (e.g., LED 702 or LED 712 shown in FIG. 7). In some embodiments of the invention, each LS of each array 700A can be implemented as a so-called "printed" LED, wherein each individually addressable LED is formed by printing microscopic vertical LEDs over a flexible or rigid substrate. Each LS in the arrays 700A is individually addressable or controllable by the processor system 1510. The term "addressable" is used herein to refer to a device having a unique "location" within an array or network of devices such that control signals can be sent to that specific device. In embodiments of the invention, the processor system 1510 can address control signals to one or more specific LS in any one of the addressable LS arrays 700A. Such control signals are referred to herein as individual LS control signals. In embodiments of the invention, the individual LS control signals can control a variety of LS control functions, including but not limited to turning the LS on/off; setting the amount of power applied to the LS (changing light output intensity); controlling whether the light generated by the LS is a continuous light wave or a pulsed light wave; where the light generated by the LS is pulsed, controlling the pulse width, frequency and/or duty cycle of the pulses; and the wavelength of the light generated by the LS. In some embodiments of the invention, each LS of the LED array 700 can be provided with an integrated driver chip configured and arranged to provide some or all of the individual LS control signals.

The integrated self-sanitizing system 110G includes a sensor system 126, and a memory 1720 of the processor system 1710 includes a relational database 1730 having stored therein touch data records 1740, first mappings 1750, and second mappings 1760. Additionally, as explained in greater detail subsequently herein, the sanitization patterns 1722 can include all of the features and functions of the sanitization patterns 1524, 1524A (shown in FIGS. 15A, 15D, and 15E), along with additional features and functionality that are created by the processor system 1710 based on analysis of the touch data records 1740. In embodiments of the invention, the touch data records 1740 are generated based on touch data 1772 (shown in FIG. 17C) generated by the sensor system 126.

In embodiments of the invention, the sensor system 126 generally corresponds to the local sensors 126 (shown in FIGS. 5 and 6), and more specifically corresponds to the capacitive sensors 1302 (shown in FIG. 13) and/or the force sensors 1402 (shown in FIG. 14). In accordance with embodiments of the invention, the sensor system 126 is configured to translate instances of a person (or persons) touching the contact surface 102 to the touch data 1770 (shown in FIG. 17C) that represents locations on the contact surface 102 where the person (or persons) contacted the contact surface 102. In some embodiments of the invention, the processor system 1710 is configured to access or receive the touch data 1770 using any suitable technique for accessing/receiving data readings from sensors, including, for example by polling the sensor system 126 and/or by configuring the sensor system 126 to automatically transmit periodic touch data to the processor system 1710.

In embodiments of the invention, the memory 1720 includes a relational database 1730 that stores the touch data records 1740, the first mappings 1750, and the second mappings 1760. In general, a database is a means of storing information in such a way that information can be retrieved from it, and a relational database presents information in tables with rows and columns. A table is referred to as a relation in the sense that it is a collection of objects of the same type (rows). Data in a table can be related according to common keys or concepts, and the ability to retrieve related data from a table is the basis for the term relational database. A database management system (DBMS) of the processor system 1710 controls the way data in the memory 1720 is stored, maintained, and retrieved. A relational database management system (RDBMS) of the processor system 1710 performs the tasks of determining the way data and other information (e.g., touch data records 1740, first mappings 1750, and/or second mappings 1760) are stored, maintained and retrieved from the relational database 1730.

FIG. 17B depicts a simplified block diagram of the sensor system 126 in communication with portions of the processor system 1710. In embodiments of the invention, the sensor system 126 generates touch data 1770 that includes timestamp data 1772 and touch readings 1774. In embodiments of the invention, processor system 1710 is configured to receive or access the touch data 1770 generated by the sensor system 126; generate touch data records 1732 from the touch data 1770; and store the generated touch data records 1732 in the relational database 1730. In embodiments of the invention, each of the touch data records 1732 includes touch-related time data 1734 and touch-related location data 1736. In some embodiments of the invention, the sensor system 126 can include sufficient processor functionality to associate a given touch reading 1774 with timestamp data 1772 (e.g., touch reading A occurred at 9:00 am). In some embodiments of the invention, the processor system 1710 performs the task of associating touch readings 1774 with timestamp data 1772.

In embodiments of the invention, the touch-related location data 1736 can be derived from the raw touch readings 1774 and configured to include data identifying one or more locations on the contact surface 102 where the touch instance sensed by the sensor system 126 occurred. For example, if the contact surface 102 is a main support surface of a conference table, and a person rests her bare palm 1780 (shown in FIG. 17C) on the main support surface for one (1) minute then removes it, the sensor system 126 would sense this touch instance by generating timestamp data 1772 and associated touch readings 1774. In embodiments of the invention, the timestamp data 1772 is raw in that it simply generates a timestamp for each touch readings 1774. In embodiments of the invention, the touch readings 1774 are raw in that they simply generate a touch reading 1774 based on a touch instance starting or a touch instance ending. In embodiments of the invention, the touch readings 1774 also include data that indicates the locations on the contact surface 102 where the person's forearm touched the contact surface 102.

In embodiments of the invention, the processor system 1710 accesses or receives the raw timestamp data 1772 and the associated raw touch readings 1774 then generates therefrom touch-related time data 1734 and touch-related location data 1736. In the example where the contact surface 102 is the main support surface of a conference table, the processor would receive raw timestamp data 1772 and associated touch readings 1774 indicating that at 9:30 am a touch instance started at locations A-D on the main support surface of the conference table; and further indicating that at 9:31 am the touch instance that started at 9:30 am at locations A-D on the main support surface of the conference table ended. The processor system 1710 analyzes the raw timestamp data 1772 and associated touch readings 1774 and generates therefrom the touch-related time data 1734 and the touch-related location data 1736.

The analysis performed by processor systems 1710 will now be described with reference to FIGS. 17B and 17C. In FIG. 17C, the first mappings 1750 have already been created. The first mappings 1750 are a mapping of each individually addressable LS of each array 700A to a contact surface location 102B (shown in FIG. 17C) that receives sanitizing light that originated from that individually addressable LS provides sanitizing light. FIG. 17C depicts a block diagram illustrating how a user 1780 touching certain contact surface locations 102B on the contact surface 102 causes the processor 1710 generate and store touch data records 1732 in accordance with embodiments of the invention. Returning to the analysis performed by the processor system 1710, the processor system 1710 determines that the touch instances recorded through touch readings 1774 starting at 9:30 am at locations A-D on the main support surface of the conference table are related to one another as a single touch instance. The touch-related time data generated by the processor system 1710 includes a start time (e.g., 9:30 am), an end time (e.g., 9:31 am), and a duration (e.g., 1 minute) of the person 1780 resting the palm of her hand on the main support surface of the conference table. The touch-related location data 1774 generated by the processor system 1710 include data identifying the locations A-D touched by the user 1780 resting her hand on the main support surface of the conference table. The processor system 1710 uses the first mappings 1750 to identify the contact locations 102B that corresponds to the locations A-D touched by the user 1780, which allows the processor system 1710 to generate second mappings 1760 that identify each individually addressable LS of the array 700A that supplies sanitizing light to contact surface locations 102B that corresponds to the locations A-D touched by the user 1780. In embodiments of the invention, the processor system 1710 can add to the touch-related location data 1736 data identifying each individually addressable LS of the array 700A that supplies sanitizing light to contact surface locations 102B that corresponds to the locations A-D touched by the user 1780. In some embodiments of the invention, the processor system 1710 can be configured to store the data identifying each individually addressable LS of the array 700A that supplies sanitizing light to contact surface locations 102B that corresponds to the locations A-D touched by the user 1780 in a separate portion of the touch data record 1732 to be accessed during generation of the sanitization patterns data touch-related time data 1734 and the touch-related location data 1736 as a touch data record 1732 in the relational database 1730 for subsequent use by the processor system 1710 when generating the sanitization patterns 1722, 1722A, which are shown in FIGS. 17D and 17E and described in greater detail subsequently herein.

FIG. 17D depicts additional details of how the processor system 1710 can be configured to both execute stored sanitization patterns (e.g., sanitization patterns 1524, 1524A shown in FIGS. 15D and 15E) and generate sanitization patterns (e.g., sanitization patterns 1722, 1722A shown in FIGS. 17A, 17D, and 17E) using a sanitization pattern/cycle generation (SPCG) algorithm 1762. As previously noted, the processor system 1710 executes stored sanitization patterns in substantially the same manner as the processor system 1510 (shown in FIGS. 15A, 15B and 15D). Accordingly the description of FIG. 17D will focus on the features and functionality for generating and executing the sanitization patterns 1722, 1722A. The sanitization patterns 1722, 1722A are, in effect, a set of instructions that cause the processor system 1710 to control operating parameters of the addressable LS arrays 700A by, for example, applying the LS control signals to the addressable LS arrays 700A that are necessary to execute the sanitization cycle 1782 that achieves the estimated infectious agent reduction level at the contact surface 102. The operating parameters include the on/off status of each individually addressable LS in the arrays 700A, along with the power applied to each individually addressable LS in the arrays 700A. The processor system 1710 is configured to execute the sanitization patterns 1722, 1722A based at least in part on the touch data records 1732 and various sanitization cycle parameters 1783, which can include the second mappings 1760; an estimate of the infections agent reduction level achieved at the contact surface 102; and/or whether the light generated by each LS of the array 700A is continuous wave or pulsed wave. In some embodiments of the invention, the estimated infectious agent reduction level at the contact surface 102 can be based on computer simulations of the self-sanitizing structure 1700; and/or actual infection agent reduction level measurements taken from example implementations of the self-sanitizing structure 1700. Although the sanitization cycle parameters 1783 are shown as inputs to the processor system 1710, in some embodiments of the invention, the sanitization cycle parameters 1783 are stored in parts of the processor system 1710 and accessed by the processor system 1710.

In accordance with aspects of the invention, the processor system 1710 includes the previously-described stored sanitization patterns 1524 having multiple types, along with the SPCG algorithm 1762 configured and arranged to generate the sanitization cycle 1782 and the sanitization patterns 1722, 1722A. In some embodiments of the invention, the SPCG algorithm 1762 is configured and arranged to generate the sanitization cycle 1782 and the sanitization patterns 1722, 1722A by making appropriate modifications to the stored sanitization patterns 1524.

Figure 18:
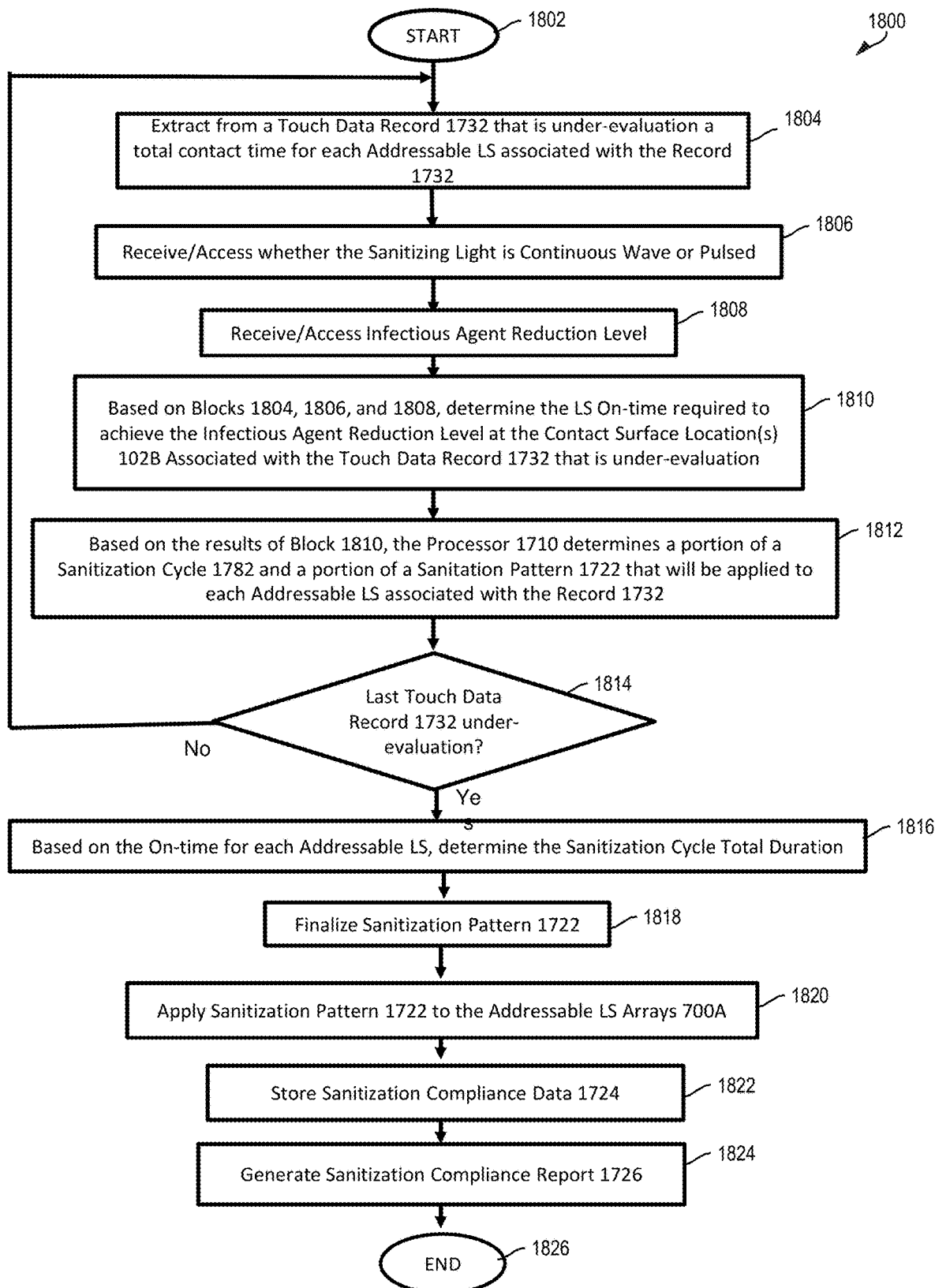
FIG. 18 depicts a flow diagram illustrating a methodology in accordance with embodiments of the invention.

FIG. 18 depicts a computer-implemented method 1800 in which the processor system 1710 uses the SPCG algorithm 1762 to generate and apply the sanitization cycle 1782 and the sanitization patterns 1722, 1722A in accordance with embodiments of the invention. The following descriptions of the method 1800 makes reference to the method 1800 shown in FIG. 18, as well as aspects of the processor system 1710 shown in FIGS. 17A-17C that implement the method 1800. As shown in FIG. 18, the method 1800 starts at block 1802 then moves to block 1804. At block 1804 the processor system 1710 accesses a first (or next) touch data record 1732 that is under-evaluation then extracts from the touch data records 1732 a total contact time for each addressable LS that is associated with the touch data record 1732 that is under-evaluation. For example, in the previously-describe example wherein the contact surface 102 is a main support surface of a conference table, the total contact time for the touch data record 1732 in that example is one (1) minute, and the second mappings 1760 were used to identify each individually addressable LS of the array 700A that supplies sanitizing light to contact surface locations 102B that corresponds to the locations A-D touched by the user 1780. Accordingly, block 1804 assigns a one (1) minute contact time to each individually addressable LS of the array 700A that supplies sanitizing light to contact surface locations 102B that corresponds to the locations A-D touched by the user 1780.

At block 1806, the method 1800 receives/accesses information indicating whether the sanitizing light is continuous wave or a pulsed wave. At block 1808, the method 1800 receives/accesses information indicating the desired infectious agent reduction level to be achieved by the sanitization patterns 1722, 1722A and the sanitization cycle 1782.

At block 1810, the method 1800 uses the SPCG algorithm 1762 to determine, based on blocks 1804, 1806, and 1808, the LS on-time required to achieve the desired or targeted infectious agent reduction level at the contact surface location(s) 102B associated with each addressable LS identified at block 1804. For example, in the previously-describe example wherein the contact surface 102 is a main support surface of a conference table, the total contact time for the touch data record 1732 in that example is one (1) minute, and the second mappings 1760 were used to identify each individually addressable LS of the array 700A that supplies sanitizing light to contact surface locations 102B that corresponds to the locations A-D touched by the user 1780. At block 1810, the SPCG algorithm 1762 is configured to determine that each individually addressable LS of the array 700A that supplies sanitizing light to contact surface locations 102B that corresponds to the locations A-D touched by the user 1780 must be activated for three (3) minutes to achieve the desired/targeted infectious agent reduction level at the locations A-D. Accordingly, at block 1810, the method 1800 assigns an on-time of three (3) minutes to each individually addressable LS of the array 700A that supplies sanitizing light to contact surface locations 102B that corresponds to the locations A-D touched by the user 1780. In some embodiments of the invention, the SPCG algorithm 1762 is configured to determine the required on-time of each individually addressable LS of the array 700A that supplies sanitizing light to contact surface locations 102B that corresponds to the locations A-D touched by the user 1780 based on computer simulations of the self-sanitizing structure 1700; and/or actual infection agent reduction level measurements taken from example implementations of the self-sanitizing structure 1700.

At block 1812, the method 1800 uses the results of block 1810 to determine a portion of the sanitization cycle 1782 and a portion of the sanitization pattern 1722 that will be applied to each addressable LS associated with the touch data record 1732 that is under-evaluation.

The method 1800 moves to decision block 1814 to determine whether the touch data record 1732 evaluated at blocks 1804-1812 is the last touch data record 1732 that needs to be evaluated. If the answer to the inquiry at decision block 1814 is no, the method 1800 returns to block 1804 to evaluate the next stored touch data record 1732. If the answer to the inquiry at decision block 1814 is yes, the method 1800 moves to block 1816 and adds up the LS on-times assigned during the iterations of blocks 1804-1812 to determine the total duration of the sanitization cycle 1782.

At block 1818, the method 1800 uses the LS on-time assignments generated by the iterations of blocks 1804-1812 to determine a final sanitization pattern 1722; and at block 1820, the method 1800 applies the final sanitization pattern 1722 to the addressable LS arrays 700A. FIG. 17E depicts a simplified example sanitization pattern 1722A that is an example of a final sanitization pattern that can be generated at block 1818. In the sanitization pattern 1722A, the individually addressable LS array 700A is implemented as an array of individually addressable LEDs A-E. In the example sanitization pattern 1722A, the processor system 1710 uses the iterations of blocks 1804-1812 to determine that LEDs A and B provide sanitizing light to contact surface locations 102B that were touched for a total duration that requires a two (2) hour application of sanitizing light to achieve the desired/target infectious agent reduction level at the contact surface 102; that LEDs C and D provide sanitizing light to contact surface locations 102B that were touched for a total duration that requires a six (6) hour application of sanitizing light to achieve the desired/target infectious agent reduction level at the contact surface 102; and that LED E provides sanitizing light to contact surface locations 102B on the contact surface that were not touched. In embodiments of the invention, the sanitization pattern 1722A is based on achieving an infectious agent reduction level that complies with the EPA infectious agent reduction level standard of about 99.9999% (a 6-log reduction) for disinfectants. Additionally, the user/operator prioritizes sanitization cycles 1782 that preserve the useful life of LEDs A-D so has provided a user-selected LED power input that keeps the sanitizing light at the contact surface 102 closer to the minimum light irradiance level 116A than the maximum light irradiance level 116B (shown in FIGS. 5A-5C). In some embodiments of the invention, the user-selected LED power input that keeps the sanitizing light at the contact surface 102 closer to the minimum light irradiance level 116A than the maximum light irradiance level 116B can be from about 0% to about 50% over the minimum light irradiance level 116A. Accordingly the sanitization cycle 1782 implemented by the sanitization pattern 1722A has a total duration of 6 hours. The sanitization cycle 1782 is divided into four (4) intervals of two (2) hours each. At Time 0, individually addressable LEDs A-D are ON, and individually addressable LED E is OFF. At Time 1, individually addressable LEDs C and D are ON, and individually addressable LEDs A, B, and E are OFF. At Time 2, individually addressable LEDs C and D are ON, and individually addressable LEDs A, B, and E are OFF. At Time 3, individually addressable LEDs A-E are OFF. In some embodiments of the invention, any number of intervals can be provided having any desired duration.

At block 1822, the method 1800 stores in the memory 1720 sanitization compliance data 1724 that includes information data about various aspects of the sanitization patterns 1722 and the sanitization cycles 1782 that have been completed.

At block 1824, the method 1800 uses the processor system 1710 to generate a sanitization compliance report 1726 designed to include sufficient supporting information to demonstrate that the integrated self-sanitizing system 130G has been used to comply with either of the previously-described EPA performance standards. The method 1800 ends at block 1826.

Figure 19:
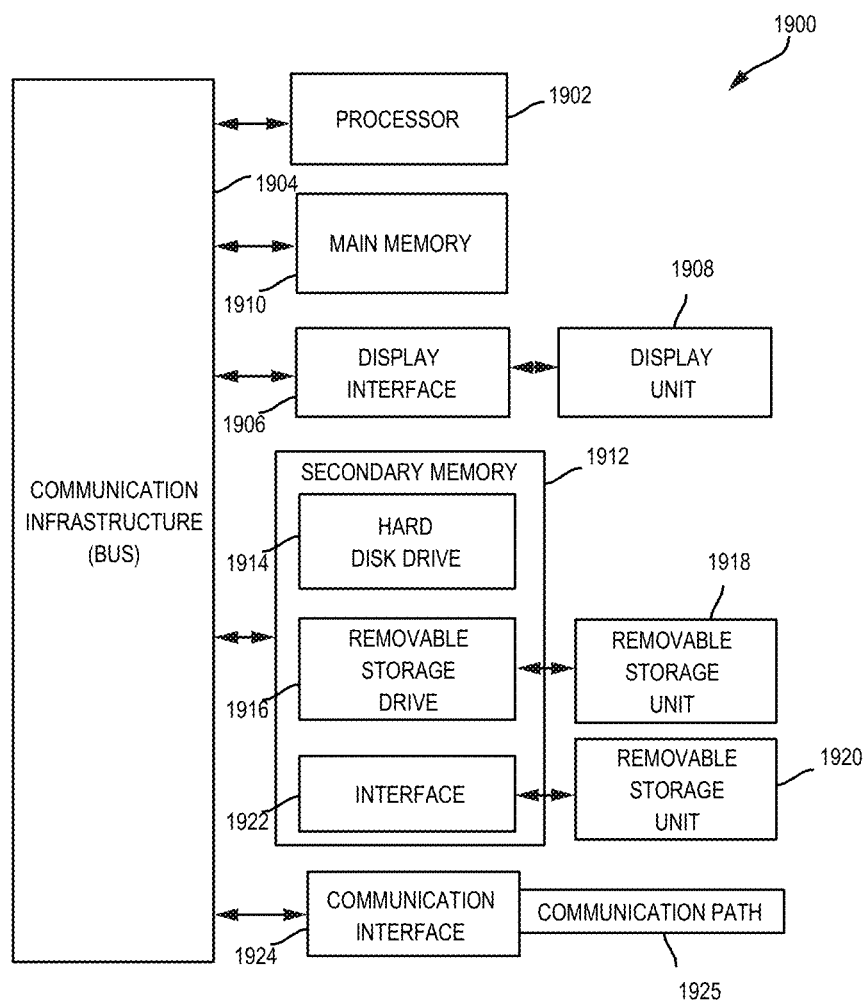
FIG. 19 depicts details of an exemplary computing system capable of implementing various aspects of the invention.

FIG. 19 depicts a high level block diagram of the computer system 1900, which can be used to implement one or more computer processing operations in accordance with aspects of the invention. Although one exemplary computer system 1900 is shown, computer system 1900 includes a communication path 1926, which connects computer system 1900 to additional systems (not depicted) and can include one or more wide area networks (WANs) and/or local area networks (LANs) such as the Internet, intranet(s), and/or wireless communication network(s). Computer system 1900 and additional system are in communication via communication path 1926, e.g., to communicate data between them.

Computer system 1900 includes one or more processors, such as processor 1902. Processor 1902 is connected to a communication infrastructure 1904 (e.g., a communications bus, cross-over bar, or network). Computer system 1900 can include a display interface 1906 that forwards graphics, text, and other data from communication infrastructure 1904 (or from a frame buffer not shown) for display on a display unit 1908. Computer system 1900 also includes a main memory 1910, preferably random access memory (RAM), and can also include a secondary memory 1912. Secondary memory 1912 can include, for example, a hard disk drive 1914 and/or a removable storage drive 1916, representing, for example, a floppy disk drive, a magnetic tape drive, or an optical disk drive. Removable storage drive 1916 reads from and/or writes to a removable storage unit 1918 in a manner well known to those having ordinary skill in the art. Removable storage unit 1918 represents, for example, a floppy disk, a compact disc, a magnetic tape, or an optical disk, flash drive, solid state memory, etc. which is read by and written to by removable storage drive 1916. As will be appreciated, removable storage unit 1918 includes a computer readable medium having stored therein computer software and/or data.

In alternative embodiments, secondary memory 1912 can include other similar means for allowing computer programs or other instructions to be loaded into the computer system. Such means can include, for example, a removable storage unit 1920 and an interface 1922. Examples of such means can include a program package and package interface (such as that found in video game devices), a removable memory chip (such as an EPROM, or PROM) and associated socket, and other removable storage units 1920 and interfaces 1922 which allow software and data to be transferred from the removable storage unit 1920 to computer system 1900.

Computer system 1900 can also include a communications interface 1924. Communications interface 1924 allows software and data to be transferred between the computer system and external devices. Examples of communications interface 1924 can include a modem, a network interface (such as an Ethernet card), a communications port, or a PCM-CIA slot and card, etcetera. Software and data transferred via communications interface 1924 are in the form of signals which can be, for example, electronic, electromagnetic, optical, or other signals capable of being received by communications interface 1924. These signals are provided to communications interface 1924 via communication path (i.e., channel) 1926. Communication path 1926 carries signals and can be implemented using wire or cable, fiber optics, a phone line, a cellular phone link, an RF link, and/or other communications channels.

In the present description, the terms "computer program medium," "computer usable medium," "computer program product," and "computer readable medium" are used to generally refer to media such as main memory 1910 and secondary memory 1912, removable storage drive 1916, and a hard disk installed in hard disk drive 1914. Computer programs (also called computer control logic) are stored in main memory 1910 and/or secondary memory 1912. Computer programs can also be received via communications interface 1924. Such computer programs, when run, enable the computer system to perform the features of the invention as discussed herein. In particular, the computer programs, when run, enable processor 1902 to perform the features of the computer system. Accordingly, such computer programs represent controllers of the computer system.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Many of the functional units described in this specification have been labeled as modules. Embodiments of the invention apply to a wide variety of module implementations. For example, a module can be implemented as a hardware circuit comprising custom VLSI circuits or gate arrays, off-the-shelf semiconductors such as logic chips, transistors, or other discrete components. A module can also be implemented in programmable hardware devices such as field programmable gate arrays, programmable array logic, programmable logic devices or the like.

Modules can also be implemented in software for execution by various types of processors. An identified module of executable code can, for instance, include one or more physical or logical blocks of computer instructions which can, for instance, be organized as an object, procedure, or function. Nevertheless, the executables of an identified module need not be physically located together, but can include disparate instructions stored in different locations which, when joined logically together, comprise the module and achieve the stated purpose for the module.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, a process, a method, an article, or an apparatus that comprises a list of elements is not necessarily limited to only those elements but can include other elements not expressly listed or inherent to such composition, mixture, process, method, article, or apparatus.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

Additionally, the term "exemplary" and variations thereof are used herein to mean "serving as an example, instance or illustration." Any embodiment or design described herein as "exemplary" is not necessarily to be construed as preferred or advantageous over other embodiments or designs. The terms "at least one," "one or more," and variations thereof, can include any integer number greater than or equal to one, i.e. one, two, three, four, etc. The terms "a plurality" and variations thereof can include any integer number greater than or equal to two, i.e., two, three, four, five, etc. The term "connection" and variations thereof can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The terms "sanitize, "sanitization," and derivatives thereof are used herein to mean any point along a process that, at its completion, reaches an infectious agent reduction level in accordance with an applicable guideline set forth by the United States Environmental Protection Agency (EPA). For example, the EPA performance standard for non-food contact sanitizers requires an infectious agent reduction level of about 99.9% (a 3-log reduction). The EPA performance standard for disinfectants requires an infectious agent reduction level of about 99.9999% (a 6-log reduction).

The terms "light scattering," "electromagnetic radiation scattering," "radiation scattering," and equivalents thereof are used herein to refer to the actions of scattering elements having a sufficient size (or size distribution) to throw light that interacts with the scattering elements in various random directions, wherein the size (or size distribution) of the scattering elements is from about 50 nanometers in diameter to about 50 micrometers in diameter, assuming there is a sufficient index of refraction mismatch between the scattering elements and the matrix material that houses the scattering elements.

The phrases "in communication with," "communicatively coupled to," and variations thereof can be used interchangeably herein and can refer to any coupling, connection, or interaction using electrical signals to exchange information or data, using any system, hardware, software, protocol, or format, regardless of whether the exchange occurs wirelessly or over a wired connection.

Aspects of the invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the invention. In this regard, each block in the flowchart or block diagrams may represent a module, segment, or portion of instructions, which comprises one or more executable instructions for implementing the specified logical function (s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

It will be understood that those skilled in the art, both now and in the future, may make various improvements and enhancements which fall within the scope of the claims which follow.

What is claimed is:

1. A self-sanitizing structure comprising:
   a body region having a contact surface that can be contacted by a person during an intended use of the self-sanitizing structure; and
   an energy source comprising an array of individually addressable energy sources, wherein the energy source is configured to:
     generate electromagnetic radiation; and
     direct the electromagnetic radiation through the body region to the contact surface;
   wherein the contact surface is communicatively coupled to a sensor system;
   wherein the energy source and the sensory system are communicatively coupled to a controller;
   wherein the body region is configured to perform irradiance control operations that comprise scattering the electromagnetic radiation and passing the scattered electromagnetic radiation through the body region to the contact surface in a manner that maintains the scattered electromagnetic radiation that reaches the contact surface as sanitizing electromagnetic radiation;
   wherein the sanitizing electromagnetic radiation is electromagnetic radiation that is at or above a minimum irradiance level that neutralizes infectious agents;
   wherein the sensor system is configured to generate touch data in response to the contact surface being touched;
   wherein the controller is configured to use the touch data to control how the energy source generates the electromagnetic radiation by controlling the individually addressable energy sources;
   wherein the controller is further configured to control the individually addressable energy sources by performing controller operations comprising generating from the touch data a touch data record comprising:
     touch-related location data that identifies a location on the contact surface where a touch instance occurred; and
     touch-related time data that identifies a duration of the touch instance on the contact surface.

2. The self-sanitizing structure of claim 1, wherein the controller operations further comprise identifying, based at least in part on the touch-related location data, the set of the individually addressable energy sources that will, when instructed to do so, generate at least one instance of the electromagnetic radiation that results in the sanitizing electromagnetic being maintained at the location on the contact surface where the touch instance occurred.

3. The self-sanitizing structure of claim 2, wherein the controller operations further comprise generating a sanitization pattern comprising instructions to the set of the individually addressable energy sources to generate, for a duration, the at least one instance of the electromagnetic radiation that results in the sanitizing electromagnetic being maintained at the location on the contact surface where the touch instance occurred.

4. The self-sanitizing structure of claim 3, wherein the duration is sufficient to neutralize infectious agents at the location on the contact surface where the touch instance occurred.

5. The self-sanitizing structure of claim 4, wherein the controller operations further comprise executing the sanitization pattern.

6. The self-sanitizing structure of claim 5, wherein the controller operations further comprise storing in a memory of the controller sanitization compliance data comprising results of executing the sanitization pattern.

7. The self-sanitizing structure of claim 6 wherein the controller operations further comprise generating a sanitization compliance report based at least in part on the sanitization compliance data.

8. The self-sanitizing structure of claim 2, wherein identifying, based at least in part on the touch-related location data, the set of the individually addressable energy sources that will, when instructed to do so, generate the at least one instance of the electromagnetic radiation that results in the sanitizing electromagnetic radiation being maintained at the location on the contact surface where the touch instance occurred comprises utilizing a first mapping of the set of individually addressable energy sources to contact surface locations on the contact surface.

9. The self-sanitizing structure of claim 8, wherein:
   each of the individually addressable energy sources, when activated, projects onto the contact surface the sanitizing electromagnetic radiation, wherein the sanitizing electromagnetic radiation on the contact surface has a sanitizing electromagnetic energy footprint; and
   the first mapping associates the sanitizing electromagnetic radiation footprint of each of the individually addressable energy sources with one or more of the contact surface locations.

10. A self-sanitizing structure comprising:
    a body region having a contact surface that can be contacted by a person during an intended use of the self-sanitizing structure; and
    an energy source comprising an array of individually addressable energy sources;
    wherein the energy source is configured to:
      generate electromagnetic radiation; and
      direct the electromagnetic radiation through the body region to the contact surface;
    wherein a controller is configured to control the individually addressable energy sources by performing controller operations comprising:
      generating a touch data record associated with one or more touch instances on the contact surface; and using the touch data record to control one or more individually addressable energy sources to control how the energy source generates the electromagnetic radiation.

11. The self-sanitizing structure of claim 10, wherein:
the contact surface is communicatively coupled to a sensor system;
the energy sources is communicatively coupled to a controller and the sensor system
the body region is configured to scatter the electromagnetic radiation and pass the scattered electromagnetic radiation through the body region to the contact surface in a manner that maintains the scattered electromagnetic radiation that reaches the contact surface as sanitizing electromagnetic radiation;
the sanitizing electromagnetic radiation is electromagnetic radiation that is at or above a minimum irradiance level that neutralizes infectious agents; and
the sensor system is configured to generate touch data in response to the contact surface being touched.

12. The self-sanitizing structure of claim 11, wherein the controller operations further comprise:
generating from the touch data the touch data record;
wherein the touch data record comprises:
touch-related location data that identifies a location on the contact surface where a touch instance occurred; and
touch-related time data that identifies a duration of the touch instance on the contact surface.

13. The self-sanitizing structure of claim 12, wherein the controller operations further comprise identifying, based at least in part on the touch-related location data, a set of the individually addressable energy sources that will, when instructed to do so, generate at least one instance of the electromagnetic radiation that results in the sanitizing electromagnetic being maintained at the location on the contact surface where the touch instance occurred.

14. The self-sanitizing structure of claim 13, wherein the controller operations further comprise generating a sanitization pattern comprising instructions to the set of the individually addressable energy sources to generate, for a duration, the at least one instance of the electromagnetic radiation that results in the sanitizing electromagnetic radiation being maintained at the location on the contact surface where the touch instance occurred.

15. The self-sanitizing structure of claim 14, wherein the duration is sufficient to neutralize infectious agents at the location on the contact surface where the touch instance occurred.

16. The self-sanitizing structure of claim 15, wherein the controller operations further comprise executing the sanitization pattern.

17. The self-sanitizing structure of claim 16, wherein the controller operations further comprise:
storing in a memory of the controller sanitization compliance data comprising results of executing the sanitization pattern; and
generating a sanitization compliance report based at least in part on the sanitization compliance data.

18. The self-sanitizing structure of claim 13, wherein identifying, based at least in part on the touch-related location data, the set of the individually addressable energy sources that will, when instructed to do so, generate the at least one instance of the electromagnetic radiation that results in the sanitizing electromagnetic being maintained at the location on the contact surface where the touch instance occurred comprises utilizing a first mapping of the set of individually addressable energy sources to contact surface locations on the contact surface.

19. The self-sanitizing structure of claim 18, wherein:
each of the individually addressable energy sources, when activated, projects onto the contact surface the sanitizing light, wherein the sanitizing electromagnetic radiation on the contact surface has a sanitizing electromagnetic energy footprint; and
the first mapping associates the sanitizing electromagnetic radiation footprint of each of the individually addressable energy sources with one or more of the contact surface locations.

* * * * *